US008986970B2

(12) United States Patent
Jones et al.

(10) Patent No.: US 8,986,970 B2
(45) Date of Patent: Mar. 24, 2015

(54) **DETERGENT COMPOSITIONS CONTAINING *BACILLUS AGARADHAERENS* MANNANASE AND METHODS OF USE THEREOF**

(71) Applicant: Danisco US Inc., Palo Alto, CA (US)

(72) Inventors: Brian E. Jones, Leidschendam (GB); Marc Kolkman, Oegstgeest (NL); Zhen Qian, Shanghai (CN); Brian Sogaard Laursen, Kalunbourg (NL); Karsten M. Kragh, Viby J (DK); Sina Pricelius, Leiden (NL); Zheyong Yu, Shanghai (CN); Lilia Maria Babe, Emerald Hills, CA (US); Melodie Estabrook, Mountain View, CA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 14/321,643

(22) Filed: Jul. 1, 2014

(65) Prior Publication Data

US 2014/0377841 A1  Dec. 25, 2014

Related U.S. Application Data

(63) Continuation of application No. 14/114,709, filed as application No. PCT/US2012/035454 on Apr. 27, 2012, now Pat. No. 8,802,388, which is a continuation of application No. PCT/CN2011/073525, filed on Apr. 29, 2011.

(30) Foreign Application Priority Data

Apr. 29, 2011  (CN) ................. PCT/CN2011/073525

(51) Int. Cl.
| | | |
|---|---|---|
| *C12N 9/12* | (2006.01) | |
| *C12N 15/00* | (2006.01) | |
| *C12N 1/20* | (2006.01) | |
| *C12N 9/24* | (2006.01) | |
| *C11D 3/386* | (2006.01) | |

(52) U.S. Cl.
CPC .......... *C12N 9/2494* (2013.01); *C11D 3/38636* (2013.01)
USPC ...................... 435/200; 435/252.3; 435/320.1

(58) Field of Classification Search
USPC .................................... 435/200, 252.3, 320.1
See application file for complete search history.

(56) References Cited

U.S. PATENT DOCUMENTS

| | | | |
|---|---|---|---|
| 4,246,612 A | 1/1981 | Berry et al. | |
| 4,430,243 A | 2/1984 | Bragg | |
| 4,435,307 A | 3/1984 | Barbesgaard et al. | |
| 4,810,410 A | 3/1989 | Diakun et al. | |
| 4,977,252 A | 12/1990 | Chiu | |
| 5,019,292 A | 5/1991 | Baeck et al. | |
| 5,227,084 A | 7/1993 | Martens et al. | |
| RE34,606 E | 5/1994 | Estell et al. | |
| 5,340,735 A | 8/1994 | Christianson et al. | |
| 5,354,559 A | 10/1994 | Morehouse | |
| 5,486,303 A | 1/1996 | Capeci et al. | |
| 5,489,392 A | 2/1996 | Capeci et al. | |
| 5,500,364 A | 3/1996 | Christianson et al. | |
| 5,516,448 A | 5/1996 | Capeci et al. | |
| 5,565,422 A | 10/1996 | Del Greco et al. | |
| 5,569,645 A | 10/1996 | Dinniwell et al. | |
| 5,574,005 A | 11/1996 | Welch et al. | |
| 5,576,282 A | 11/1996 | Miracle et al. | |
| 5,595,967 A | 1/1997 | Miracle et al. | |
| 5,597,936 A | 1/1997 | Perkins et al. | |
| 5,646,101 A | 7/1997 | MacBeath | |
| 5,686,014 A | 11/1997 | Baillely | |
| 5,691,297 A | 11/1997 | Nassano et al. | |
| 5,695,679 A | 12/1997 | Christie et al. | |
| 5,698,504 A | 12/1997 | Christie et al. | |
| 5,700,676 A | 12/1997 | Bott et al. | |
| 5,705,464 A | 1/1998 | Scheper et al. | |
| 5,710,115 A | 1/1998 | Patel et al. | |
| 5,714,183 A | 2/1998 | Nicolas et al. | |
| 5,801,039 A | 9/1998 | Maurer et al. | |
| 5,855,625 A | 1/1999 | Maurer et al. | |
| 5,874,276 A | 2/1999 | Fowler et al. | |
| 5,879,584 A | 3/1999 | Bianchetti et al. | |
| 5,935,826 A | 8/1999 | Blue et al. | |
| 5,955,340 A | 9/1999 | Bott et al. | |
| 6,060,299 A | 5/2000 | Sreekrishna et al. | |
| 6,225,464 B1 | 5/2001 | Hiler, II et al. | |
| 6,306,812 B1 | 10/2001 | Perkins et al. | |
| 6,312,936 B1 | 11/2001 | Poulose et al. | |
| 6,326,348 B1 | 12/2001 | Vinson et al. | |

(Continued)

FOREIGN PATENT DOCUMENTS

| | | |
|---|---|---|
| CA | 2162459 | 11/1994 |
| CA | 2162460 | 11/1994 |

(Continued)

OTHER PUBLICATIONS

Ademark, P., et al., "Softwood hemicellulose-degrading enzymes from *Aspergillus niger*: purification and properties of a β-mannanase." *J. Biotechnol.* 63: 199-210, 1998.

Akino, T., et al., "The cloned β-mannanase gene from alkalophilic *Bacillus* sp. AM-001 produces two β-mannanases in *Escherichia coli*." *Arch. Microbiol.* 152: 10-15, 1989.

(Continued)

*Primary Examiner* — Maryam Monshipouri
(74) *Attorney, Agent, or Firm* — Danisco US Inc.

(57) ABSTRACT

The present compositions and methods relate to an endo-β-mannanase cloned from *Bacillus agaradhaerens*, polynucleotides encoding the endo-β-mannanase, and methods of use thereof. Formulations containing the endo-β-mannanase are highly suitable for use as detergents.

6 Claims, 12 Drawing Sheets

(56) References Cited

U.S. PATENT DOCUMENTS

| | | | |
|---|---|---|---|
| 6,376,445 | B1 | 4/2002 | Bettiol et al. |
| 6,376,450 | B1 | 4/2002 | Ghosh et al. |
| 6,482,628 | B1 | 11/2002 | Poulose et al. |
| 6,566,114 | B1 | 5/2003 | Kauppinen et al. |
| 6,602,842 | B2 | 8/2003 | Cuperus et al. |
| 6,605,458 | B1 | 8/2003 | Hansen et al. |
| 6,610,642 | B2 | 8/2003 | Ghosh et al. |
| 2008/0090747 | A1 | 4/2008 | Augustinus et al. |

FOREIGN PATENT DOCUMENTS

| | | |
|---|---|---|
| EP | 0011340 | 5/1980 |
| EP | 0026528 | 4/1981 |
| EP | 0214761 | 3/1987 |
| EP | 0218272 | 4/1987 |
| EP | 0238023 | 9/1987 |
| EP | 0242919 | 10/1987 |
| EP | 0258068 | 3/1988 |
| EP | 0299575 | 1/1989 |
| EP | 0305216 | 3/1989 |
| EP | 0313146 | 4/1989 |
| EP | 0331376 | 9/1989 |
| EP | 0495257 | 7/1992 |
| EP | 0766727 | 8/2002 |
| EP | 2100949 | 9/2009 |
| GB | 1296839 | 11/1972 |
| GB | 1372034 | 10/1974 |
| GB | 1400898 | 7/1975 |
| GB | 1514276 | 6/1978 |
| JP | 64/074992 | 3/1989 |
| WO | WO88/09367 | 12/1988 |
| WO | WO90/09446 | 8/1990 |
| WO | WO92/06154 | 4/1992 |
| WO | WO92/21760 | 12/1992 |
| WO | WO94/12621 | 6/1994 |
| WO | WO95/01426 | 1/1995 |
| WO | WO95/23221 | 8/1995 |
| WO | WO95/35362 | 12/1995 |
| WO | WO97/11151 | 3/1997 |
| WO | WO99/06521 | 2/1999 |
| WO | WO99/34011 | 7/1999 |
| WO | WO9964573 | 12/1999 |
| WO | WO9964619 | 12/1999 |
| WO | WO00/32601 | 6/2000 |
| WO | WO2005/056782 | 6/2005 |
| WO | WO2007/044993 | 4/2007 |
| WO | WO2007/145964 | 12/2007 |
| WO | WO2010/115021 | 10/2010 |

OTHER PUBLICATIONS

Arcand, N., et al., "β-Mannanase of *Streptomyces lividans* 66: cloning and DNA sequence of the *manA* gene and characterization of the enzyme" *J.Biochem.* 290: 857-863, 1993.
Bicho, P.A., et al., "The characterisation of a thermostable endo-β-1,4-mannanase cloned from "*Caldocellum saccharolyticum*"." *Appl. Microbiol. Biotechnol.* 36: 337-343, 1991.
Braithwaite, K.L., et al., "A non-modular endo-β-1,4-mannanase from *Pseudomonas fluorescens* subspecies cellulosa." Biochem J. 305: 1005-1010, 1995.
Cann, I.K.O. et al., "Molecular Cloning, Sequencing, and Expression of a Novel Multidomain Mannanase Gene from *Thermoanaerobacterium polysaccharolyticum*." *J. Bacteriol.* 181(5) 1643-1651, 1999.
Charrier, M., et al., "Mannan-Degrading Enzymes Purified From the Crop of the Brown Garden Snail *Helix aspersa* Müller (Gastropoda Pulmonata)." *Journal of Experimental Zoology* 290: 125-135 2001.
Chen, X., et al., "Cloning, functional expression and characterization of *Aspergillus sulphureus* β-mannanase in *Pichia pastoris*." *J. Biotechnol.* 128(3): 452-461, 2007.
Cho, K.M. et al., "Ace144C-man26A gene of endophytic *Paenibacillus polymyxa* GS01 has multi-glycosyl hydrolases in two catalytic domains." *Appl. Microbiol Biotechnol.* 73(3): 618-630, 2006.

Civas, A., et al., "Glycosidases induced in *Aspergillus tamarii*— Secreted α-D-galactosidase and β-mannanase." *Biochem. J.* 219: 857-863, 1984.
Dartois, V., et al., "Cloning, nucleotide sequence and expression in *Escherichia coli* of a lipase gene from *Bacillus subtilis* 168." *Biochem. Biophys. Acta* 1131:253-260, 1992.
Dhawan, S., et al, "Microbial Mannanases: An Overview of Production and Applications." *Critical Reviews in Biotechnology* 27(4): 197-216, 2007.
Duffaud, G.D., et al. "Purification and Characterization of Extremely Thermostable β-Mannanase, β-Mannosidase, and α-Galactosidase from the Hyperthermophilic Eubacterium *Thermotoga neapolitana* 5068." *Appl. Environ. Microbiol.* 63: 169-177, 1997.
Fanutti, C., et al., "The Conserved Noncatalytic 40-Residue Sequence in Cellulases and Hemicellulases from Anaerobic Fungi Functions as a Protein." *J. Biological Chemistry* 270(49): 29314-29322, 1994.
Filichkin, S.A., et al., "A Novel Endo-β-Mannanase Gene in Tomato LeMAN5 Is Associated with Anther and Pollen Development." *Plant Physiol.* 134:1080-1087, 2000.
Franco, P.F., et al., "Production and characterization of hemicellulase activities from *Trichoderma harzianum* strain T4." *Biotechnol Appl. Biochem.* 40: 255-259, 2004.
Gherardini, F.C., et al., "Purification and Characterization of a Cell-Associated, Soluble Mannanase from *Bacteroides ovatus*." *J. Bacteriol.* 169: 2038-2043, 1987.
Gibbs, M.D., et al., "Sequencing and Expression of a β-Mannanase Gene from the Extreme Thermophile *Dictyoglomus thermophilum* Rt46B.1, and Characteristics of the Recombinant Enzyme." *Curr. Microbiol.* 39(6): 351-357, 1999.
Haas, M.J., et al., "Cloning, Expression and characterization of a cDNA encoding lipase from *Rhizopus delemar*." *Gene* 109:107-113, 1991.
Halstead, J.R., et al., "A family 26 mannanase produced by *Clostridium thermocellum* as a component of the cellulosome contains a domain which is conserved in mannanases from anaerobic fungi." *Microbiol.* 145: 3101-3108, 1999.
Hatada, Y., et al., "Sequence of the gene for a high-alkaline mannanase from an alkaliphilic *Bacillus* sp. strain JAMB-750, its expression in *Bacillus subtilis* and characterization of the recombinant enzyme." *Extremophiles* 9: 497-500, 2005.
Hayashi, T., Xyloglucans in the Primary Cell Wall. *Annu. Rev. Plant Physiol. Plant Mol. Biol.* 40: 139-168, 1989.
Hilge, M., et al., "High-resolution native and complex structures of thermostable b-mannanase from *Thermomonospora fusca*—substrate specificity in glycosyl hydrolase family 5." *Structure* 6: 1433-1444, 1998.
Horikoshi, K., "Production of Alkaline Enzymes by Alkalophilic Microorganisms Part III. Alkaline Pectinase of *Bacillus* No. P-4-N." *Agr. Biol. Chem.* 36(2): 285-293, 1972.
Kansoh, A.L., et al., "Xylanase and Mannanase enzymes from *Streptomyces galbus* NR and their use in biobleaching of softwood kraft pulp." *Antonie van Leeuwenhoek* 85: 103-114, 2004.
Kataoka, N., et al., "Isolation and characterization of an active mannanase-producing anaerobic bacterium, *Clostridium tertium* KT-5A, from lotus soil." *J. Appl. Microbiol.* 84: 357-367, 1998.
Kugimiya, W., et al., "Cloning and Sequence Analysis of cDNA encoding *Rhizopus niveus* Lipase." *Biosci. Biotech. Biochem.* 56(5):716-719, 1992.
Lever, M., "A New Reaction for Colorimetric Determination of Carbohydrates." Analytical Biochemistry 47: 273-279, 1972.
Ll, Y.N., et al., "A β-Mannanase from *Bacillus subtilis* B36: Purification, Properties, Sequencing, Gene Cloning and Expression in *Escherichia coli*." *Z. Naturforsch* 61c: 840-846, 2006.
Ma, Y., et al., "Characterization and gene cloning of a novel β-mannanase from alkaliphilic *Bacillus* sp. N16-5." *Extremophiles* 8: 447-454, 2004.
Matsushita, O., et al., "A *Bacteroides* ruminicola 1,4-β-D-Endoglucanase Is Encoded in Two Reading Frames." *J. Bacteriol.* 173(21): 6919-6926, 1991.
Mendoza, N. S., et al., "Purification and properties of mannanase from *Bacillus subtilis*." *World Journal of Microbiology & Biotechnology* 10: 551-555, 1994.

(56) References Cited

OTHER PUBLICATIONS

Moreira, L.R.S., et al., "An overview of mannan structure and mannan-degrading enzyme systems." *Appl. Microbiol. Biotechnol.* 79: 165-178, 2008.

Morris, D.D., et al., "Correction of the β-Mannanase Domain of the *celC* Pseudogene from *Caldocellulosiruptor saccharolyticus* and Activity of the Gene Product on Kraft Pulp." *Appl. Environ. Microbiol.* 61(6): 2262-2269, 1995.

Nakajima, N., et al., "Purification and Characterization of Konjac Glucomannan Degrading Enzyme from Anaerobic Human Intestinal Bacterium, *Clostridium butyricum-Clostridium beijerinckii* Group." *Biosci. Biotech. Biochem.* 61(10): 1739-1742, 1997.

Parker, K.N., et al., "Galactomannanases Man2 and Man5 from *Thermotoga* Species: Growth Physiology on Galactomannans, Gene Sequence Analysis, and Biochemical Properties of Recombinant Enzymes." *Biotechnol. Bioeng.* 75(3): 322-333, 2001.

Pason, P., et al., "*Paenibacillus curdlanolyticus* Strain B-6 Xylanolytic-Cellulolytic Enzyme System That Degrades Insoluble Polysaccharides."*Appl. Environ. Microbiol.*72(4): 2483-2490, 2006.

Politz, O., et al., "A highly thermostable endo-(1,4)-β-mannanase from the marine bacterium *Rhodothermus marinus*." *Appl. Microbiol. Biotechnol.* 53: 715-721, 2000.

Purchart, V., et al., "Purification and characterization of two forms of endo-β-1,4- mannanase from a thermotolerant fungus, *Aspergillus fumigatus* IMI 385708 (formerly *Thermomyces lanuginosus* IMI 158749)." *Biochimica et Biophysica Acta* 1674: 239-250, 2004.

Regalado, C., et al., "Production, partial purification and properties of β-mannanases obtained by solid substrate fermentation of spent soluble coffee wastes and copra paste using *Aspergillus oryzae* and *Aspergillus niger*."*Journal of the Science of Food and Agriculture* 80: 1343-1350, 2000.

Sachslehner, A., et al., "Hydrolysis of isolated coffee mannan and coffee extract by mannanases of *Sclerotium rolfsii*." *J. Biotechnol.* 80: 127-134, 2000.

Schimada, Y., et al., "cDNA Molecular Cloning of *Geotrichum candidum* Lipase." *J. Biochem.* 106: 383-388, 1989.

Setati, M.E., et al., "Expression of the *Aspergillus aculeatus* Endo-β-1,4-mannanase Encoding Gene (man1) in *Saccharomyces cerevisiae* and Characterization of the Recombinant Enzyme." *Protein Expression and Purification* 21: 105-114, 2001.

Shevchik, V.E., et al., "Production of pectolytic enzymes from *Erwinia* grown on different carbon sources." *World Journal of Microbiology and Biotechnology* 8: 115-120, 1992.

Stalbrand, H., et al., "Purification and characterization of two β-mannanases from *Trichoderma reesei*." *J. Biotechnol.* 29: 229-242, 1993.

Stoll, D., et al., "Mannan-Degrading Enzymes from *Cellulomonas fimi*." *Appl. Environ. Microbiol.* 65(6): 2598-2605, 1999.

Sunna, A., et al., "A Gene Encoding a Novel Multidomain β-1,4-Mannanase from *Caldibacillus cellulovorans* and Action of the Recombinant Enzyme on Kraft Pulp." *Appl. Environ. Microbiol.* 66(2): 664-670, 2000.

Talbot, G., et al., "Purification and Characterization of Thermostable β-Mannanase and α-Galactosidase from *Bacillus stearothermophilus*." *Appl. Environ. Microbiol.* 56(11): 3505-3510, 1990.

Tamaru, Y., et al., "Cloning, DNA Sequencing, and Expression of the β-1,4-Mannanase Gene from a Marine Bacterium, *Vibrio* sp. Strain MA-138." *Journal of Fermentation and Bioengineering* 83(2): 201-205, 1997.

Tang, C.M., et al., "The *cel4* Gene of *Agaricus bisporus* Encodes a β-Mannanase." *Appl. Environ. Microbio.* 67(5): 2298-2303, 2001.

Vincken, J.-P., et al, "The Effect of Xyloglucans on the Degradation of Cell-Wall-Embedded Cellulose by the Combined Action of Cellobiohydrolase and Endoglucanases from *Trichoderma viride*." *Plant Physiol.* 104: 99-107, 1994.

Wymelenberg, A.V., et al., "The *Phanerochaete chrysosporium* secretome: Database predictions and initial mass spectrometry peptide identifications in cellulose-grown medium." *J. Biotechnol.* 118: 17-34, 2005.

Yamaguchi, S., et al., "Cloning and structure of the mono- and diacylglycerol lipase-encoding gene from *Penicillium camembertii* U-150." *Gene* 103: 61-67, 1991.

Yamaura, I., et al., "Purification and Some Properties of Endo-1,4-β-D-mannanase from a Mud Snail, *Pomacea insularus* (de Ordingny)." *Biosci. Biotech. Biochem.* 57(8): 1316-1319, 1993.

Yamaura, I., et al., "Purification and Some Properties of Endo-1,4-β-D-mannanase from a Marine Mollusc, *Littorina brevicula*." *Biosci. Biotech. Biochem.* 60(4): 674-676, 1996.

Yoshida, S., et al., "Cloning, Sequence Analysis, and Expression in *Escherichia coli* of a Gene Coding for an Enzyme from *Bacillus circulans* K-1 that Degrades Guar Gum." *Biosci. Biotechnol. Biochem.* 62(3): 514-520, 1998.

Zakaria, M.M., et al., "Optimization for β-Mannanse Production of a Psychrophilic Bacterium, *Flavobacterium*sp." *Biosci. Biotechnol Biochem.* 62(4): 655-660, 1998.

Araujo, A., et al., "Hemicellulases of *Bacillus* species: preliminary comparative studies on production and properties of mannanases and galactanases." *J. Appl. Bacteriol.* 68: 253-261, 1990.

Yeoman, C.J., et al., "Thermostable Enzymes as Biocatalysts in the Biofuel Industry." *Adv. Appl. Microbiol.* 70: 1-55, 2010.

Christgau, S., et al., "Expression cloning, purification and characterization of a β-1,4 mannanase from *Aspergillus aculeatus*." *Biochemistry and Molecular Biology International* 33(5): 917-925, 1994.

El-Helow, E.R., et al., "The Development of a *Bacillus subtilis* 168 Culture Condition for Enhanced and Accelerated β-Mannanase Production." *Acta Microbiologica et Immunologica Hungarica* 43(4): 289-299, 1995.

Perret, S., et al., "Towards Design Cellulosomes in Clostridia: Mannanase Enrichment of the Cellulosomes Produced by *Clostridium cellulolyticum*." *J. Bacteriol.* 186(19): 6544-6552, 2004.

International Search Report and the Written Opinion of the International Searching Authority for International Application No. PCT/US2012/035454 dated Sep. 10, 2012.

International Preliminary Report on Patentability for International Application No. PCT/US2012/035454 dated Oct. 29, 2013.

```
  1  MINYESEVRR FEAEDAILNG VIVKNSEPGF SGIGYVGDFE DSSQSVIFHV
 51  DVPEIDLYTL IIGYGAIYGS EKVANVLVNG EKLSSFIMGS GFGKASAGNI
                                                           catalytic domain
101  VLNSGSNTIS ITPDWIHFAI DYIEVKLIPE PIKHNVEKKL INFNATDEAK
                             catalytic domain
151  VLMSYLVDNF GEKILSGQHD FPNIRPDDLE YIYEITGKYP AILGLDFIDN
                             catalytic domain
201  SFSRVEYGAF ADEIPVAINW WNKGGIVIFT WHWNAPKDLL DEFGNEWWRG
                             catalytic domain
251  FYTEATTFDV EYALNHPDSE DYKLLIRDID VIADELKKLQ KADVFVLWRP
      catalytic residue
                             catalytic domain
301  LHEAEGKWFW WGKNGFEPAK ELWLLMYDRM TNYHNLWNLI WVWNSIEEDW
                                                           catalytic residue
                             catalytic domain
351  YPGDEYVDIV SFDSYPGDYN YSPMSGQYEA LKELSSNKKI IAIAENGPIP
                             catalytic domain
401  DPDLLQRYHA HYSWFTTWNG DILREQNSEE HLKNVYNHDY VIILDELPDF
451  ETYKEDVPLE
```

Figure 9

DETERGENT COMPOSITIONS CONTAINING *BACILLUS AGARADHAERENS* MANNANASE AND METHODS OF USE THEREOF

PRIORITY

The present application is a continuation of U.S. patent application Ser. No. 14/114,709, filed Oct. 29, 2013, which is a U.S. National Phase Application of International Application No. PCT/US2012/035454, filed Apr. 27, 2012, which claims priority to International Application No. PCT/CN2011/073525, filed on Apr. 29, 2011, which are hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "NB31585-US-CNT.txt" created on Jul. 1, 2014, which is 136,874 bytes in size.

TECHNICAL FIELD

The present compositions and methods relate to an endo-β-mannanase cloned from *Bacillus agaradhaerens*, polynucleotides encoding the endo-β-mannanase, and methods of use thereof. Formulations containing the endo-β-mannanase are highly suitable for use as detergents.

BACKGROUND

Current laundry detergent and fabric care compositions include a complex combination of active ingredients such as surfactants, enzymes (protease, amylase, mannanase, and/or cellulase), bleaching agents, a builder system, suds suppressors, soil-suspending agents, soil-release agents, optical brighteners, softening agents, dispersants, dye transfer inhibition compounds, abrasives, bactericides, and perfumes.

Mannanase enzymes, including endo-β-mannanases, have been employed in detergent cleaning compositions for the removal of gum stains by hydrolyzing mannans. A variety of mannans are found in nature. These include linear mannan, glucomannan, galactomannan, and glucogalactomannan. In each case, the polysaccharide contains a β-1,4-linked backbone of mannose residues that may be substituted up to 33% with glucose residues (Yeoman et al., *Adv Appl Microbiol*, Elsivier). In galactomannans or glucogalactomannans, galactose residues are linked in alpha-1,6-linkages to the mannan backbone (Moreira and Filho, *Appl Microbiol Biotechnol*, 79:165, 2008). Therefore, hydrolysis of mannan to its component sugars requires endo-1,4-β-mannanases that hydrolyze the backbone linkages to generate short chain manno-oligosaccharides that are further degraded to monosaccharides by 1,4-β-mannosidases.

However, enzymes are often inhibited by surfactants and other components present in cleaning compositions, which interferes with their ability to remove stains. For instance, proteases in laundry detergents may degrade mannanases before the removal of a gum stain. In addition, mannanases may have a limited pH and/or temperature range at which they are active, which may make them unsuitable for certain formulations and washing conditions. Accordingly, the need exists for endo-β-mannanases that retain activity in the harsh environment of cleaning compositions.

SUMMARY

The present compositions and methods relate to endo-β-mannanase1 cloned from *Bacillus agaradhaerens* (Bag Man1). Formulations containing the endo-β-mannanase are highly suitable for use as detergents.

In particular the present disclosure provides recombinant polypeptides comprising a catalytic domain of an endo-β-mannanase, wherein the catalytic domain is at least 90% (90, 91%, 92%, 93%, 94%, 95%, 96%, 97%, 98%, 99% or 100%) identical to the amino acid sequence of SEQ ID NO:10. In some embodiments, the present disclosure provides recombinant polypeptides comprising a mature from of an endo-β-mannanase, wherein the mature form is at least 85% (85%, 86%, 87%, 88%, 89%, 90, 91%, 92%, 93%, 94%, 95%, 96%, 97%, 98%, 99% or 100%) identical to the amino acid sequence of SEQ ID NO:7. In some preferred embodiments, the polypeptide has measurable mannanase activity in the presence of detergent. In some embodiments, the polypeptide has measurable mannanase activity in the presence of a protease. In some embodiments, the polypeptide and the protease are both present at from about 0.1 to about 10.0 ppm. In some embodiments, the polypeptide retains greater than 70% mannanase activity at pH values of between 5 and 6. In a subset of these embodiments, the polypeptide has a pH optimum of about 6. In some embodiments, the polypeptide retains greater than 70% mannanase activity at a temperature range from 40° C. to 55° C. In a subset of these embodiments, the polypeptide has a temperature optimum of about 50° C. In some embodiments, the polypeptide is capable of hydrolyzing a substrate selected from the group consisting of chocolate ice cream, guar gum, locust bean gum, and combinations thereof. In some embodiments, the amino acid sequence is at least 95% identical to one of the group consisting of SEQ ID NOS:4-10. In some embodiments, the polypeptide further comprises an amino-terminal extension of Ala-Gly-Lys. In some embodiments, the polypeptide further comprises a native or non-native signal peptide. In some embodiments, the polypeptide further comprises at least one carbohydrate-binding module. In other embodiments, the polypeptide does not comprise a carbohydrate-binding module.

Also provided by the present disclosure are detergent compositions comprising at least one recombinant polypeptide of the preceding paragraph. In some embodiments, the composition further comprises a surfactant. In some embodiments, the surfactant is selected from the group consisting of sodium dodecylbenzene sulfonate, sodium hydrogenated cocoate, sodium laureth sulfate, C12-14 pareth-7, C12-15 pareth-7, sodium C12-15 pareth sulfate, C14-15 pareth-4, and combinations thereof. In some preferred embodiments, the surfactant is an ionic surfactant. In some embodiments, the ionic surfactant is selected from the group consisting of an anionic surfactant, a cationic surfactant, a zwitterionic surfactant, and a combination thereof. In some preferred embodiments, the composition further comprises an enzyme selected from the group consisting proteases, proteases, peroxidases, cellulases, beta-glucanases, hemicellulases, lipases, acyl transferases, phospholipases, esterases, laccases, catalases, aryl esterases, amylases, alpha-amylases, glucoamylases, cutinases, pectinases, pectate lyases, keratinases, reductases, oxidases, phenoloxidases, lipoxygenases, ligninases, carrageenases, pullulanases, tannases, arabinosidases, hyaluronidases, chondroitinases, xyloglucanases, xylanases, pectin acetyl esterases, polygalacturonases, rhamnogalacturonases, other endo-β-mannanases, exo-β-mannanases, pectin methylesterases, cellobiohydrolases, transglutaminases, and combinations thereof. In some embodiments, the combination comprises a protease and an amylase. In some embodiments, the detergent is selected from the group consisting of a laundry detergent, a fabric softening detergent, a dishwashing detergent, and a hard-surface cleaning detergent. In some embodiments, the detergent is in a form selected from the group consisting of a liquid, a powder, a granulated solid, and a tablet. In addition the present disclosure provides methods for hydrolyzing a mannan substrate present in a soil or stain on a surface, comprising: contacting the surface with the detergent composition to produce a clean surface. Also provided are methods of textile cleaning comprising: contacting a soiled textile with the detergent composition to produce a clean textile.

Moreover, the present disclosure provides isolated nucleic acids encoding the recombinant polypeptide of the preceding paragraphs. Also provided are expression vectors comprising the isolated nucleic acid in operable combination to a regulatory sequence. Additionally, host cells comprising the expression vector are provided. In some embodiments, the host cell is a bacterial cell or a fungal cell. The present disclosure further provides methods of producing an endo-β-mannanase, comprising: culturing the host cell in a culture medium, under suitable conditions to produce a culture comprising the endo-β-mannanase. In some embodiments, the methods further comprise removing the host cells from the culture by centrifugation, and removing debris of less than 10 kDa by filtration to produce an endo-β-mannanase-enriched supernatant. The present disclosure further provides methods for hydrolyzing a polysaccharide, comprising: contacting a polysaccharide comprising mannose with the supernatant to produce oligosaccharides comprising mannose. In some embodiments, the polysaccharide is selected from the group consisting of mannan, glucomannan, galactomannan, galactoglucomannan, and combinations thereof.

These and other aspects of Bag Man1 compositions and methods will be apparent from the following description.

DESCRIPTION OF THE DRAWINGS

Figure 7A:
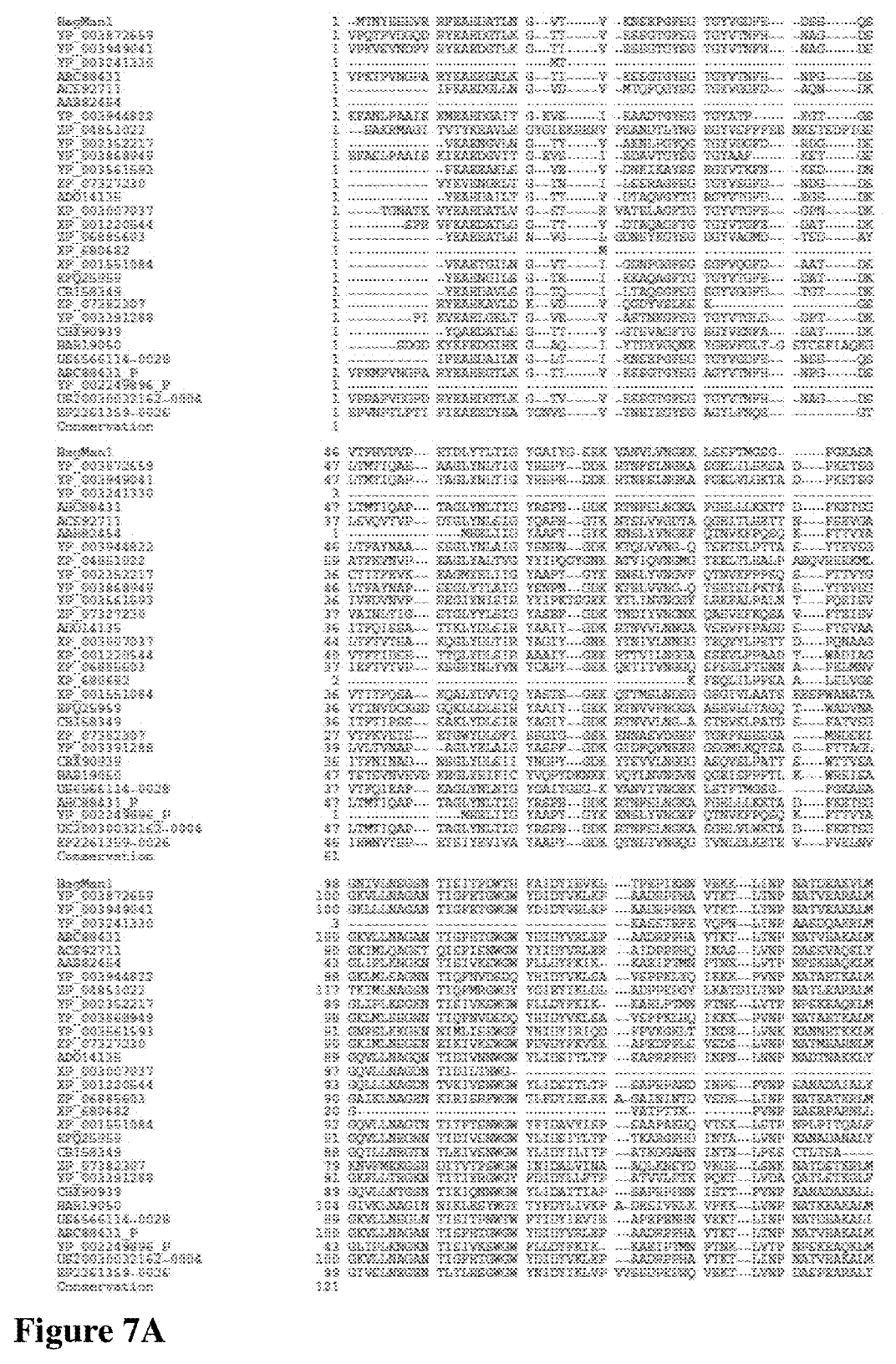
Figure 7B:
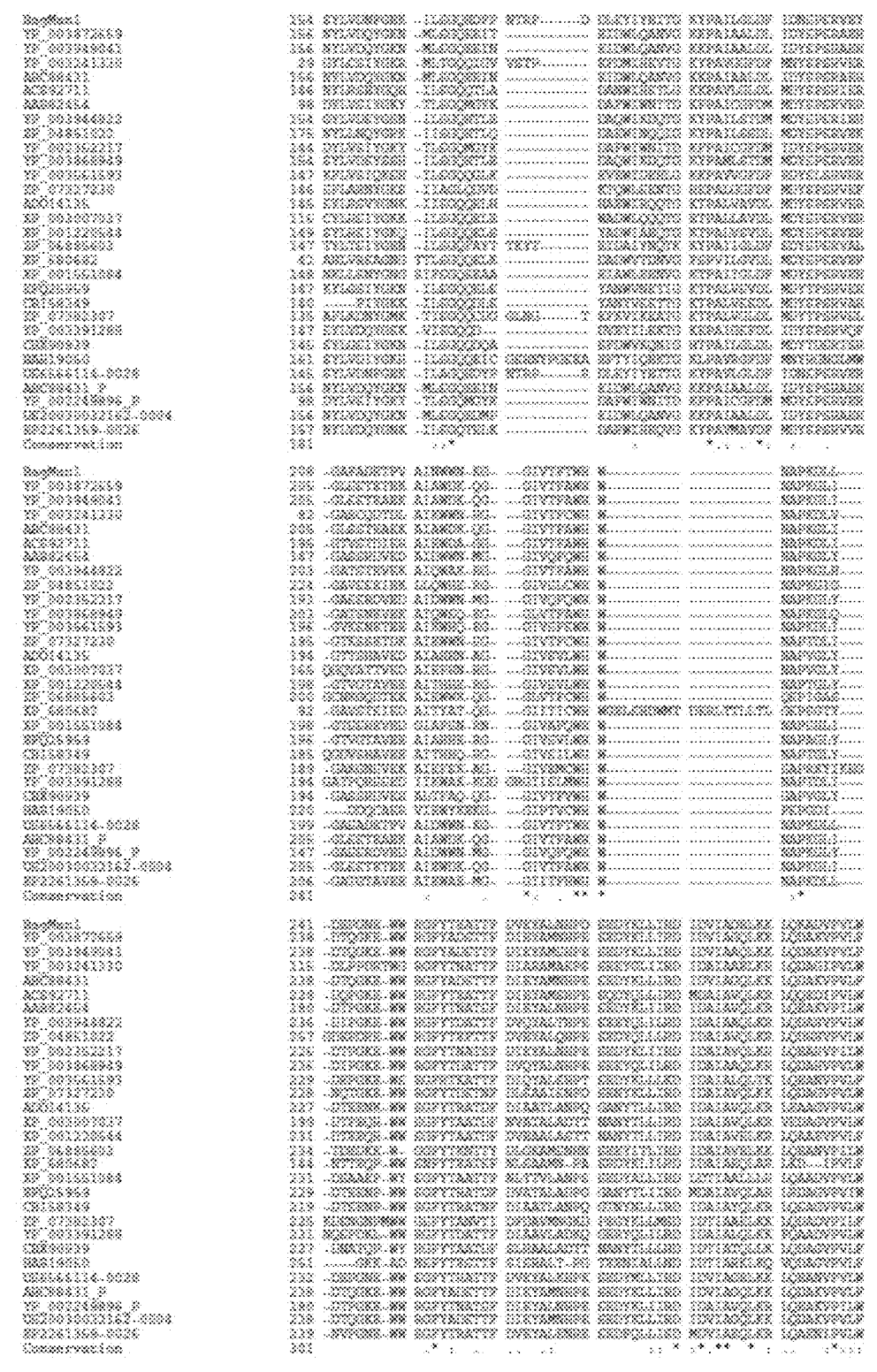
Figure 7C:
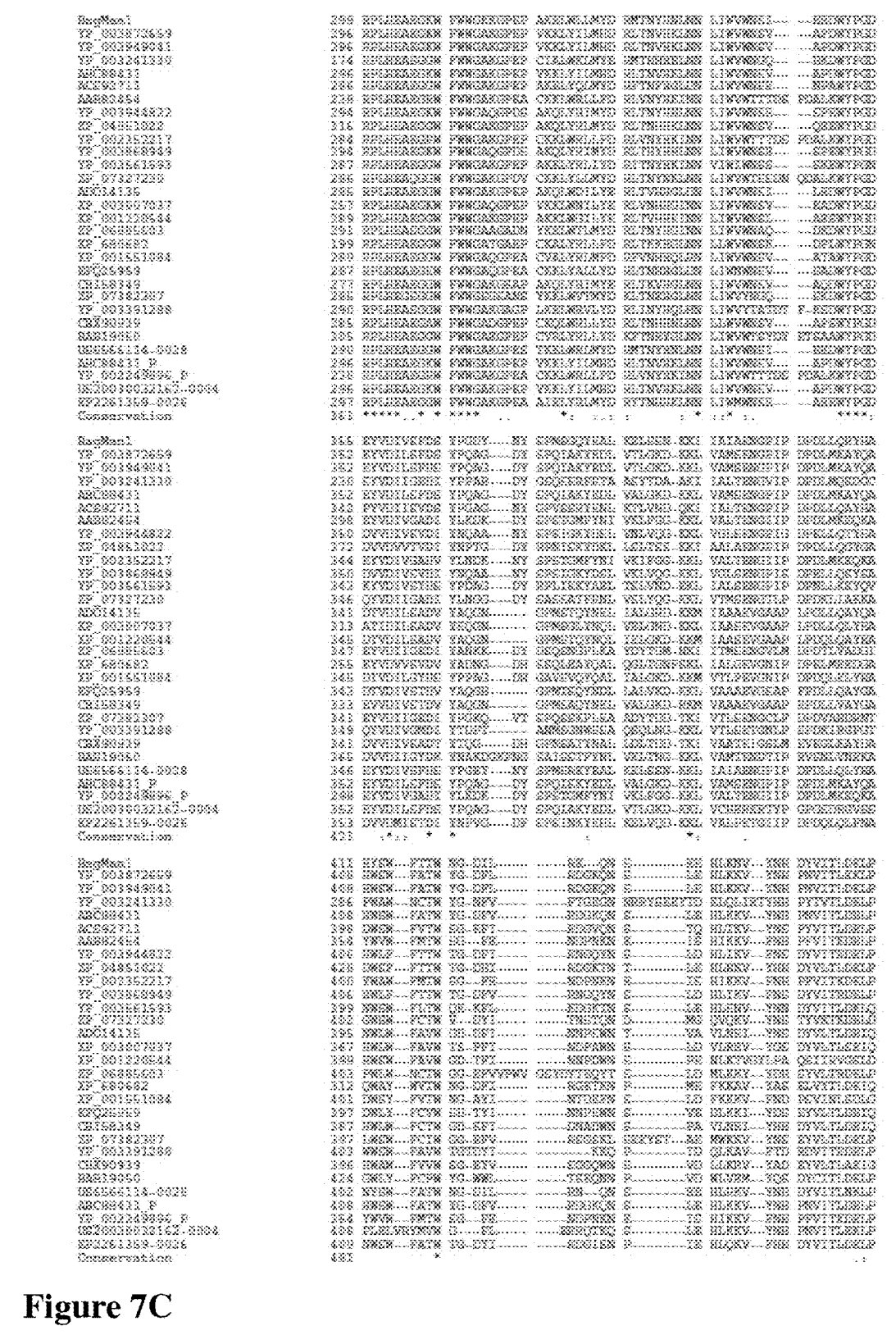
Figure 7D:
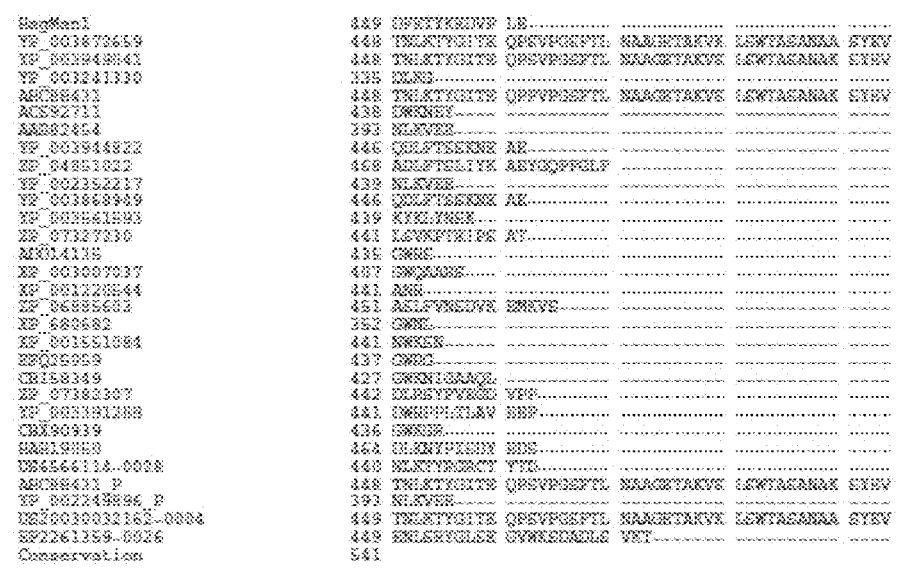

FIG. 7A-D provides an alignment of the amino acid sequence of the mature form of Bag Man1 (SEQ ID NO:6) with the sequences of other microbial mannanases (SEQ ID NOs:11-39). Table 7-1 lists the homologous mannanases by NCBI and SEQ ID NO.

FIG. 9 shows the predicted functional domains of Bag Man1. The catalytic domain of Bag Man 1 (SEQ ID NO:10) corresponds to residues 141-446 of SEQ ID NO:6. The two predicted catalytic glutamic acid (E) residues are marked. Also shown are the two predicted carbohydrate-binding modules of Bag Man1.

DETAILED DESCRIPTION

I. Introduction

Figure 1:
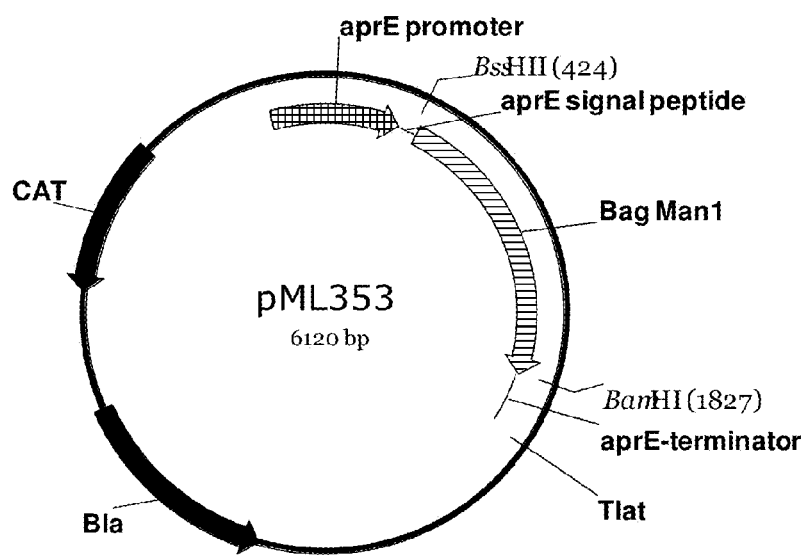
FIG. 1 provides a plasmid map of pML353 (aprE-Bag Man1).

Described are compositions and methods relating to endo-β-mannanase1 cloned from *Bacillus agaradhaerens* strain C11SB-G17 (Bag Man1). The compositions and methods are based, in part, on the observation that recombinant Bag Man1 has glycosyl hydrolase activity in the presence of detergent compositions. This feature of Bag Man1 makes it well suited for use in a variety of cleaning applications, where the enzyme can hydrolyze mannans in the presence of surfactants and other components found in detergent compositions.

II. Definitions

Prior to describing the present compositions and methods in detail, the following terms are defined for clarity. Terms and abbreviations not defined should be accorded their ordinary meaning as used in the art:

As used herein, a "mannan endo-1,4-β-mannosidase," "endo-1,4-β-mannanase," "endo-β-1,4-mannase," "β-mannanase B," "β-1,4-mannan 4-mannanohydrolase," "endo-β-mannanase," "β-D-mannanase," "1,4-β-D-mannan mannanohydrolase," or "endo-β-mannanase" (EC 3.2.1.78) refers to an enzyme capable of the random hydrolysis of 1,4-β-D-mannosidic linkages in mannans, galactomannans and glucomannans. Endo-1,4-β-mannanases are members of several families of glycosyl hydrolases, including GH26 and GH5. In particular, endo-β-mannanases constitute a group of polysaccharases that degrade mannans and denote enzymes that are capable of cleaving polyose chains containing mannose units (i.e., are capable of cleaving glycosidic bonds in mannans, glucomannans, galactomannans and galactogluco-mannans). The "endo-β-mannanases" of the present disclosure may possess additional enzymatic activities (e.g., endo-1,4-β-glucanase, 1,4-β-mannosidase, cellodextrinase activities, etc.).

As used herein, a "mannanase," "mannosidic enzyme," "mannolytic enzyme," "mannanase enzyme," "mannanase polypeptides," or "mannanase proteins" refers to an enzyme, polypeptide, or protein exhibiting a mannan degrading capability. The mannanase enzyme may be, for example, an endo-β-mannanase, an exo-β-mannanase, or a glycosyl hydrolase. As used herein, mannanase activity may be determined according to any procedure known in the art (See, e.g., Lever, *Anal. Biochem,* 47:248, 1972; U.S. Pat. No. 6,602,842; and International Publication No. WO 95/35362A1).

As used herein, "mannans" are polysaccharides having a backbone composed of β-1,4-linked mannose; "glucomannans" are polysaccharides having a backbone of more or less regularly alternating β-1,4 linked mannose and glucose; "galactomannans" and "galactoglucomannans" are mannans and glucomannans with alpha-1,6 linked galactose side-branches. These compounds may be acetylated. The degradation of galactomannans and galactoglucomannans is facilitated by full or partial removal of the galactose sidebranches. Further the degradation of the acetylated mannans, glucomannans, galactomannans and galactoglucomannans is facilitated by full or partial deacetylation. Acetyl groups can be removed by alkali or by mannan acetylesterases. The oligomers that are released from the mannanases or by a combination of mannanases and alpha-galactosidase and/or mannan acetyl esterases can be further degraded to release free maltose by β-mannosidase and/or β-glucosidase As used herein, "catalytic activity" or "activity" describes quantitatively the conversion of a given substrate under defined reaction conditions. The term "residual activity" is defined as the ratio of the catalytic activity of the enzyme under a certain set of conditions to the catalytic activity under a different set of conditions. The term "specific activity" describes quantitatively the catalytic activity per amount of enzyme under defined reaction conditions.

As used herein, "pH-stability" describes the property of a protein to withstand a limited exposure to pH-values significantly deviating from the pH where its stability is optimal (e.g., more than one pH-unit above or below the pH-optimum, without losing its activity under conditions where its activity is measurable).

As used herein, the phrase "detergent stability" refers to the stability of a specified detergent composition component (such as a hydrolytic enzyme) in a detergent composition mixture.

As used herein, a "perhydrolase" is an enzyme capable of catalyzing a reaction that results in the formation of a peracid suitable for applications such as cleaning, bleaching, and disinfecting.

As used herein, the term "aqueous," as used in the phrases "aqueous composition" and "aqueous environment," refers to a composition that is made up of at least 50% water. An aqueous composition may contain at least 50% water, at least 60% water, at least 70% water, at least 80% water, at least 90% water, at least 95% water, at least 97% water, at least 99% water, or even at least 99% water.

As used herein, the term "surfactant" refers to any compound generally recognized in the art as having surface active qualities. Surfactants generally include anionic, cationic, nonionic, and zwitterionic compounds, which are further described, herein.

As used herein, "surface property" is used in reference to electrostatic charge, as well as properties such as the hydrophobicity and hydrophilicity exhibited by the surface of a protein.

The term "oxidation stability" refers to endo-β-mannanases of the present disclosure that retain a specified amount of enzymatic activity over a given period of time under conditions prevailing during the mannosidic, hydrolyzing, cleaning, or other process disclosed herein, for example while exposed to or contacted with bleaching agents or oxidizing agents. In some embodiments, the endo-β-mannanases retain at least about 50%, about 60%, about 70%, about 75%, about 80%, about 85%, about 90%, about 92%, about 95%, about 96%, about 97%, about 98%, or about 99% endo-β-mannanase activity after contact with a bleaching or oxidizing agent over a given time period, for example, at least about 1 minute, about 3 minutes, about 5 minutes, about 8 minutes, about 12 minutes, about 16 minutes, about 20 minutes, etc.

The term "chelator stability" refers to endo-β-mannanases of the present disclosure that retain a specified amount of enzymatic activity over a given period of time under conditions prevailing during the mannosidic, hydrolyzing, cleaning, or other process disclosed herein, for example while exposed to or contacted with chelating agents. In some embodiments, the endo-β-mannanases retain at least about 50%, about 60%, about 70%, about 75%, about 80%, about 85%, about 90%, about 92%, about 95%, about 96%, about 97%, about 98%, or about 99% endo-β-mannanase activity after contact with a chelating agent over a given time period, for example, at least about 10 minutes, about 20 minutes, about 40 minutes, about 60 minutes, about 100 minutes, etc.

The terms "thermal stability" and "thermostable" refer to endo-β-mannanases of the present disclosure that retain a specified amount of enzymatic activity after exposure to identified temperatures over a given period of time under conditions prevailing during the mannosidic, hydrolyzing, cleaning, or other process disclosed herein, for example, while exposed to altered temperatures. Altered temperatures include increased or decreased temperatures. In some embodiments, the endo-β-mannanases retain at least about 50%, about 60%, about 70%, about 75%, about 80%, about 85%, about 90%, about 92%, about 95%, about 96%, about 97%, about 98%, or about 99% endo-β-mannanase activity after exposure to altered temperatures over a given time period, for example, at least about 60 minutes, about 120 minutes, about 180 minutes, about 240 minutes, about 300 minutes, etc.

The term "cleaning activity" refers to the cleaning performance achieved by the endo-β-mannanase under conditions prevailing during the mannosidic, hydrolyzing, cleaning, or other process disclosed herein. In some embodiments, cleaning performance is determined by the application of various cleaning assays concerning enzyme sensitive stains, for example ice cream, ketchup, BBQ sauce, mayonnaise, chocolate milk, body lotion, locust bean gum, or guar gum as determined by various chromatographic, spectrophotometric or other quantitative methodologies after subjection of the stains to standard wash conditions. Exemplary assays include, but are not limited to those described in WO 99/34011, U.S. Pat. No. 6,605,458, and U.S. Pat. No. 6,566,114 (all of which are herein incorporated by reference), as well as those methods included in the Examples.

As used herein, the terms "clean surface" and "clean textile" refer to a surface or textile respectively that has a percent stain removal of at least 10%, preferably at least 15%, 20%, 25%, 30%, 35%, or 40% of a soiled surface or textile.

The term "cleaning effective amount" of an endo-β-mannanase refers to the quantity of endo-β-mannanase described hereinbefore that achieves a desired level of enzymatic activity in a specific cleaning composition. Such effective amounts are readily ascertained by one of ordinary skill in the art and are based on many factors, such as the particular endo-β-mannanase used, the cleaning application, the specific composition of the cleaning composition, and whether a liquid or dry (e.g., granular, bar) composition is required, etc.

The term "cleaning adjunct materials," as used herein, means any liquid, solid or gaseous material selected for the particular type of cleaning composition desired and the form of the product (e.g., liquid, granule, powder, bar, paste, spray, tablet, gel, or foam composition), which materials are also preferably compatible with the endo-β-mannanase enzyme used in the composition. In some embodiments, granular compositions are in "compact" form, while in other embodiments, the liquid compositions are in a "concentrated" form.

As used herein, "cleaning compositions" and "cleaning formulations" refer to admixtures of chemical ingredients that find use in the removal of undesired compounds (e.g., soil or stains) from items to be cleaned, such as fabric, dishes, contact lenses, other solid surfaces, hair, skin, teeth, and the like. The composition or formulations may be in the form of a liquid, gel, granule, powder, or spray, depending on the surface, item or fabric to be cleaned, and the desired form of the composition or formulation.

As used herein, the terms "detergent composition" and "detergent formulation" refer to mixtures of chemical ingredients intended for use in a wash medium for the cleaning of soiled objects. Detergent compositions/formulations generally include at least one surfactant, and may optionally include hydrolytic enzymes, oxido-reductases, builders, bleaching agents, bleach activators, bluing agents and fluorescent dyes, caking inhibitors, masking agents, enzyme activators, antioxidants, and solubilizers.

As used herein, "dishwashing composition" refers to all forms of compositions for cleaning dishware, including cutlery, including but not limited to granular and liquid forms. In some embodiments, the dishwashing composition is an "automatic dishwashing" composition that finds use in automatic dish washing machines. It is not intended that the present disclosure be limited to any particular type or dishware composition. Indeed, the present disclosure finds use in cleaning dishware (e.g., dishes including, but not limited to plates, cups, glasses, bowls, etc.) and cutlery (e.g., utensils including, but not limited to spoons, knives, forks, serving utensils, etc.) of any material, including but not limited to ceramics, plastics, metals, china, glass, acrylics, etc. The term "dishware" is used herein in reference to both dishes and cutlery.

As used herein, the term "bleaching" refers to the treatment of a material (e.g., fabric, laundry, pulp, etc.) or surface for a sufficient length of time and under appropriate pH and temperature conditions to effect a brightening (i.e., whitening) and/or cleaning of the material. Examples of chemicals suitable for bleaching include but are not limited to $ClO_2$, $H_2O_2$, peracids, $NO_2$, etc.

As used herein, "wash performance" of a variant endo-β-mannanase refers to the contribution of a variant endo-β-mannanase to washing that provides additional cleaning performance to the detergent without the addition of the variant endo-β-mannanase to the composition. Wash performance is compared under relevant washing conditions.

The term "relevant washing conditions" is used herein to indicate the conditions, particularly washing temperature, time, washing mechanics, sud concentration, type of detergent, and water hardness, actually used in households in a dish or laundry detergent market segment.

As used herein, the term "disinfecting" refers to the removal of contaminants from the surfaces, as well as the inhibition or killing of microbes on the surfaces of items. It is not intended that the present disclosure be limited to any particular surface, item, or contaminant(s) or microbes to be removed.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, a preferred filler salt is sodium sulfate.

As used herein, the terms "textile" or "textile material" refer to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, the terms "purified" and "isolated" refer to the physical separation of a subject molecule, such as Bag Man1, from its native source (e.g., *Bacillus agaradhaerens*) or other molecules, such as proteins, nucleic acids, lipids, media components, and the like. Once purified or isolated, a subject molecule may represent at least 50%, and even at least 60%, at least 70%, at least 80%, at least 85%, at least 90%, at least 95%, or more, of the total amount of material in a sample (wt/wt).

As used herein, a "polypeptide" refers to a molecule comprising a plurality of amino acids linked through peptide bonds. The terms "polypeptide," "peptide," and "protein" are used interchangeably. Proteins maybe optionally be modified (e.g., glycosylated, phosphorylated, acylated, farnesylated, prenylated, sulfonated, and the like) to add functionality. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The terms "polynucleotide" encompasses DNA, RNA, heteroduplexes, and synthetic molecules capable of encoding a polypeptide. Nucleic acids may be single-stranded or double-stranded, and may have chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. Unless otherwise indicated, nucleic acid sequences are presented in a 5'-to-3' orientation.

As used herein, the terms "wild-type" and "native" refer to polypeptides or polynucleotides that are found in nature.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

As used herein, a "variant polypeptide" refers to a polypeptide that is derived from a parent (or reference) polypeptide by the substitution, addition, or deletion, of one or more amino acids, typically by recombinant DNA techniques. Variant polypeptides may differ from a parent polypeptide by a small number of amino acid residues and may be defined by their level of primary amino acid sequence homology/identity with a parent polypeptide. Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent polypeptide.

Sequence identity may be determined using known programs such as BLAST, ALIGN, and CLUSTAL using standard parameters. (See, e.g., Altschul et al. [1990] *J. Mol. Biol.* 215:403-410; Henikoff et al. [1989] *Proc. Natl. Acad. Sci. USA* 89:10915; Karin et al. [1993] *Proc. Natl. Acad. Sci USA* 90:5873; and Higgins et al. [1988] *Gene* 73:237-244). Software for performing BLAST analyses is publicly available through the National Center for Biotechnology Information. Databases may also be searched using FASTA (Pearson et al. [1988]*Proc. Natl. Acad. Sci. USA* 85:2444-2448). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution.

As used herein, a "variant polynucleotide" encodes a variant polypeptide, has a specified degree of homology/identity with a parent polynucleotide, or hybridized under stringent conditions to a parent polynucleotide or the complement, thereof. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent polynucleotide. Methods for determining percent identity are known in the art and described immediately above.

The term "derived from" encompasses the terms "originated from," "obtained from," "obtainable from," "isolated from," and "created from," and generally indicates that one specified material find its origin in another specified material or has features that can be described with reference to the another specified material.

As used herein, the term "hybridization" refers to the process by which a strand of nucleic acid joins with a complementary strand through base pairing, as known in the art.

As used herein, the phrase "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Alternatively, or in addition, hybridization conditions can be based upon the salt or ionic strength conditions of hybridization and/or one or more stringency washes, e.g.: 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used). As used herein, stringent conditions are defined as 50° C. and 0.2×SSC (1×SSC=0.15 M NaCl, 0.015 M sodium citrate, pH 7.0).

The phrases "substantially similar" and "substantially identical" in the context of at least two nucleic acids or polypeptides means that a polynucleotide or polypeptide comprises a sequence that has at least about 90%, at least about 91%, at least about 92%, at least about 93%, at least about 94%, at least about 95%, at least about 96%, at least about 97%, at least about 98%, or even at least about 99% identical to a parent or reference sequence, or does not include amino acid substitutions, insertions, deletions, or modifications made only to circumvent the present description without adding functionality.

As used herein, an "expression vector" refers to a DNA construct containing a DNA sequence that encodes a specified polypeptide and is operably linked to a suitable control sequence capable of effecting the expression of the polypeptides in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature.

A "signal sequence" refers to a sequence of amino acids bound to the N-terminal portion of a polypeptide, and which facilitates the secretion of the mature form of the protein from the cell. The mature form of the extracellular protein lacks the signal sequence which is cleaved off during the secretion process.

The term "selective marker" or "selectable marker" refers to a gene capable of expression in a host cell that allows for ease of selection of those hosts containing an introduced nucleic acid or vector. Examples of selectable markers include but are not limited to antimicrobial substances (e.g., hygromycin, bleomycin, or chloramphenicol) and/or genes that confer a metabolic advantage, such as a nutritional advantage, on the host cell.

The term "regulatory element" as used herein refers to a genetic element that controls some aspect of the expression of nucleic acid sequences. For example, a promoter is a regulatory element which facilitates the initiation of transcription of an operably linked coding region. Additional regulatory elements include splicing signals, polyadenylation signals and termination signals.

As used herein, "host cells" are generally prokaryotic or eukaryotic hosts which are transformed or transfected with vectors constructed using recombinant DNA techniques known in the art. Transformed host cells are capable of either replicating vectors encoding the protein variants or expressing the desired protein variant. In the case of vectors which encode the pre- or pro-form of the protein variant, such variants, when expressed, are typically secreted from the host cell into the host cell medium.

The term "introduced" in the context of inserting a nucleic acid sequence into a cell, means transformation, transduction or transfection. Means of transformation include protoplast transformation, calcium chloride precipitation, electroporation, naked DNA, and the like as known in the art. (See, Chang and Cohen [1979] *Mol. Gen. Genet.* 168:111-115; Smith et al. [1986] *Appl. Env. Microbiol.* 51:634; and the review article by Ferrari et al., in Harwood, *Bacillus*, Plenum Publishing Corporation, pp. 57-72, 1989).

The terms "selectable marker" or "selectable gene product" as used herein refer to the use of a gene, which encodes an enzymatic activity that confers resistance to an antibiotic or drug upon the cell in which the selectable marker is expressed.

Other technical and scientific terms have the same meaning as commonly understood by one of ordinary skill in the art to which this disclosure pertains (See, e.g., Singleton and Sainsbury, *Dictionary of Microbiology and Molecular Biology*, 2d Ed., John Wiley and Sons, NY 1994; and Hale and Marham, *The Harper Collins Dictionary of Biology*, Harper Perennial, NY 1991).

The singular terms "a," "an," and "the" include the plural reference unless the context clearly indicates otherwise.

As used herein in connection with a numerical value, the term "about" refers to a range of −10% to +10% of the numerical value. For instance, the phrase a "pH value of about 6" refers to pH values of from 5.4 to 6.6.

Headings are provided for convenience and should not be construed as limitations. The description included under one heading may apply to the specification as a whole.

III. Bag Man1 Polypeptides, Polynucleotides, Vectors, and Host Cells

A. Bag Man1 Polypeptides

In one aspect, the present compositions and methods provide a recombinantBag Man1 endo-β-mannanase polypeptide, fragments thereof, or variants thereof. An exemplary Bag Man1 polypeptide was recombinantly expressed from a polynucleotide obtained from *Bacillus agaradhaerens*. The mature Bag Man1 polypeptide has the amino acid sequence set forth as SEQ ID NO:7. Similar, substantially identical Bag Man1 polypeptides may occur in nature, e.g., in other strains or isolates of *B. agaradhaerens*. These and other isolated Bag Man1 polypeptides are encompassed by the present compositions and methods.

In some embodiments, the isolated Bag Man1 polypeptide is a variant Bag Man1 polypeptide having a specified degree of amino acid sequence identity to the exemplified Bag Man1 polypeptide, e.g., at least 85%, at least 86%, at least 87%, at least 88%, at least 89%, at least 90%, at least 91%, at least 92%, at least 93%, at least 94%, at least 95%, at least 96%, at least 97%, at least 98%, or even at least 99% sequence identity to the amino acid sequence of SEQ ID NO:7. Sequence identity can be determined by amino acid sequence alignment, e.g., using a program such as BLAST, ALIGN, or CLUSTAL, as described herein.

In certain embodiments, the Bag Man1 polypeptides are produced recombinantly, while in others the Bag Man1 polypeptides are produced synthetically, or are purified from a native source (*B. agaradhaerens*).

In certain other embodiments, the isolated Bag Man1 polypeptide includes substitutions that do not substantially affect the structure and/or function of the polypeptide. Exemplary substitutions are conservative mutations, as summarized in Table I.

TABLE I

Amino Acid Substitutions

| Original Residue | Code | Acceptable Substitutions |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, beta-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Substitutions involving naturally occurring amino acids are generally made by mutating a nucleic acid encoding a recombinant Bag Man1 polypeptide, and then expressing the variant polypeptide in an organism. Substitutions involving non-naturally occurring amino acids or chemical modifications to amino acids are generally made by chemically modifying a recombinant Bag Man1 polypeptide after it has been synthesized by an organism.

In some embodiments, variant isolated Bag Man1 polypeptides are substantially identical to SEQ ID NO:7, meaning that they do not include amino acid substitutions, insertions, or deletions that do not significantly affect the structure, function, or expression of the polypeptide. Such variant isolated Bag Man1 polypeptides include those designed only to circumvent the present description.

In some embodiments, the isolated Bag Man1 polypeptide (including a variant thereof) has 1,4-β-D-mannosidic hydrolase activity, which includes mannanase, endo-1,4-β-D-mannanase, exo-1,4-β-D-mannanasegalactomannanase, and/or glucomannanase activity. 1,4-β-D-mannosidic hydrolase activity can be determined and measured using the assays described herein, or by other assays known in the art. In some embodiments, the isolated Bag Man1 polypeptide has activity in the presence of a detergent composition.

Bag Man1 polypeptides include fragments of "full-length" Bag Man1 polypeptides that retain 1,4-β-D-mannosidic hydrolase activity. Such fragments preferably retain the active site of the full-length polypeptides but may have deletions of non-critical amino acid residues. The activity of fragments can readily be determined using the assays described, herein, or by other assays known in the art. In some embodiments, the fragments of Bag Man1 polypeptides retain 1,4-β-D-mannosidic hydrolase activity in the presence of a detergent composition.

In some embodiments, the Bag Man1 amino acid sequences and derivatives are produced as a N- and/or C-terminal fusion protein, for example to aid in extraction, detection and/or purification and/or to add functional properties to the Bag Man1 polypeptides. Examples of fusion protein partners include, but are not limited to, glutathione-S-transferase (GST), 6×His, GAL4 (DNA binding and/or transcriptional activation domains), FLAG, MYC, BCE103 (WO 2010/044786), or other tags well known to anyone skilled in the art. In some embodiments, a proteolytic cleavage site is provided between the fusion protein partner and the protein sequence of interest to allow removal of fusion protein sequences. Preferably, the fusion protein does not hinder the activity of the isolated Bag Man1 polypeptide.

In some embodiments, the isolated Bag Man1 polypeptide is fused to a functional domain including a leader peptide, propeptide, one or more binding domain (modules) and/or catalytic domain. Suitable binding domains include, but are not limited to, carbohydrate-binding modules (e.g., CBM) of various specificities, providing increased affinity to carbohydrate components present during the application of the isolated Bag Man1 polypeptide. As described herein, the CBM and catalytic domain of the Bag Man1 polypeptide are operably linked.

A carbohydrate-binding module (CBM) is defined as a contiguous amino acid sequence within a carbohydrate-active enzyme with a discreet fold having carbohydrate-binding activity. A few exceptions are CBMs in cellulosomal scaffoldin proteins and rare instances of independent putative CBMs. The requirement of CBMs existing as modules within larger enzymes sets this class of carbohydrate-binding protein apart from other non-catalytic sugar binding proteins such as lectins and sugar transport proteins. CBMs were previously classified as cellulose-binding domains (CBDs) based on the initial discovery of several modules that bound cellulose (Tomme et al., Eur J Biochem, 170:575-581, 1988; and Gilkes et al., J Biol Chem, 263:10401-10407, 1988). However, additional modules in carbohydrate-active enzymes are continually being found that bind carbohydrates other than cellulose yet otherwise meet the CBM criteria, hence the need to reclassify these polypeptides using more inclusive terminology. Previous classification of cellulose-binding domains was based on amino acid similarity. Groupings of CBDs were called "Types" and numbered with roman numerals (e.g. Type I or Type II CBDs). In keeping with the glycoside hydrolase classification, these groupings are now called families and numbered with Arabic numerals. Families 1 to 13 are the same as Types Ito XIII (Tomme et al., in *Enzymatic Degradation of Insoluble Polysaccharides* (Saddler, J. N. & Penner, M., eds.), Cellulose-binding domains: classification and properties. pp. 142-163, American Chemical Society, Washington, 1995). A detailed review on the structure and binding modes of CBMs can be found in (Boraston et al., Biochem J, 382:769-81, 2004). The family classification of CBMs is expected to: aid in the identification of CBMs, in some cases, predict binding specificity, aid in identifying functional residues, reveal evolutionary relationships and possibly be predictive of polypeptide folds. Because the fold of proteins is better conserved than their sequences, some of the CBM families can be grouped into superfamilies or clans. The current CBM families are 1-63. CBMs/CBDs have also been found in algae, e.g., the red alga *Porphyra purpurea* as a non-hydrolytic polysaccharide-binding protein. However, most of the CBDs are from cellullases and xylanases. CBDs are found at the N- and C-termini of proteins or are internal. Enzyme hybrids are known in the art (See e.g., WO 90/00609 and WO 95/16782) and may be prepared by transforming into a host cell a DNA construct comprising at least a fragment of DNA encoding the cellulose-binding domain ligated, with or without a linker, to a DNA sequence encoding a disclosed Bag Man1 polypeptide and growing the host cell to express the fused gene. Enzyme hybrids may be described by the following formula:

CBM-MR-X or X-MR-CBM

In the above formula, the CBM is the N-terminal or the C-terminal region of an amino acid sequence corresponding to at least the carbohydrate-binding module; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably from 2 to 40 amino acids; and X is an N-terminal or C-terminal region of a disclosed Bag Man1 polypeptide having mannanase catalytic activity. In addition, a mannanase may contain more than one CBM or other module(s)/domain(s) of non-glycolytic function. The terms "module" and "domain" are used interchangeably in the present disclosure.

Suitable enzymatically active domains possess an activity that supports the action of the isolated Bag Man1 polypeptide in producing the desired product. Non-limiting examples of catalytic domains include: cellulases, hemicellulases such as xylanase, exo-mannanases, glucanases, arabinases, galactosidases, pectinases, and/or other activities such as proteases, lipases, acid phosphatases and/or others or functional fragments thereof. Fusion proteins are optionally linked to the isolated Bag Man1 polypeptide through a linker sequence that simply joins the Bag Man1 polypeptide and the fusion domain without significantly affecting the properties of either component, or the linker optionally has a functional importance for the intended application.

Alternatively, the isolated Bag Man1 polypeptides described herein are used in conjunction with one or more additional proteins of interest. Non-limiting examples of proteins of interest include: hemicellulases, exo-β-mannanases, alpha-galactosidases, beta-galactosidases, lactases, beta-glucanases, endo-beta-1,4-glucanases, cellulases, xylosidases, xylanases, xyloglucanases, xylan acetyl-esterases, galactanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases and/or other enzymes.

In other embodiments, the isolated Bag Man1 polypeptide is fused to a signal peptide for directing the extracellular secretion of the isolated Bag Man1 polypeptide. For example, in certain embodiments, the signal peptide is the native Bag Man1 signal peptide. In other embodiments, the signal peptide is a non-native signal peptide such as the *B. subtilis* AprE signal peptide. In some embodiments, the isolated Bag Man1 polypeptide has an N-terminal extension of Ala-Gly-Lys between the mature form and the signal peptide.

In some embodiments, the isolated Bag Man1 polypeptide is expressed in a heterologous organism, i.e., an organism other than *Bacillus agaradhaerens*. Exemplary heterologous organisms are Gram(+) bacteria such as *Bacillus subtilis, Bacillus licheniformis, Bacillus lentus, Bacillus brevis, Geobacillus* (formerly *Bacillus*) *stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans,* or *Streptomyces murinus*; Gram(−) bacteria such as *Escherichia coli*; yeast such as *Saccharomyces* spp. or *Schizosaccharomyces* spp., e.g. *Saccharomyces cerevisiae*; and filamentous fungi such as *Aspergillus* spp., e.g., *Aspergillus oryzae* or *Aspergillus niger*, and *Trichoderma reesei*. Methods from transforming nucleic acids into these organisms are well known in the art. A suitable procedure for transformation of *Aspergillus* host cells is described in EP 238 023.

In particular embodiments, the isolated Bag Man1 polypeptide is expressed in a heterologous organism as a secreted polypeptide, in which case, the compositions and method encompass a method for expressing a Bag Man1 polypeptide as a secreted polypeptide in a heterologous organism.

B. Bag Man1 Polynucleotides

Another aspect of the compositions and methods is a polynucleotide that encodes an isolated Bag Man1 polypeptide (including variants and fragments, thereof), provided in the context of an expression vector for directing the expression of a Bag Man1 polypeptide in a heterologous organism, such as those identified, herein. The polynucleotide that encodes a Bag Man1 polypeptide may be operably-linked to regulatory elements (e.g., a promoter, terminator, enhancer, and the like) to assist in expressing the encoded polypeptides.

An exemplary polynucleotide sequence encoding a Bag Man1 polypeptide has the nucleotide sequence of SEQ ID NO: 1. Similar, including substantially identical, polynucleotides encoding Bag Man1 polypeptides and variants may occur in nature, e.g., in other strains or isolates of *B. agaradhaerens*. In view of the degeneracy of the genetic code, it will be appreciated that polynucleotides having different nucleotide sequences may encode the same Bag Man1 polypeptides, variants, or fragments.

In some embodiments, polynucleotides encoding Bag Man1 polypeptides have a specified degree of amino acid sequence identity to the exemplified polynucleotide encoding a Bag Man1 polypeptide, e.g., at least 85%, at least 86%, at least 87%, at least 88%, at least 89%, at least 90%, at least 91%, at least 92%, at least 93%, at least 94%, at least 95%, at least 96%, at least 97%, at least 98%, or even at least 99% sequence identity to the amino acid sequence of SEQ ID NO:7. Homology can be determined by amino acid sequence alignment, e.g., using a program such as BLAST, ALIGN, or CLUSTAL, as described herein.

In some embodiments, the polynucleotide that encodes a Bag Man1 polypeptide is fused in frame behind (i.e., downstream of) a coding sequence for a signal peptide for directing the extracellular secretion of a Bag Man1 polypeptide. Heterologous signal sequences include those from bacterial cellulase genes. Expression vectors may be provided in a heterologous host cell suitable for expressing a Bag Man1 polypeptide, or suitable for propagating the expression vector prior to introducing it into a suitable host cell.

In some embodiments, polynucleotides encoding Bag Man1 polypeptides hybridize to the exemplary polynucleotide of SEQ ID NO:1 (or the complement thereof) under specified hybridization conditions. Exemplary conditions are stringent condition and highly stringent conditions, which are described, herein.

Bag Man1 polynucleotides may be naturally occurring or synthetic (i.e., man-made), and may be codon-optimized for expression in a different host, mutated to introduce cloning sites, or otherwise altered to add functionality.

C. Bag Man1 Vectors and Host Cells

In order to produce a disclosed Bag Man1 polypeptide, the DNA encoding the polypeptide can be chemically synthesized from published sequences or obtained directly from host cells harboring the gene (e.g., by cDNA library screening or PCR amplification). In some embodiments, the Bag Man1 polynucleotide is included in an expression cassette and/or cloned into a suitable expression vector by standard molecular cloning techniques. Such expression cassettes or vectors contain sequences that assist initiation and termination of transcription (e.g., promoters and terminators), and generally contain a selectable marker.

The expression cassette or vector is introduced in a suitable expression host cell, which then expresses the corresponding Bag Man1 polynucleotide. Particularly suitable expression hosts are bacterial expression host genera including *Escherichia* (e.g., *Escherichia coli*), *Pseudomonas* (e.g., *P. fluorescens* or *P. stutzerei*), *Proteus* (e.g., *Proteus mirabilis*), *Ralstonia* (e.g., *Ralstonia eutropha*), *Streptomyces*, *Staphylococcus* (e.g., *S. carnosus*), *Lactococcus* (e.g., *L. lactis*), or *Bacillus* (*subtilis*, *megaterium*, *licheniformis*, etc.). Also particularly suitable are yeast expression hosts such as *Saccharomyces cerevisiae*, *Schizosaccharomyces pombe*, *Yarrowia lipolytica*, *Hansenula polymorpha*, *Kluyveromyces lactis* or *Pichia pastoris*. Especially suited are fungal expression hosts such as *Aspergillus niger*, *Chrysosporium lucknowense*, *Aspergillus* (e.g., *A. oryzae*, *A. niger*, *A. nidulans*, etc.) or *Trichoderma reesei*. Also suited are mammalian expression hosts such as mouse (e.g., NS0), Chinese Hamster Ovary (CHO) or Baby Hamster Kidney (BHK) cell lines. Other eukaryotic hosts such as insect cells or viral expression systems (e.g., bacteriophages such as M13, T7 phage or Lambda, or viruses such as Baculovirus) are also suitable for producing the Bag Man1 polypeptide.

Promoters and/or signal sequences associated with secreted proteins in a particular host of interest are candidates for use in the heterologous production and secretion of endo-β-mannanases in that host or in other hosts. As an example, in filamentous fungal systems, the promoters that drive the genes for cellobiohydrolase I (cbh1), glucoamylase A (glaA), TAKA-amylase (amyA), xylanase (ex1A), the gpd-promoter cbh1, cbh11, endoglucanase genes EGI-EGV, Ce161B, Ce174A, egl1-egl5, gpd promoter, Pgk1, pki1, EF-1alpha, tef1, cDNA1 and hex1 are particularly suitable and can be derived from a number of different organisms (e.g., *A. niger*, *T. reesei*, *A. oryzae*, *A. awamori* and *A. nidulans*). In some embodiments, the Bag Man1 polynucleotide is recombinantly associated with a polynucleotide encoding a suitable homologous or heterologous signal sequence that leads to secretion of the Bag Man1 polypeptide into the extracellular (or periplasmic) space, thereby allowing direct detection of enzyme activity in the cell supernatant (or periplasmic space or lysate). Particularly suitable signal sequences for *Escherichia coli*, other Gram negative bacteria and other organisms known in the art include those that drive expression of the HlyA, DsbA, Pbp, PhoA, PelB, OmpA, OmpT or M13 phage Gill genes. For *Bacillus subtilis*, Gram-positive organisms and other organisms known in the art, particularly suitable signal sequences further include those that drive expression of the AprE, NprB, Mpr, AmyA, AmyE, Blac, SacB, and for *S. cerevisiae* or other yeast, include the killer toxin, Bar1, Suc2, Mating factor alpha, Inu1A or Ggp1p signal sequence. Signal sequences can be cleaved by a number of signal peptidases, thus removing them from the rest of the expressed protein. In some embodiments, the rest of the Bag Man1 polypeptide is expressed alone or as a fusion with other peptides, tags or proteins located at the N- or C-terminus (e.g., 6×His, HA or FLAG tags). Suitable fusions include tags, peptides or proteins that facilitate affinity purification or detection (e.g., BCE103, 6×His, HA, chitin binding protein, thioredoxin or FLAG tags), as well as those that facilitate expression, secretion or processing of the target endo-β-mannanase. Suitable processing sites include enterokinase, STE13, Kex2 or other protease cleavage sites for cleavage in vivo or in vitro.

Bag Man1 polynucleotides are introduced into expression host cells by a number of transformation methods including, but not limited to, electroporation, lipid-assisted transformation or transfection ("lipofection"), chemically mediated transfection (e.g., CaCl and/or CaP), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

Alternatively, the Bag Man1 polypeptides are expressed intracellularly. Optionally, after intracellular expression of the enzyme variants, or secretion into the periplasmic space using signal sequences such as those mentioned above, a permeabilisation or lysis step can be used to release the Bag Man1 polypeptide into the supernatant. The disruption of the membrane barrier is effected by the use of mechanical means such as ultrasonic waves, pressure treatment (French press), cavitation or the use of membrane-digesting enzymes such as lysozyme or enzyme mixtures. As a further alternative, the polynucleotides encoding the Bag Man1 polypeptide are expressed by use of a suitable cell-free expression system. In cell-free systems, the polynucleotide of interest is typically transcribed with the assistance of a promoter, but ligation to form a circular expression vector is optional. In other embodiments, RNA is exogenously added or generated without transcription and translated in cell free systems.

IV. Activities of Bag Man1

The isolated Bag Man1 polypeptides disclosed herein may have enzymatic activity over a broad range of pH conditions. In certain embodiments the disclosed Bag Man1 polypeptides have enzymatic activity from about pH 4.5 to about pH 11.0. In preferred embodiments, the Bag Man1 polypeptides have substantial enzymatic activity from about pH 4.5 to about pH 8.5. It should be noted that the pH values described herein may vary by ±0.2. For example a pH value of about 8.0 could vary from pH 7.8 to pH 8.2.

The isolated Bag Man1 polypeptides disclosed herein may have enzymatic activity over a wide range of temperatures, e.g., from 35° C. or lower to about 75° C. In certain embodiments, the Bag Man1 polypeptides have substantial enzymatic activity at a temperature range of about 40° C. to about 55° C. It should be noted that the temperature values described herein may vary by ±0.2° C. For example a temperature of about 50° C. could vary from 49.8° C. to 50.2° C.

As shown in Example 6, the Bag Man1 polypeptide had endo-β-mannanase activity against locust bean gum and guar gum in the presence of proteases. Moreover, the endo-β-mannanase activity of the Bag Man1 polypeptide was at least as effective as, and in some cases more effective than, a commercial benchmark endo-β-mannanase in hydrolyzing mannans such as locust bean gum and guar gum (Tables 6-1 and 6-2). In fact, Bag Man1 showed hydrolysis activity against exemplary gum stained material, in the presence of both powder and liquid detergent (Example 6). Accordingly, in certain embodiments, any of the isolated Bag Man1 polypeptides described herein may hydrolyze mannan substrates that include, but are not limited to, locust bean gum, guar gum, and combinations thereof.

V. Detergent Compositions Comprising a Bag Man1 Polypeptide

An aspect of the compositions and methods disclosed herein is a detergent composition comprising an isolated Bag Man1 polypeptide (including variants or fragments, thereof) and methods for using such compositions in cleaning applications. Cleaning applications include, but are not limited to, laundry or textile cleaning, laundry or textile softening, dishwashing (manual and automatic), stain pre-treatment, and the like. Particular applications are those where mannans (e.g., locust bean gum, guar gum, etc.) are a component of the soils or stains to be removed. Detergent compositions typically include an effective amount of any of the Bag Man1 polypeptides described herein, e.g., at least 0.0001 weight percent, from about 0.0001 to about 1, from about 0.001 to about 0.5, from about 0.01 to about 0.1 weight percent, or even from about 0.1 to about 1 weight percent, or more. An effective amount of a Bag Man1 polypeptide in the detergent composition results in the Bag Man1 polypeptide having enzymatic activity sufficient to hydrolyze a mannan-containing substrate, such as locust bean gum, guar gum, or combinations thereof.

Additionally, detergent compositions having a concentration from about 0.4 g/L to about 2.2 g/L, from about 0.4 g/L to about 2.0 g/L, from about 0.4 g/L to about 1.7 g/L, from about 0.4 g/L to about 1.5 g/L, from about 0.4 g/L to about 1 g/L, from about 0.4 g/L to about 0.8 g/L, or from about 0.4 g/L to about 0.5 g/L may be mixed with an effective amount of an isolated Bag Man1 polypeptide. The detergent composition may also be present at a concentration of about 0.4 ml/L to about 2.6 ml/L, from about 0.4 ml/L to about 2.0 ml/L, from about 0.4 ml/L to about 1.5 m/L, from about 0.4 ml/L to about 1 ml/L, from about 0.4 ml/L to about 0.8 ml/L, or from about 0.4 ml/L to about 0.5 ml/L.

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. In the exemplified detergent compositions, the enzymes levels are expressed by pure enzyme by weight of the total composition and unless otherwise specified, the detergent ingredients are expressed by weight of the total compositions.

In some embodiments, the detergent composition comprises one or more surfactants, which may be non-ionic, semi-polar, anionic, cationic, zwitterionic, or combinations and mixtures thereof. The surfactants are typically present at a level of from about 0.1% to 60% by weight. Exemplary surfactants include but are not limited to sodium dodecylbenzene sulfonate, C12-14 pareth-7, C12-15 pareth-7, sodium C12-15 pareth sulfate, C14-15 pareth-4, sodium laureth sulfate (e.g., Steol CS-370), sodium hydrogenated cocoate, C12 ethoxylates (Alfonic 1012-6, Hetoxol LA7, Hetoxol LA4), sodium alkyl benzene sulfonates (e.g., Nacconol 90G), and combinations and mixtures thereof.

Anionic surfactants that may be used with the detergent compositions described herein include but are not limited to linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. It may also contain 0-40% of nonionic surfactant such as alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, polyhydroxy alkyl fatty acid amide (e.g., as described in WO 92/06154), and combinations and mixtures thereof.

Nonionic surfactants that may be used with the detergent compositions described herein include but are not limited to polyoxyethylene esters of fatty acids, polyoxyethylene sorbitan esters (e.g., TWEENs), polyoxyethylene alcohols, polyoxyethylene isoalcohols, polyoxyethylene ethers (e.g., TRITONs and BRIJ), polyoxyethylene esters, polyoxyethylene-p-tert-octylphenols or octylphenyl-ethylene oxide condensates (e.g., NONIDET P40), ethylene oxide condensates with fatty alcohols (e.g., LUBROL), polyoxyethylene nonylphenols, polyalkylene glycols (SYNPERONIC F108), sugar-based surfactants (e.g., glycopyranosides, thioglycopyranosides), and combinations and mixtures thereof.

The detergent compositions disclosed herein may have mixtures that include, but are not limited to 5-15% anionic surfactants, <5% nonionic surfactants, cationic surfactants, phosphonates, soap, enzymes, perfume, butylphenyl methylpropionate, geraniol, zeolite, polycarboxylates, hexyl cinnamal, limonene, cationic surfactants, citronellol, and benzisothiazolinone.

Detergent compositions may additionally include one or more detergent builders or builder systems, a complexing agent, a polymer, a bleaching system, a stabilizer, a foam booster, a suds suppressor, an anti-corrosion agent, a soil-suspending agent, an anti-soil redeposition agent, a dye, a bactericide, a hydrotope, a tarnish inhibitor, an optical brightener, a fabric conditioner, and a perfume. The detergent compositions may also include enzymes, including but not limited to proteases, amylases, cellulases, lipases, pectin degrading enzymes, xyloglucanases, or additional carboxylic ester hydrolases. The pH of the detergent compositions should be neutral to basic, as described herein.

In some embodiments incorporating at least one builder, the detergent compositions comprise at least about 1%, from about 3% to about 60% or even from about 5% to about 40% builder by weight of the cleaning composition. Builders may include, but are not limited to, the alkali metals, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metals, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present disclosure.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present disclosure, including those known in the art (See, e.g., EP 2 100 949).

As indicated herein, in some embodiments, the cleaning compositions described herein further comprise adjunct materials including, but not limited to surfactants, builders, bleaches, bleach activators, bleach catalysts, other enzymes, enzyme stabilizing systems, chelants, optical brighteners, soil release polymers, dye transfer agents, dispersants, suds suppressors, dyes, perfumes, colorants, filler salts, hydrotropes, photoactivators, fluorescers, fabric conditioners, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See, e.g., U.S. Pat. Nos. 6,610,642; 6,605,458; 5,705,464; 5,710,115; 5,698,504; 5,695,679; 5,686,014; and 5,646,101; all of which are incorporated herein by reference). Embodiments of specific cleaning composition materials are exemplified in detail below. In embodiments in which the cleaning adjunct materials are not compatible with the Bag Man1 variants in the cleaning compositions, suitable methods of keeping the cleaning adjunct materials and the endo-β-mannanase(s) separated (i.e., not in contact with each other), until combination of the two components is appropriate, are used. Such separation methods include any suitable method known in the art (e.g., gelcaps, encapsulation, tablets, physical separation, etc.).

The cleaning compositions described herein are advantageously employed for example, in laundry applications, hard surface cleaning, dishwashing applications, as well as cosmetic applications such as dentures, teeth, hair, and skin. In addition, due to the unique advantages of increased effectiveness in lower temperature solutions, the Bag Man1 enzymes described herein are ideally suited for laundry and fabric softening applications. Furthermore, the Bag Man1 enzymes may find use in granular and liquid compositions.

The isolated Bag Man1 polypeptides described herein may also find use cleaning in additive products. In some embodiments, low temperature solution cleaning applications find use. In some embodiments, the present disclosure provides cleaning additive products including at least one disclosed Bag Man1 polypeptide is ideally suited for inclusion in a wash process when additional bleaching effectiveness is desired. Such instances include, but are not limited to low temperature solution cleaning applications. In some embodiments, the additive product is in its simplest form, one or more endo-β-mannanases. In some embodiments, the additive is packaged in dosage form for addition to a cleaning process. In some embodiments, the additive is packaged in dosage form for addition to a cleaning process where a source of peroxygen is employed and increased bleaching effectiveness is desired. Any suitable single dosage unit form finds use with the present disclosure, including but not limited to pills, tablets, gelcaps, or other single dosage units such as pre-measured powders or liquids. In some embodiments, filler(s) or carrier material(s) are included to increase the volume of such compositions. Suitable filler or carrier materials include, but are not limited to various salts of sulfate, carbonate, and silicate as well as talc, clay, and the like. Suitable filler or carrier materials for liquid compositions include, but are not limited to water or low molecular weight primary and secondary alcohols including polyols and diols. Examples of such alcohols include, but are not limited to methanol, ethanol, propanol, and isopropanol. In some embodiments, the compositions contain from about 5% to about 90% of such materials. Acidic fillers find use to reduce pH. Alternatively, in some embodiments, the cleaning additive includes adjunct ingredients, as described more fully below.

The present cleaning compositions and cleaning additives require an effective amount of at least one of the Bag Man1 polypeptides described herein, alone or in combination with other endo-β-mannanases and/or additional enzymes. In certain embodiments, the additional enzymes include, but are not limited to, at least one enzyme selected from proteases, peroxidases, cellulases (endoglucanases), beta-glucanases, hemicellulases, lipases, phospholipases, esterases, eroxidases, laccases, amalyases, alpha-amylases, glucoamylases, cutinases, pectinases, pectate lyases, keratinases, reductases, oxidases, phenoloxidases, lipoxygenases, ligninases, pullulanases, tannases, pentosanases, malanases, arabinosidases, hyaluronidases, chondroitinases, laccases, xyloglucanases, xylanases, pectin acetyl esterases, polygalacturonases, rhamnogalacturonases, pectin lyases, other endo-β-mannanases, exo-β-mannanases pectin methylesterases, cellobiohydrolases, and transglutaminases, and mixtures thereof.

The required level of enzyme is achieved by the addition of one or more disclosed Bag Man1 polypeptide. Typically the present cleaning compositions will comprise at least about 0.0001 weight percent, from about 0.0001 to about 10, from about 0.001 to about 1, or even from about 0.01 to about 0.1 weight percent of at least one of the disclosed Bag Man1 polypeptides.

The cleaning compositions herein are typically formulated such that, during use in aqueous cleaning operations, the wash water will have a pH of from about 3.0 to about 11. Liquid product formulations are typically formulated to have a neat pH from about 5.0 to about 9.0. Granular laundry products are typically formulated to have a pH from about 8.0 to about 11.0. Techniques for controlling pH at recommended usage levels include the use of buffers, alkalis, acids, etc., and are well known to those skilled in the art.

Suitable low pH cleaning compositions typically have a neat pH of from about 3.0 to about 5.0 or even from about 3.5 to about 4.5. Low pH cleaning compositions are typically free of surfactants that hydrolyze in such a pH environment. Such surfactants include sodium alkyl sulfate surfactants that comprise at least one ethylene oxide moiety or even from about 1 to about 16 moles of ethylene oxide. Such cleaning compositions typically comprise a sufficient amount of a pH modifier, such as sodium hydroxide, monoethanolamine, or hydrochloric acid, to provide such cleaning composition with a neat pH of from about 3.0 to about 5.0. Such compositions typically comprise at least one acid stable enzyme. In some embodiments, the compositions are liquids, while in other embodiments, they are solids. The pH of such liquid compositions is typically measured as a neat pH. The pH of such solid compositions is measured as a 10% solids solution of the composition wherein the solvent is distilled water. In these embodiments, all pH measurements are taken at 20° C., unless otherwise indicated.

Suitable high pH cleaning compositions typically have a neat pH of from about 9.0 to about 11.0, or even a net pH of from 9.5 to 10.5. Such cleaning compositions typically comprise a sufficient amount of a pH modifier, such as sodium hydroxide, monoethanolamine, or hydrochloric acid, to provide such cleaning composition with a neat pH of from about 9.0 to about 11.0. Such compositions typically comprise at least one base-stable enzyme. In some embodiments, the compositions are liquids, while in other embodiments, they are solids. The pH of such liquid compositions is typically measured as a neat pH. The pH of such solid compositions is measured as a 10% solids solution of said composition wherein the solvent is distilled water. In these embodiments, all pH measurements are taken at 20° C., unless otherwise indicated.

In some embodiments, when the Bag Man1 polypeptide is employed in a granular composition or liquid, it is desirable for the Bag Man1 polypeptide to be in the form of an encapsulated particle to protect the Bag Man1 polypeptide from other components of the granular composition during storage. In addition, encapsulation is also a means of controlling the availability of the Bag Man1 polypeptide during the cleaning process. In some embodiments, encapsulation enhances the performance of the Bag Man1 polypeptide and/or additional enzymes. In this regard, the Bag Man1 polypeptides of the present disclosure are encapsulated with any suitable encapsulating material known in the art. In some embodiments, the encapsulating material typically encapsulates at least part of the catalyst for the Bag Man1 polypeptides described herein. Typically, the encapsulating material is water-soluble and/or water-dispersible. In some embodiments, the encapsulating material has a glass transition temperature (Tg) of 0° C. or higher. Glass transition temperature is described in more detail in the PCT application WO 97/11151. The encapsulating material is typically selected from consisting of carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some typical embodiments, the encapsulating material is a starch (See, e.g., EP 0 922 499; U.S. Pat. No. 4,977,252; U.S. Pat. No. 5,354,559; and U.S. Pat. No. 5,935,826). In some embodiments, the encapsulating material is a microsphere made from plastic such as thermoplastics, acrylonitrile, methacrylonitrile, polyacrylonitrile, polymethacrylonitrile, and mixtures thereof; commercially available microspheres that find use include, but are not limited to those supplied by EXPANCEL® (Stockviksverken, Sweden), and PM 6545, PM 6550, PM 7220, PM 7228, EXTENDOSPHERES®, LUXSIL®, Q-CEL®, and SPHERICEL® (PQ Corp., Valley Forge, Pa.).

The term "granular composition" refers to a conglomeration of discrete solid, macroscopic particles. Powders are a special class of granular material due to their small particle size, which makes them more cohesive and more easily suspended.

In using detergent compositions that include Bag Man1 in cleaning applications, the fabrics, textiles, dishes, or other surfaces to be cleaned are incubated in the presence of the Bag Man1 detergent composition for a time sufficient to allow Bag Man1 to hydrolyze mannan substrates including, but not limited to, locust bean gum, guar gum, and combinations thereof present in soil or stains, and then typically rinsed with water or another aqueous solvent to remove the Bag Man1 detergent composition along with hydrolyzed mannans.

As described herein, the Bag Man1 polypeptides find particular use in the cleaning industry, including, but not limited to laundry and dish detergents. These applications place enzymes under various environmental stresses. The Bag Man1 polypeptides may provide advantages over many currently used enzymes, due to their stability under various conditions.

Indeed, there are a variety of wash conditions including varying detergent formulations, wash water volumes, wash water temperatures, and lengths of wash time, to which endo-β-mannanases involved in washing are exposed. In addition, detergent formulations used in different geographical areas have different concentrations of their relevant components present in the wash water. For example, European detergents typically have about 4500-5000 ppm of detergent components in the wash water, while Japanese detergents typically have approximately 667 ppm of detergent components in the wash water. In North America, particularly the United States, detergents typically have about 975 ppm of detergent components present in the wash water.

A low detergent concentration system includes detergents where less than about 800 ppm of the detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of the detergent components are present in the wash water. North American detergents are generally considered to be medium detergent concentration systems as they have approximately 975 ppm of detergent components present in the wash water.

Brazil typically has approximately 1500 ppm of detergent components present in the wash water.

A high detergent concentration system includes detergents where greater than about 2000 ppm of the detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. As mentioned above, Brazil typically has approximately 1500 ppm of detergent components present in the wash water. However, other high suds phosphate builder detergent geographies, not limited to other Latin American countries, may have high detergent concentration systems up to about 6000 ppm of detergent components present in the wash water.

In light of the foregoing, it is evident that concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

The concentrations of the typical wash solutions are determined empirically. For example, in the U.S., a typical washing machine holds a volume of about 64.4 L of wash solution. Accordingly, in order to obtain a concentration of about 975 ppm of detergent within the wash solution about 62.79 g of detergent composition must be added to the 64.4 L of wash solution. This amount is the typical amount measured into the wash water by the consumer using the measuring cup provided with the detergent.

As a further example, different geographies use different wash temperatures. The temperature of the wash water in Japan is typically less than that used in Europe. For example, the temperature of the wash water in North America and Japan is typically between about 10 and about 30° C. (e.g., about 20° C.), whereas the temperature of wash water in Europe is typically between about 30 and about 60° C. (e.g., about 40° C.). Accordingly, in certain embodiments, the detergent compositions described herein may be utilized at temperature from about 10° C. to about 60° C., or from about 20° C. to about 60° C., or from about 30° C. to about 60° C., or from about 40° C. to about 60° C., as well as all other combinations within the range of about 40° C. to about 55° C., and all ranges within 10° C. to 60° C. However, in the interest of saving energy, many consumers are switching to using cold water washing. In addition, in some further regions, cold water is typically used for laundry, as well as dish washing applications. In some embodiments, the "cold water washing" of the present disclosure utilizes washing at temperatures from about 10° C. to about 40° C., or from about 20° C. to about 30° C., or from about 15° C. to about 25° C., as well as all other combinations within the range of about 15° C. to about 35° C., and all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm # divided by 17.1 equals grains per gallon) of hardness minerals.

TABLE II

Water Hardness Levels

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

Accordingly, in some embodiments, the present disclosure provides Bag Man1 polypeptides that show surprising wash performance in at least one set of wash conditions (e.g., water temperature, water hardness, and/or detergent concentration). In some embodiments, the Bag Man1 polypeptides are comparable in wash performance to other endo-β-mannanases. In some embodiments, the Bag Man1 polypeptides exhibit enhanced wash performance as compared to endo-β-mannanases currently commercially available. Thus, in some preferred embodiments, the Bag Man1 polypeptides provided herein exhibit enhanced oxidative stability, enhanced thermal stability, enhanced cleaning capabilities under various conditions, and/or enhanced chelator stability. In addition, the Bag Man1 polypeptides may find use in cleaning compositions that do not include detergents, again either alone or in combination with builders and stabilizers.

In some embodiments of the present disclosure, the cleaning compositions comprise at least one Bag Man1 polypeptide of the present disclosure at a level from about 0.00001% to about 10% by weight of the composition and the balance (e.g., about 99.999% to about 90.0%) comprising cleaning adjunct materials by weight of composition. In other aspects of the present disclosure, the cleaning compositions comprises at least one Bag Man1 polypeptide at a level of about 0.0001% to about 10%, about 0.001% to about 5%, about 0.001% to about 2%, about 0.005% to about 0.5% by weight of the composition and the balance of the cleaning composition (e.g., about 99.9999% to about 90.0%, about 99.999% to about 98%, about 99.995% to about 99.5% by weight) comprising cleaning adjunct materials.

In addition to the Bag Man1 polypeptides provided herein, any other suitable endo-β-mannanases find use in the compositions of the present disclosure. Suitable endo-β-mannanases include, but are not limited to, endo-β-mannanases of the GH26 family of glycosyl hydrolases, endo-β-mannanases of the GH5 family of glycosyl hydrolases, acidic endo-β-mannanases, neutral endo-β-mannanases, and alkaline endo-β-mannanases. Examples of alkaline endo-β-mannanases include those described in U.S. Pat. Nos. 6,060,299, 6,566, 114, and 6,602,842; WO 9535362A1, WO 9964573A1, and WO9964619A1. Additionally, suitable endo-β-mannanases include, but are not limited to those of animal, plant, fungal, or bacterial origin. Chemically or genetically modified mutants are encompassed by the present disclosure.

Examples of useful endo-β-mannanases include *Bacillus* endo-β-mannanases such as *B. subtilis* endo-β-mannanase (See, e.g., U.S. Pat. No. 6,060,299, and WO 9964573A1), *B.* sp. 1633 endo-β-mannanase (See, e.g., U.S. Pat. No. 6,566,114 and WO9964619A1), *Bacillus* sp. AAI12 endo-β-mannanase (See, e.g., U.S. Pat. No. 6,566,114 and WO9964619A1), *B.* sp. AA349 endo-β-mannanase (See, e.g., U.S. Pat. No. 6,566,114 and WO9964619A1), *B. agaradhaerens* NCIMB 40482 endo-β-mannanase (See, e.g., U.S. Pat. No. 6,566,114 and WO9964619A1), *B. halodurans* endo-β-mannanase, *B. clausii* endo-β-mannanase (See, e.g., U.S. Pat. No. 6,566,114 and WO9964619A1), *B. licheniformis* endo-β-mannanase (See, e.g., U.S. Pat. No. 6,566,114 and WO9964619A1), *Humicola* endo-β-mannanases such as *H. insolens* endo-β-mannanase (See, e.g., U.S. Pat. No. 6,566,114 and WO9964619A1), and *Caldocellulosiruptor* endo-β-mannanases such as *C.* sp. endo-β-mannanase (See, e.g., U.S. Pat. No. 6,566,114 and WO9964619A1).

Furthermore, a number of identified mannanases (i.e., endo-β-mannanases and exo-(3-mannanases) find use in some embodiments of the present disclosure, including but not limited to *Agaricus bisporus* mannanase (See, Tang et al., [2001] *Appl. Environ. Microbiol.* 67: 2298-2303), *Aspergillu tamarii* mannanase (See, Civas et al., [1984] *Biochem. J.* 219: 857-863), *Aspergillus aculeatus* mannanase (See, Christgau et al., [1994] *Biochem. Mol. Biol. Int.* 33: 917-925), *Aspergillus awamori* mannanase (See, Setati et al., [2001] *Protein Express Purif.* 21: 105-114), *Aspergillus fumigatus* mannanase (See, Puchart et al., [2004] *Biochimica et biophysica Acta.* 1674: 239-250), *Aspergillus niger* mannanase (See, Ademark et al., [1998] *J. Biotechnol.* 63: 199-210), *Aspergillus oryzae* NRRL mannanase (See, Regalado et al., [2000] *J. Sci. Food Agric.* 80: 1343-1350), *Aspergillus sulphureus* mannanase (See, Chen et al., [2007] *J. Biotechnol.* 128(3): 452-461), *Aspergillus terrus* mannanase (See, Huang et al., [2007] *Wei Sheng Wu Xue Bao.* 47(2): 280-284), *Bacillus agaradhaerens* mannanase (See, U.S. Pat. No. 6,376,445), *Bacillus* AM001 mannanase (See, Akino et al., [1989] Arch. Microbiol. 152: 10-15), *Bacillus brevis* mannanase (See, Araujo and Ward, [1990] *J. Appl. Bacteriol.* 68: 253-261), *Bacillus circulans* K-1 mannanase (See, Yoshida et al., [1998] *Biosci. Biotechnol. Biochem.* 62(3): 514-520), *Bacillus polymyxa* mannanase (See, Araujo and Ward, [1990] *J. Appl. Bacteriol.* 68: 253-261), *Bacillus* sp JAMB-750 mannanase (See, Hatada et al., [2005] Extremophiles. 9: 497-500), *Bacillus* sp. M50 mannanase (See, Chen et al., [2000] *Wei Sheng Wu Xue Bao.* 40: 62-68), *Bacillus* sp. N 16-5 mannanase (See, Yanhe et al., [2004]*Extremophiles* 8: 447-454), *Bacillus stearothermophilu* mannanase (See, Talbot and Sygusch, [1990] *Appl. Environ. Microbiol.* 56: 3505-3510), *Bacillus subtilis* mannanase (See, Mendoza et al., [1994] *World J. Microbiol. Biotechnol.* 10: 51-54), *Bacillus subtilis* B36 mannanase (Li et al., [2006] *Z Naturforsch (C).* 61: 840-846), *Bacillus subtilis* BM9602 mannanase (See, Cui et al., [1999] *Wei Sheng Wu Xue Bao.* 39(1): 60-63), *Bacillus subtilis* SA-22 mannanase (See, Sun et al., [2003] *Sheng Wu Gong Cheng Xue Bao.* 19(3): 327-330), *Bacillus subtilis*168 mannanase (See, Helow and Khattab, [1996] *Acta Microbiol. Immunol. Hung.* 43: 289-299), *Bacteroides ovatus* mannanase (See, Gherardini et al., [1987] *J. Bacteriol.* 169: 2038-2043), *Bacteroides ruminicola* mannanase (See, Matsushita et al., [1991] *J. Bacteriol.* 173: 6919-6926), *Caldibacillus cellulovorans* mannanase (See, Sunna et al., [2000] *Appl. Environ. Microbiol.* 66: 664-670), *Caldocellulosiruptor saccharolyticus* mannanase (See, Morris et al., [1995] *Appl. Environ. Microbiol.* 61: 2262-2269), *Caldocellum saccharolyticum* mannanase (See, Bicho et al., [1991] *Appl. Microbiol. Biotechnol.* 36: 337-343), *Cellulomonas fimi* mannanase (See, Stoll et al., [1999] *Appl. Environ. Microbiol.* 65(6): 2598-2605), *Clostridium butyricum/beijerinckii* mannanase (See, Nakajima and Matsuura, [1997] *Biosci. Biotechnol. Biochem.* 61: 1739-1742), *Clostridium cellulolyticum* mannanase (See, Perret et al., [2004] *Biotechnol. Appl. Biochem.* 40: 255-259), *Clostridium tertium* mannanase (See, Kataoka and Tokiwa, [1998] *J. Appl. Microbiol.* 84: 357-367), *Clostridium thermocellum* mannanase (See, Halstead et al., [1999] *Microbiol.* 145: 3101-3108), *Dictyoglomus thermophilum* mannanase (See, Gibbs et al., [1999] *Curr. Microbiol.* 39(6): 351-357), *Flavobacterium* sp mannanase (See, Zakaria et al., [1998] *Biosci. Biotechnol. Biochem.* 62: 655-660), *Gastropoda pulmonata* mannanase (See, Charrier and Rouland, [2001] *J. Expt. Zool.* 290: 125-135), *Littorina brevicula* mannanase (See, Yamamura et al., [1996] *Biosci. Biotechnol. Biochem.* 60: 674-676), *Lycopersicon esculentum* mannanase (See, Filichkin et al., [2000] *Plant Physiol.* 134: 1080-1087), *Paenibacillus curdlanolyticus* mannanase (See, Pason and Ratanakhanokchai, [2006] *Appl. Environ. Microbiol.* 72: 2483-2490), *Paenibacillus polymyxa* mannanase (See, Han et al., [2006] *Appl. Microbiol Biotechnol.* 73(3): 618-630), *Phanerochaete chrysosporium* mannanase (See, Wymelenberg et al., [2005] *J. Biotechnol.* 118: 17-34), *Piromyces* sp. mannanase (See, Fanutti et al., [1995] *J. Biol. Chem.* 270(49): 29314-29322), *Pomacea insulars* mannanase (See, Yamamura et al., [1993] *Biosci. Biotechnol. Biochem.* 7: 1316-1319), *Pseudomonas fluorescens* subsp. Cellulose mannanase (See, Braithwaite et al., [1995] *Biochem J.* 305: 1005-1010), *Rhodothermus marinus* mannanase (See, Politz et al., [2000] *Appl. Microbiol. Biotechnol.* 53 (6): 715-721), *Sclerotium rolfsii* mannanase (See, Sachslehner et al., [2000] *J. Biotechnol.* 80:127-134), *Streptomyces galbus* mannanase (See, Kansoh and Nagieb, [2004] *Anton. van. Leeuwonhoek.* 85: 103-114), *Streptomyces lividans* mannanase (See, Arcand et al., [1993] *J. Biochem.* 290: 857-863), *Thermoanaerobacterium Polysaccharolyticum* mannanase (See, Cann et al., [1999] *J. Bacteriol.* 181: 1643-1651), *Thermomonospora fusca* mannanase (See, Hilge et al., [1998] *Structure* 6: 1433-1444), *Thermotoga maritima* mannanase (See, Parker et al., [2001] *Biotechnol. Bioeng.* 75(3): 322-333), *Thermotoga neapolitana* mannanase (See, Duffaud et al., [1997] *Appl. Environ. Microbiol.* 63: 169-177), *Trichoderma harzanium* strain T4 mannanase (See, Franco et al., [2004] *Biotechnol Appl. Biochem.* 40: 255-259), *Trichoderma reesei* mannanase (See, Stalbrand et al., [1993] *J. Biotechnol.* 29: 229-242), and *Vibrio* sp. mannanase (See, Tamaru et al., [1997] *J. Ferment. Bioeng.* 83: 201-205).

Additional suitable endo-β-mannanases include commercially available endo-β-mannanases such as HEMICELL® (Chemgen); GAMANASE® and MANNAWAY®, (Novozymes A/S, Denmark); PURABRITE™ and MANNASTAR™ (Genencor, A Danisco Division, Palo Alto, Calif.); and PYROLASE® 160 and PYROLASE® 200 (Diversa).

In some embodiments of the present disclosure, the cleaning compositions of the present disclosure further comprise endo-β-mannanases at a level from about 0.00001% to about 10% of additional endo-β-mannanase by weight of the composition and the balance of cleaning adjunct materials by weight of composition. In other aspects of the present disclosure, the cleaning compositions of the present disclosure also comprise endo-β-mannanases at a level of about 0.0001% to about 10%, about 0.001% to about 5%, about 0.001% to about 2%, about 0.005% to about 0.5% endo-β-mannanase by weight of the composition.

In some embodiments of the present disclosure, any suitable protease may be used. Suitable proteases include those of animal, vegetable or microbial origin. In some embodiments, chemically or genetically modified mutants are included. In some embodiments, the protease is a serine protease, preferably an alkaline microbial protease or a trypsin-like protease. Various proteases are described in PCT applications WO 95/23221 and WO 92/21760; U.S. Pat. Publication No. 2008/0090747; and U.S. Pat. Nos. 5,801,039; 5,340,735; 5,500,364; 5,855,625; U.S. RE 34,606; U.S. Pat. Nos. 5,955,340; 5,700,676; 6,312,936; 6,482,628; and various other patents. In some further embodiments, metalloproteases find use in the present disclosure, including but not limited to the neutral metalloprotease described in PCT application WO 07/044,993. Commercially available proteases that find use in the present disclosure include, but are not limited to PURAFECT®, PURAFECT® PRIME, and PROPERASE® (Genencor, A Danisco Division, Palo Alto, Calif.). Additionally, commercially available proteases that find use in the present disclosure include, but are not limited to ALCALASE®, EVERLASE®, LIQUINASE®, POLARZYME®, OVOZYME® and SAVINASE® (Novozymes A/S, Denmark).

In some embodiments of the present disclosure, any suitable amylase may be used. In some embodiments, any amylase (e.g., alpha and/or beta) suitable for use in alkaline solutions also find use. Suitable amylases include, but are not limited to those of bacterial or fungal origin. Chemically or genetically modified mutants are included in some embodiments. Amylases that find use in the present disclosure include, but are not limited to α-amylases obtained from *B. licheniformis* (See, e.g., GB 1,296,839). Commercially available amylases that find use in the present disclosure include, but are not limited to DURAMYL®, TERMAMYL®, FUNGAMYL®, STAINZYME®, STAINZYME PLUS®, STAINZYME ULTRA®, and BAN™ (Novozymes A/S, Denmark), as well as PURASTAR®, POWERASE™, RAPIDASE®, and MAXAMYL® P (Genencor, A Danisco Division, Palo Alto, Calif.).

In some embodiments of the present disclosure, the disclosed cleaning compositions further comprise amylases at a level from about 0.00001% to about 10% of additional amylase by weight of the composition and the balance of cleaning adjunct materials by weight of composition. In other aspects of the present disclosure, the cleaning compositions also comprise amylases at a level of about 0.0001% to about 10%, about 0.001% to about 5%, about 0.001% to about 2%, about 0.005% to about 0.5% amylase by weight of the composition.

In some embodiments of the present disclosure, any suitable pectin degrading enzyme may be used. As used herein, "pectin degrading enzyme(s)" encompass arabinanase (EC 3.2.1.99), galactanases (EC 3.2.1.89), polygalacturonase (EC 3.2.1.15) exo-polygalacturonase (EC 3.2.1.67), exo-poly-alpha-galacturonidase (EC 3.2.1.82), pectin lyase (EC 4.2.2.10), pectin esterase (EC 3.1.1.11), pectate lyase (EC 4.2.2.2), exo-polygalacturonate lyase (EC 4.2.2.9) and hemicellulases such as endo-1,3-β-xylosidase (EC 3.2.1.32), xylan-1,4-β-xylosidase (EC 3.2.1.37) and α-L-arabinofuranosidase (EC 3.2.1.55). Pectin degrading enzymes are natural mixtures of the above mentioned enzymatic activities. Pectin enzymes therefore include the pectin methylesterases which hydrolyse the pectin methyl ester linkages, polygalacturonases which cleave the glycosidic bonds between galacturonic acid molecules, and the pectin transeliminases or lyases which act on the pectic acids to bring about non-hydrolytic cleavage of α-1,4 glycosidic linkages to form unsaturated derivatives of galacturonic acid.

Suitable pectin degrading enzymes include those of plant, fungal, or microbial origin. In some embodiments, chemically or genetically modified mutants are included. In some embodiments, the pectin degrading enzymes are alkaline pectin degrading enzymes, i.e., enzymes having an enzymatic activity of at least 10%, preferably at least 25%, more preferably at least 40% of their maximum activity at a pH of from about 7.0 to about 12. In certain other embodiments, the pectin degrading enzymes are enzymes having their maximum activity at a pH of from about 7.0 to about 12. Alkaline pectin degrading enzymes are produced by alkalophilic microorganisms e.g., bacterial, fungal, and yeast microorganisms such as *Bacillus* species. In some embodiments, the microorganisms are *Bacillus firmus, Bacillus circulans*, and *Bacillus subtilis* as described in JP 56131376 and JP 56068393. Alkaline pectin decomposing enzymes may include but are not limited to galacturn-1,4-α-galacturonase (EC 3.2.1.67), poly-galacturonase activities (EC 3.2.1.15, pectin esterase (EC 3.1.1.11), pectate lyase (EC 4.2.2.2) and their iso enzymes. Alkaline pectin decomposing enzymes can be produced by the *Erwinia* species. In some embodiments, the alkaline pectin decomposing enzymes are produced by *E. chrysanthemi, E. carotovora, E. amylovora, E. herbicola*, and *E. dissolvens* as described in JP 59066588, JP 63042988, and in *World J. Microbiol. Microbiotechnol*. (8, 2, 115-120) 1992. In certain other embodiments, the alkaline pectin enzymes are produced by *Bacillus* species as disclosed in JP 73006557 and Agr. Biol. Chem. (1972), 36 (2) 285-93.

In some embodiments of the present disclosure, the disclosed cleaning compositions further comprise pectin degrading enzymes at a level from about 0.00001% to about 10% of additional pectin degrading enzyme by weight of the composition and the balance of cleaning adjunct materials by weight of composition. In other aspects of the present disclosure, the cleaning compositions also comprise pectin degrading enzymes at a level of about 0.0001% to about 10%, about 0.001% to about 5%, about 0.001% to about 2%, about 0.005% to about 0.5% pectin degrading enzyme by weight of the composition.

In some other embodiments, any suitable xyloglucanase finds used in the cleaning compositions of the present disclosure. Suitable xyloglucanases include, but are not limited to those of plant, fungal, or bacterial origin. Chemically or genetically modified mutants are included in some embodiments. As used herein, "xyloglucanase(s)" encompass the family of enzymes described by Vincken and Voragen at Wageningen University [Vincken et al (1994) *Plant Physiol.,* 104, 99-107] and are able to degrade xyloglucans as described in Hayashi et al (1989) *Plant. Physiol. Plant Mol. Biol.,* 40, 139-168. Vincken et al demonstrated the removal of xyloglucan coating from cellulose of the isolated apple cell wall by a xyloglucanase purified from *Trichoderma viride* (endo-IV-glucanase). This enzyme enhances the enzymatic degradation of cell wall-embedded cellulose and work in synergy with pectic enzymes. Rapidase LIQ+ from Gist-Brocades contains a xyloglucanase activity.

In some embodiments of the present disclosure, the disclosed cleaning compositions further comprise xyloglucanases at a level from about 0.00001% to about 10% of additional xyloglucanase by weight of the composition and the balance of cleaning adjunct materials by weight of composition. In other aspects of the present disclosure, the cleaning compositions also comprise xyloglucanases at a level of about 0.0001% to about 10%, about 0.001% to about 5%, about 0.001% to about 2%, about 0.005% to about 0.5% xyloglucanase by weight of the composition. In certain other embodiments, xyloglucanases for specific applications are alkaline xyloglucanases, i.e., enzymes having an enzymatic activity of at least 10%, preferably at lest 25%, more preferably at least 40% of their maximum activity at a pH ranging from 7 to 12. In certain other embodiments, the xyloglucanases are enzymes having their maximum activity at a pH of from about 7.0 to about 12.

In some further embodiments, any suitable cellulase finds used in the cleaning compositions of the present disclosure. Suitable cellulases include, but are not limited to those of bacterial or fungal origin. Chemically or genetically modified mutants are included in some embodiments. Suitable cellulases include, but are not limited to *Humicola insolens* cellulases (See, e.g., U.S. Pat. No. 4,435,307). Especially suitable cellulases are the cellulases having color care benefits (See, e.g., EP 0 495 257). Commercially available cellulases that find use in the present disclosure include, but are not limited to ENDOLASE®, CELLUCLEAN®, CELLUZYME®, CAREZYME® (Novozymes A/S, Denmark). Additional commercially available cellulases include PURADEX® (Genencor, A Danisco Division, Palo Alto, Calif.) and KAC-500 (B)™ (Kao Corporation). In some embodiments, cellulases are incorporated as portions or fragments of mature wild-type or variant cellulases, wherein a portion of the N-terminus is deleted (See, e.g., U.S. Pat. No. 5,874,276). In some embodiments, the cleaning compositions of the present disclosure further comprise cellulases at a level from about 0.00001% to about 10% of additional cellulase by weight of the composition and the balance of cleaning adjunct materials by weight of composition. In other aspects of the present disclosure, the cleaning compositions also comprise cellulases at a level of about 0.0001% to about 10%, about 0.001% to about 5%, about 0.001% to about 2%, about 0.005% to about 0.5% cellulase by weight of the composition.

In still further embodiments, any lipase suitable for use in detergent compositions also finds use in the present disclosure. Suitable lipases include, but are not limited to those of bacterial or fungal origin. Chemically or genetically modified mutants are included in some embodiments. Examples of useful lipases include *Humicola lanuginosa* lipase (See, e.g., EP 258 068, and EP 305 216), *Rhizomucor miehei* lipase (See, e.g., EP 238 023), *Candida* lipase, such as *C. antarctica* lipase (e.g., the *C. antarctica* lipase A or B; see, e.g., EP 214 761), *Pseudomonas* lipases such as *P. alcaligenes* lipase and *P. pseudoalcaligenes* lipase (See, e.g., EP 218 272), *P. cepacia* lipase (See, e.g., EP 331 376), *P. stutzeri* lipase (See, e.g., GB 1,372,034), *P. fluorescens* lipase, *Bacillus* lipase (e.g., *B. subtilis* lipase [Dartois et al., (1993) *Biochem. Biophys. Acta* 1131:253-260]; *B. stearothermophilus* lipase [See, e.g., JP 64/744992]; and *B. pumilus* lipase [See, e.g., WO 91/16422]). Furthermore, a number of cloned lipases find use in some embodiments of the present disclosure, including but not limited to *Penicillium camembertii* lipase (See, Yamaguchi et al., [1991] *Gene* 103:61-67), *Geotricum candidum* lipase (See, Schimada et al., [1989] *J. Biochem.* 106:383-388), and various *Rhizopus* lipases such as *R. delemar* lipase (See, Hass et al., [1991] *Gene* 109:117-113), *R. niveus* lipase (Kugimiya et al., [1992] *Biosci. Biotech. Biochem.* 56:716-719), and *R. oryzae* lipase. Other types of lipolytic enzymes such as cutinases also find use in some embodiments of the present disclosure, including but not limited to the cutinase derived from *Pseudomonas mendocina* (See, WO 88/09367), and the cutinase derived from *Fusarium solani* pisi (See, WO 90/09446). Additional suitable lipases include commercially available lipases such as M1 LIPASE™, LUMA FAST™, and LIPOMAX™ (Genencor, A Danisco Division, Palo Alto, Calif.); LIPEX®, LIPOCLEAN®, LIPOLASE® and LIPOLASE® ULTRA (Novozymes A/S, Denmark); and LIPASE P™ "Amano" (Amano Pharmaceutical Co. Ltd., Japan).

In some embodiments, the disclosed cleaning compositions further comprise lipases at a level from about 0.00001% to about 10% of additional lipase by weight of the composition and the balance of cleaning adjunct materials by weight of composition. In other aspects of the present disclosure, the cleaning compositions also comprise lipases at a level of about 0.0001% to about 10%, about 0.001% to about 5%, about 0.001% to about 2%, about 0.005% to about 0.5% lipase by weight of the composition.

In some embodiments, peroxidases are used in combination with hydrogen peroxide or a source thereof (e.g., a percarbonate, perborate or persulfate) in the compositions of the present disclosure. In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See, e.g., WO 94/12621 and WO 95/01426). Suitable peroxidases/oxidases include, but are not limited to those of plant, bacterial or fungal origin. Chemically or genetically modified mutants are included in some embodiments. In some embodiments, the cleaning compositions of the present disclosure further comprise peroxidase and/or oxidase enzymes at a level from about 0.00001% to about 10% of additional peroxidase and/or oxidase by weight of the composition and the balance of cleaning adjunct materials by weight of composition. In other aspects of the present disclosure, the cleaning compositions also comprise peroxidase and/or oxidase enzymes at a level of about 0.0001% to about 10%, about 0.001% to about 5%, about 0.001% to about 2%, about 0.005% to about 0.5% peroxidase and/or oxidase enzymes by weight of the composition.

In some embodiments, additional enzymes find use, including but not limited to perhydrolases (See, e.g., WO 05/056782). In addition, in some particularly preferred embodiments, mixtures of the above mentioned enzymes are encompassed herein, in particular one or more additional protease, amylase, lipase, mannanase, and/or at least one cellulase. Indeed, it is contemplated that various mixtures of these enzymes will find use in the present disclosure. It is also contemplated that the varying levels of the Bag Man1 polypeptide(s) and one or more additional enzymes may both independently range to about 10%, the balance of the cleaning composition being cleaning adjunct materials. The specific selection of cleaning adjunct materials are readily made by considering the surface, item, or fabric to be cleaned, and the desired form of the composition for the cleaning conditions during use (e.g., through the wash detergent use).

Examples of suitable cleaning adjunct materials include, but are not limited to, surfactants, builders, bleaches, bleach activators, bleach catalysts, other enzymes, enzyme stabilizing systems, chelants, optical brighteners, soil release polymers, dye transfer agents, dye transfer inhibiting agents, catalytic materials, hydrogen peroxide, sources of hydrogen peroxide, preformed peracids, polymeric dispersing agents, clay soil removal agents, structure elasticizing agents, dispersants, suds suppressors, dyes, perfumes, colorants, filler salts, hydrotropes, photoactivators, fluorescers, fabric conditioners, fabric softeners, carriers, hydrotropes, processing aids, solvents, pigments, hydrolyzable surfactants, preservatives, anti-oxidants, anti-shrinkage agents, anti-wrinkle agents, germicides, fungicides, color speckles, silvercare, anti-tarnish and/or anti-corrosion agents, alkalinity sources, solubilizing agents, carriers, processing aids, pigments, and pH control agents (See, e.g., U.S. Pat. Nos. 6,610,642; 6,605,458; 5,705,464; 5,710,115; 5,698,504; 5,695,679; 5,686,014; and 5,646,101; all of which are incorporated herein by reference). Embodiments of specific cleaning composition materials are exemplified in detail below. In embodiments in which the cleaning adjunct materials are not compatible with the disclosed Bag Man1 polypeptides in the cleaning compositions, then suitable methods of keeping the cleaning adjunct materials and the endo-β-mannanase(s) separated (i.e., not in contact with each other) until combination of the two components is appropriate are used. Such separation methods include any suitable method known in the art (e.g., gelcaps, encapsulation, tablets, physical separation, etc.).

In some preferred embodiments, an effective amount of one or more Bag Man1 polypeptide(s) provided herein are included in compositions useful for cleaning a variety of surfaces in need of stain removal. Such cleaning compositions include cleaning compositions for such applications as cleaning hard surfaces, fabrics, and dishes. Indeed, in some embodiments, the present disclosure provides fabric cleaning compositions, while in other embodiments, the present disclosure provides non-fabric cleaning compositions. Notably, the present disclosure also provides cleaning compositions suitable for personal care, including oral care (including dentrifices, toothpastes, mouthwashes, etc., as well as denture cleaning compositions), skin, and hair cleaning compositions. Additionally, in still other embodiments, the present disclosure provides fabric softening compositions. It is intended that the present disclosure encompass detergent compositions in any form (i.e., liquid, granular, bar, semisolid, gels, emulsions, tablets, capsules, etc.).

By way of example, several cleaning compositions wherein the disclosed Bag Man1 polypeptides find use are described in greater detail below. In some embodiments in which the disclosed cleaning compositions are formulated as compositions suitable for use in laundry machine washing method(s), the compositions of the present disclosure preferably contain at least one surfactant and at least one builder compound, as well as one or more cleaning adjunct materials preferably selected from organic polymeric compounds, bleaching agents, additional enzymes, suds suppressors, dispersants, lime-soap dispersants, soil suspension and anti-redeposition agents and corrosion inhibitors. In some embodiments, laundry compositions also contain softening agents (i.e., as additional cleaning adjunct materials). The compositions of the present disclosure also find use detergent additive products in solid or liquid form. Such additive products are intended to supplement and/or boost the performance of conventional detergent compositions and can be added at any stage of the cleaning process. In some embodiments, the density of the laundry detergent compositions herein ranges from about 400 to about 1200 g/liter, while in other embodiments, it ranges from about 500 to about 950 g/liter of composition measured at 20° C.

In embodiments formulated as compositions for use in manual dishwashing methods, the compositions of the disclosure preferably contain at least one surfactant and preferably at least one additional cleaning adjunct material selected from organic polymeric compounds, suds enhancing agents, group II metal ions, solvents, hydrotropes, and additional enzymes.

In some embodiments, various cleaning compositions such as those provided in U.S. Pat. No. 6,605,458 find use with the Bag Man1 polypeptides of the present disclosure. Thus, in some embodiments, the compositions comprising at least one Bag Man1 polypeptide of the present disclosure is a compact granular fabric cleaning composition, while in other embodiments, the composition is a granular fabric cleaning composition useful in the laundering of colored fabrics, in further embodiments, the composition is a granular fabric cleaning composition which provides softening through the wash capacity, in additional embodiments, the composition is a heavy duty liquid fabric cleaning composition. In some embodiments, the compositions comprising at least one Bag Man1 polypeptide of the present disclosure are fabric cleaning compositions such as those described in U.S. Pat. Nos. 6,610,642 and 6,376,450. In addition, the Bag Man1 polypeptides of the present disclosure find use in granular laundry detergent compositions of particular utility under European or Japanese washing conditions (See, e.g., U.S. Pat. No. 6,610,642).

In some alternative embodiments, the present disclosure provides hard surface cleaning compositions comprising at least one Bag Man1 polypeptide provided herein. Thus, in some embodiments, the compositions comprising at least one Bag Man1 polypeptide of the present disclosure is a hard surface cleaning composition such as those described in U.S. Pat. Nos. 6,610,642; 6,376,450; and 6,376,450.

In yet further embodiments, the present disclosure provides dishwashing compositions comprising at least one Bag Man1 polypeptide provided herein. Thus, in some embodiments, the compositions comprising at least one Bag Man1 polypeptide of the present disclosure is a hard surface cleaning composition such as those in U.S. Pat. Nos. 6,610,642 and 6,376,450. In some still further embodiments, the present disclosure provides dishwashing compositions comprising at least one Bag Man1 polypeptide provided herein. In some further embodiments, the compositions comprising at least one Bag Man1 polypeptide of the present disclosure comprise oral care compositions such as those in U.S. Pat. Nos. 6,376,450 and 6,605,458. The formulations and descriptions of the compounds and cleaning adjunct materials contained in the aforementioned U.S. Pat. Nos. 6,376,450; 6,605,458; and 6,610,642 find use with the Bag Man1 polypeptides provided herein.

In still further embodiments, the compositions comprising at least one Bag Man1 polypeptide of the present disclosure comprise fabric softening compositions such as those in GB-A1400898, GB-A1514 276, EP 0 011 340, EP 0 026 528, EP 0 242 919, EP 0 299 575, EP 0 313 146, and U.S. Pat. No. 5,019,292. The formulations and descriptions of the compounds and softening agents contained in the aforementioned GB-A1 400898, GB-A1 514 276, EP 0 011 340, EP 0 026 528, EP 0 242 919, EP 0 299 575, EP 0 313 146, and U.S. Pat. No. 5,019,292 find use with the Bag Man1 polypeptides provided herein The cleaning compositions of the present disclosure are formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; and 5,486,303; all of which are incorporated herein by reference. When a low pH cleaning composition is desired, the pH of such composition is adjusted via the addition of a material such as monoethanolamine or an acidic material such as HCl.

While not essential for the purposes of the present disclosure, the non-limiting list of adjuncts illustrated hereinafter are suitable for use in the instant cleaning compositions. In some embodiments, these adjuncts are incorporated for example, to assist or enhance cleaning performance, for treatment of the substrate to be cleaned, or to modify the aesthetics of the cleaning composition as is the case with perfumes, colorants, dyes or the like. It is understood that such adjuncts are in addition to the Bag Man1 polypeptides of the present disclosure. The precise nature of these additional components, and levels of incorporation thereof, will depend on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282; 6,306,812; and 6,326,348 are incorporated by reference. The aforementioned adjunct ingredients may constitute the balance of the cleaning compositions of the present disclosure.

In some embodiments, the cleaning compositions according to the present disclosure comprise at least one surfactant and/or a surfactant system wherein the surfactant is selected from nonionic surfactants, anionic surfactants, cationic surfactants, ampholytic surfactants, zwitterionic surfactants, semi-polar nonionic surfactants, and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed by such compositions' acidic contents. In some embodiments, the surfactant is present at a level of from about 0.1% to about 60%, while in alternative embodiments the level is from about 1% to about 50%, while in still further embodiments the level is from about 5% to about 40%, by weight of the cleaning composition.

In some embodiments, the cleaning compositions of the present disclosure contain at least one chelating agent. Suitable chelating agents may include, but are not limited to copper, iron, and/or manganese chelating agents, and mixtures thereof. In embodiments in which at least one chelating agent is used, the cleaning compositions of the present disclosure comprise from about 0.1% to about 15% or even from about 3.0% to about 10% chelating agent by weight of the subject cleaning composition.

In some still further embodiments, the cleaning compositions provided herein contain at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

As indicated herein, in some embodiments, anti-redeposition agents find use in some embodiments of the present disclosure. In some preferred embodiments, non-ionic surfactants find use. For example, in automatic dishwashing embodiments, non-ionic surfactants find use for surface modification purposes, in particular for sheeting, to avoid filming and spotting and to improve shine. These non-ionic surfactants also find use in preventing the re-deposition of soils. In some preferred embodiments, the anti-redeposition agent is a non-ionic surfactant as known in the art (See, e.g., EP 2 100 949).

In some embodiments, the cleaning compositions of the present disclosure include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, and polyvinylimidazoles, or mixtures thereof. In embodiments in which at least one dye transfer inhibiting agent is used, the cleaning compositions of the present disclosure comprise from about 0.0001% to about 10%, from about 0.01% to about 5%, or even from about 0.1% to about 3% by weight of the cleaning composition.

In some embodiments, silicates are included within the compositions of the present disclosure. In some such embodiments, sodium silicates (e.g., sodium disilicate, sodium metasilicate, and crystalline phyllosilicates) find use. In some embodiments, silicates are present at a level of from about 1% to about 20%. In some preferred embodiments, silicates are present at a level of from about 5% to about 15% by weight of the composition.

In some still additional embodiments, the cleaning compositions of the present disclosure also contain dispersants. Suitable water-soluble organic materials include, but are not limited to the homo- or co-polymeric acids or their salts, in which the polycarboxylic acid comprises at least two carboxyl radicals separated from each other by not more than two carbon atoms.

In some further embodiments, the enzymes used in the cleaning compositions are stabilized by any suitable technique. In some embodiments, the enzymes employed herein are stabilized by the presence of water-soluble sources of calcium and/or magnesium ions in the finished compositions that provide such ions to the enzymes. In some embodiments, the enzyme stabilizers include oligosaccharides, polysaccharides, and inorganic divalent metal salts, including alkaline earth metals, such as calcium salts. It is contemplated that various techniques for enzyme stabilization will find use in the present disclosure. For example, in some embodiments, the enzymes employed herein are stabilized by the presence of water-soluble sources of zinc (II), calcium (II), and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV). Chlorides and sulfates also find use in some embodiments of the present disclosure. Examples of suitable oligosaccharides and polysaccharides (e.g., dextrins) are known in the art (See, e.g., WO 07/145,964). In some embodiments, reversible protease inhibitors also find use, such as boron-containing compounds (e.g., borate, 4-formyl phenyl boronic acid) and/or a tripeptide aldehyde find use to further improve stability, as desired.

In some embodiments, bleaches, bleach activators, and/or bleach catalysts are present in the compositions of the present disclosure. In some embodiments, the cleaning compositions of the present disclosure comprise inorganic and/or organic bleaching compound(s). Inorganic bleaches may include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Any suitable salt known in the art finds use in the present disclosure (See, e.g., EP 2 100 949).

In some embodiments, bleach activators are used in the compositions of the present disclosure. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxycarboxylic acids having preferably from about 1 to about 10 carbon atoms, in particular from about 2 to about 4 carbon atoms, and/or optionally substituted perbenzoic acid. Additional bleach activators are known in the art and find use in the present disclosure (See, e.g., EP 2 100 949).

In addition, in some embodiments and as further described herein, the cleaning compositions of the present disclosure further comprise at least one bleach catalyst. In some embodiments, the manganese triazacyclononane and related complexes find use, as well as cobalt, copper, manganese, and iron complexes. Additional bleach catalysts find use in the present disclosure (See, e.g., U.S. Pat. No. 4,246,612; U.S. Pat. No. 5,227,084; U.S. Pat. No. 4,810,410; WO 99/06521; and EP 2 100 949).

In some embodiments, the cleaning compositions of the present disclosure contain one or more catalytic metal complexes. In some embodiments, a metal-containing bleach catalyst finds use. In some preferred embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See, e.g., U.S. Pat. No. 4,430,243). In some embodiments, the cleaning compositions of the present disclosure are catalyzed by means of a manganese compound. Such compounds and levels of use are well known in the art (See, e.g., U.S. Pat. No. 5,576,282). In additional embodiments, cobalt bleach catalysts find use in the cleaning compositions of the present disclosure. Various cobalt bleach catalysts are known in the art (See, e.g., U.S. Pat. Nos. 5,597,936 and 5,595,967) and are readily prepared by known procedures.

In some additional embodiments, the cleaning compositions of the present disclosure include a transition metal complex of a macropolycyclic rigid ligand (MRL). As a practical matter, and not by way of limitation, in some embodiments, the compositions and cleaning processes provided by the present disclosure are adjusted to provide on the order of at least one part per hundred million of the active MRL species in the aqueous washing medium, and in some preferred embodiments, provide from about 0.005 ppm to about 25 ppm, more preferably from about 0.05 ppm to about 10 ppm, and most preferably from about 0.1 ppm to about 5 ppm, of the MRL in the wash liquor.

In some embodiments, preferred transition-metals in the instant transition-metal bleach catalyst include, but are not limited to manganese, iron, and chromium. Preferred MRLs also include, but are not limited to special ultra-rigid ligands that are cross-bridged (e.g., 5,12-diethyl-1,5,8,12-tetraazabicyclo[6.6.2]hexadecane). Suitable transition metal MRLs are readily prepared by known procedures (See, e.g., WO 2000/32601 and U.S. Pat. No. 6,225,464).

In some embodiments, the cleaning compositions of the present disclosure comprise metal care agents. Metal care agents find use in preventing and/or reducing the tarnishing, corrosion, and/or oxidation of metals, including aluminum, stainless steel, and non-ferrous metals (e.g., silver and copper). Suitable metal care agents include those described in EP 2 100 949, WO 94/26860, and WO 94/26859). In some embodiments, the metal care agent is a zinc salt. In some further embodiments, the cleaning compositions of the present disclosure comprise from about 0.1% to about 5% by weight of one or more metal care agent.

As indicated above, the cleaning compositions of the present disclosure are formulated into any suitable form and prepared by any process chosen by the formulator, non-limiting examples of which are described in U.S. Pat. Nos. 5,879,584; 5,691,297; 5,574,005; 5,569,645; 5,516,448; 5,489,392; and 5,486,303; all of which are incorporated herein by reference. In some embodiments in which a low pH cleaning composition is desired, the pH of such composition is adjusted via the addition of an acidic material such as HCl.

The cleaning compositions disclosed herein of find use in cleaning a situs (e.g., a surface, dishware, or fabric). Typically, at least a portion of the situs is contacted with an embodiment of the present cleaning composition, in neat form or diluted in wash liquor, and then the situs is optionally washed and/or rinsed. For purposes of the present disclosure, "washing" includes but is not limited to, scrubbing and mechanical agitation. In some embodiments, the cleaning compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric mass ratio is typically from about 1:1 to about 30:1.

VI. Bag Man1 Polypeptides as Chemical Reagents

The preference of Bag Man1 for polysaccharide chains containing mannose units, including but not limited to mannans, galactomannans, and glucomannans, makes the present polypeptides particularly useful for performing mannan hydrolysis reactions involving polysaccharide substrates containing 1,4-β-D-mannosidic linkages.

In general terms, a donor molecule is incubated in the presence of an isolated Bag Man1 polypeptide or fragment or variant thereof under conditions suitable for performing a mannan hydrolysis reaction, followed by, optionally, isolating a product from the reaction. Alternatively, in the context of a foodstuff, the product may become a component of the foodstuff without isolation. In certain embodiments, the donor molecule is a polysaccharide chain comprising mannose units, including but not limited to mannans, glucomannans, galactomannans, and galactoglucomannans.

VII. Bag Man1 Polypeptides for Food Processing and Animal Feed

Several anti-nutritional factors can limit the use of specific plant material in the preparation of animal feed and food for humans. For example, plant material containing oligomannans such as mannan, galactomannan, glucomannan and galactoglucomannan can reduce the digestibility and absorption of nutritional compounds such as minerals, vitamins, sugars and fats by the animals. The negative effects are in particular due to the high viscosity of the mannan-containing polymers and to the ability of the mannan-containing polymers to adsorb nutritional compounds. These effects are reduced through the use of mannan-containing polymers degrading enzymes, namely endo-β-mannanase enzymes such as the Bag Man1 polypeptides described herein, which permit a higher proportion of mannan-containing polymers containing cheap plant material to be included in the feed resulting in a reduction of feed costs. Additionally, through the activity of the Bag Man1 polypeptides, mannan-containing polymers are broken down to simpler sugars, which can be more readily assimilated to provide additional energy.

Accordingly, compositions comprising any of the Bag Man1 polypeptides described herein preferably used for processing and/or manufacturing of food or animal feed.

In one aspect of the invention, there is provided a bread improver composition comprising any of the BagMan1 polypeptides of the current invention, optionally with a source of mannan or glucomannan or galactomannan present, and further optionally with other enzymes present.

In general terms animal feed containing plant material is incubated in the presence of an isolated Bag Man1 polypeptide or fragment or variant thereof under conditions suitable for breaking down mannan-containing polymers.

The Bag Man1 polypeptides of the present disclosure are useful as additives to feed for non-human animals. The term non-human animal includes all non-ruminant and ruminant animals. In a particular embodiment, the non-ruminant animal, is selected from the group consisting of, but not limited to, horses and monogastric animals such as, but not limited to, pigs, poultry, swine and fish. In further embodiments, the pig may be, but not limited to, a piglet, a growing pig, and a sow; the poultry may be, but not limited to, a turkey, a duck and a chicken including, but not limited to, a broiler chick, a layer; and fish including but not limited to salmon, trout, tilapia, catfish and carps; and crustaceans including but not limited to shrimps and prawns. such as poultry and swine, In a further embodiment, the non-human animal is a ruminant animal including, but not limited to, cattle, young calves, goats, sheep, giraffes, bison, moose, elk, yaks, water buffalo, deer, camels, alpacas, llamas, antelope, pronghorn, and nilgai. The Bag Man1 polypeptides of the present disclosure are also useful as additives. The Bag Man1 polypeptides of the present disclosure are also useful for human food. In some embodiments, the Bag Man1 polypeptides are used to pretreat the feed instead of as a feed additive. In some preferred embodiment, the Bag Man1 polypeptides are added to or used to pretreat feed for weanling pigs, nursery pigs, piglets, fattening pigs, growing pigs, finishing pigs, laying hens, broiler chicks, turkeys. In some embodiment, the Bag Man1 polypeptides are added to or used to pretreat feed from plant material such as palm kernel, coconut, konjac, locust bean gum, gum guar, soy beans, barley, oats, flax, wheat, corn, linseed, citrus pulp, cottonseed, groundnut, rapeseed, sunflower, peas, and lupines.

Since the Bag Man1 polypeptides of the present disclosure are thermostable enzymes, they find used in processes of producing pelleted feed in which heat is applied to the feed mixture before the pelleting step, as it is the case in most commercial pellet mills. The Bag Man1 polypeptides are added to the other feed ingredients in advance of the pelleting step or after the pelleting step to the already formed feed pellets.

In compositions containing any of the disclosed Bag Man1 polypeptides intended for food processing or as a feed supplement, the compositions optionally contain other substituents such as coloring agents, aroma compounds, stabilizers, vitamins, minerals, other feed or food enhancing enzymes and the like. This applies in particular to the so-called pre-mixes. Food additives according to this present invention may be combined with other food components to produce processed food products. The resulting, combined food additive is mixed in an appropriate amount with other food components such as cereal or plant proteins to form a processed food product.

Accordingly, the present invention relates to an animal feed composition and/or animal feed additive composition and/or pet food comprising the Bag Man1 polypeptides.

The present invention further relates to a method for preparing such animal feed composition and/or animal feed additive composition and/or pet food comprising mixing the Bag Man1 polypeptides with one or more animal feed ingredients and/or animal feed additive ingredients and/or pet food ingredients.

Furthermore, the present invention relates to the use of the Bag Man1 polypeptides in the preparation of an animal feed composition and/or animal feed additive composition and/or pet food.

In the present context, it is intended that the term pet food is understood to mean a food for a household animal such as, but not limited to dogs, cats, gerbils, hamsters, chinchillas, fancy rats, guinea pigs; avian pets, such as canaries, parakeets, and parrots; reptile pets, such as turtles, lizards and snakes; and aquatic pets, such as tropical fish and frogs.

The terms animal feed composition, feedstuff and fodder are used interchangeably and may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins.

VIIIa. Bag Man1 Polypeptides for Fermented Beverages, Such as Beer

The terms animal feed composition, feedstuff and fodder are used interchangeably and may comprise one or more feed materials selected from the group comprising a) cereals, such as small grains (e.g., wheat, barley, rye, oats and combinations thereof) and/or large grains such as maize or sorghum; b) by products from cereals, such as corn gluten meal, Distillers Dried Grain Solubles (DDGS) (particularly corn based Distillers Dried Grain Solubles (cDDGS), wheat bran, wheat middlings, wheat shorts, rice bran, rice hulls, oat hulls, palm kernel, and citrus pulp; c) protein obtained from sources such as soya, sunflower, peanut, lupin, peas, fava beans, cotton, canola, fish meal, dried plasma protein, meat and bone meal, potato protein, whey, copra, sesame; d) oils and fats obtained from vegetable and animal sources; e) minerals and vitamins In aspects of the invention the food composition or additive may be liquid or solid In an aspect of the invention the food composition is a beverage, including, but not limited to, a fermented beverage such as beer and wine, comprising any of the Bag Man1 polypeptides of the invention.

In the context of the present invention, the term "fermented beverage" is meant to comprise any beverage produced by a method comprising a fermentation process, such as a microbial fermentation, such as a bacterial and/or yeast fermentation.

In an aspect of the invention the fermented beverage is beer. The term "beer" is meant to comprise any fermented wort produced by fermentation/brewing of a starch-containing plant material. Often, beer is produced from malt or adjunct, or any combination of malt and adjunct as the starch-containing plant material. As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, potato, tapioca, cassava and syrups, such as corn syrup, sugar cane syrup, inverted sugar syrup, barley and/or wheat syrups, and the like may be used as a source of starch As used herein, the term "mash" refers to an aqueous slurry of any starch and/or sugar containing plant material such as grist, e.g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

In another aspect the invention relates to a method of preparing a fermented beverage such as beer comprising mixing any of the Bag Man1 polypeptides of the invention with malt or adjunct.

Examples of beers comprise: full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavoured malt beverages, e.g. citrus flavoured, such as lemon-, orange-, lime-, or berry-flavoured malt beverages, liquor flavoured malt beverages, e.g., vodka-, rum-, or tequila-flavoured malt liquor, or coffee flavoured malt beverages, such as caffeine-flavoured malt liquor, and the like.

One aspect of the invention relates to the use of any of the Bag Man1 polypeptides according to the invention in the production of a fermented beverage, such as a beer.

Another aspect concerns a method of providing a fermented beverage comprising the step of contacting a mash and/or a wort with any of the Bag Man1 polypeptides of the current invention.

A further aspect relates to a method of providing a fermented beverage comprising the steps of: (a) preparing a mash, (b) filtering the mash to obtain a wort, and (c) fermenting the wort to obtain a fermented beverage, such as a beer, wherein any of the Bag Man1 polypeptides is added to: (i) the mash of step (a) and/or (ii) the wort of step (b) and/or (iii) the wort of step (c).

According to yet another aspect, a fermented beverage, such as a beer, is produced or provided by a method comprising the step(s) of (1) contacting a mash and/or a wort with any of the Bag Man1 polypeptides of the current invention; and/or (2) (a) preparing a mash, (b) filtering the mash to obtain a wort, and (c) fermenting the wort to obtain a fermented beverage, such as a beer, wherein any of the Bag Man1 polypeptides is added to: (i) the mash of step (a) and/or (ii) the wort of step (b) and/or (iii) the wort of step (c).

Particular embodiments pertains to any of the above use, method or fermented beverage, wherein said fermented beverage is a beer, such as full malted beer, beer brewed under the "Reinheitsgebot", ale, IPA, lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavoured malt beverages, e.g., citrus flavoured, such as lemon-, orange-, lime-, or berry-flavoured malt beverages, liquor flavoured malt beverages, e.g., vodka-, rum-, or tequila-flavoured malt liquor, or coffee flavoured malt beverages, such as caffeine-flavoured malt liquor, and the like.

VIIIb. Bag Man1 Polypeptides for Treating Coffee Extracts

The Bag Man1 polypeptides described herein may also be used for hydrolyzing galactomannans present in liquid coffee extracts. In certain preferred embodiments, the Bag Man1 polypeptides are used to inhibit gel formation during freeze drying of liquid coffee extracts. The decreased viscosity of the extract reduces the energy consumption during drying. In certain other preferred embodiments, the Bag Man1 polypeptides are applied in an immobilized form in order to reduce enzyme consumption and avoid contamination of the coffee extract This use is further disclosed in EP 676 145.

In general terms the coffee extract is incubated in the presence of an isolated Bag Man1 polypeptide or fragment or variant thereof under conditions suitable for hydrolyzing galactomannans present in liquid coffee extract.

VIIIc BagMan1 Polypeptides for Use in Bakery Food Products

In another aspect the invention relates to a method of preparing baked products comprising addition of any of the BigMan1 polypeptides of the invention to dough, followed by baking the dough. Examples of baked products are well known to those skilled in the art and include breads, rolls, puff pastries, sweet fermented doughs, buns, cakes, crackers, cookies, biscuits, waffles, wafers, tortillas, breakfast cereals, extruded products, and the like.

Any of the BigMan1 polypeptides of the invention may be added to dough as part of a bread improver composition. Bread improvers are compositions containing a variety of ingredients, which improve dough properties and the quality of bakery products, e.g. bread and cakes. Bread improvers are often added in industrial bakery processes because of their beneficial effects e.g. the dough stability and the bread texture and volume. Bread improvers usually contain fats and oils as well as additives like emulsifiers, enzymes, antioxidants, oxidants, stabilizers and reducing agents. In addition to any of the BigMan1 polypeptides of the present invention, other enzymes which may also be present in the bread improver or which may be otherwise used in conjunction with any of the BigMan1 polypeptides of the present invention include amylases, hemicellulases, amylolytic complexes, lipases, proteases, xylanases, pectinases, pullulanases, non starch polysaccharide degrading enzymes and redox enzymes like glucose oxidase, lipoxygenase or ascorbic acid oxidase.

In a preferred bakery aspect of the current invention, any of the BigMan1 polypeptides of the invention may be added to dough as part of a bread improver composition which also comprises a glucomannan and/or galactomannan source such as konjac gum, guar gum, locust bean gum (*Ceratonia siliqua*), copra meal, ivory nut mannan (*Phyteleohas macrocarpa*), seaweed mannan extract, coconut meal, and the cell wall of brewers yeast (may be dried, or used in the form of brewers yeast extract). Other acceptable mannan derivatives for use in the current invention include unbranched β-1,4-linked mannan homopolymer and manno-oligosaccharides (mannobiose, mannotriose, mannotetraose and mannopentoase). The combination of any of the BigMan1 polypeptides of the invention with a glucomannan and/or galactomannan and/or galatoglucomannan further improves the dough tolerance, dough flexibility and dough stickiness, improves the bread crumb structure and retards staling of the bread, and the mannanase hydrolysates act as soluble prebiotics by promoting the growth of lactic acid bacteria commonly associated with good health when found at favourable population densities in the colon.

A further aspect of the invention relates to the use of any of the BigMan1 polypeptides of the invention in dough to improve dough tolerance, flexibility and stickiness. Preferably the dough to which any of the BigMan1 polypeptides of the invention may be added is not a pure white flour dough, but comprises bran or oat, rice, millet, maize, or legume flour in addition to or instead of pure wheat flour.

A yet further aspect of the invention relates to the use of any of the BigMan1 polypeptides of the invention in dough to improve the crumb structure and retard staling in the final baked product, such as bread.

VIIIc BagMan1 Polypeptides for Use in Dairy Food Products

In one aspect of the current invention, any of the BigMan1 polypeptides of the invention may be added to milk or any other dairy product to which has also been added a glucomannan and/or galactomannan. Typical glucomannan and/or galactomannan sources are listed above in the bakery aspects, and include guar or konjac gum. The combination of any of the BigMan1 polypeptides of the invention with a glucomannan and/or galactomannan releases mannanase hydrolysates (mannooligosaccharides) which act as soluble prebiotics by promoting the selective growth and proliferation of probiotic bacteria (especially Bifidobacteria and *Lactobacillus* lactic acid bacteria) commonly associated with good health when found at favourable population densities in the large intestine or colon.

In another aspect the invention relates to a method of preparing milk or dairy products comprising addition of any of the BigMan1 polypeptides of the invention and addition of any glucomannan or galactomannan or galactoglucomannan.

In another aspect of the invention any of the BigMan1 polypeptides of the invention are used in combination with any glucomannan or galactomannan prior to or following addition to a dairy based foodstuff to produce a dairy based foodstuff comprising prebiotic mannan hydrolysates. In a further aspect of the invention the thus produced mannooligosacharide-containing dairy product is capable of increasing the population of beneficial human intestinal microflora, and in a yet further aspect of the current invention the dairy based foodstuff may comprise any of the BigMan1 polypeptides of the current invention together with any source of glucomannan and/or galactomannan and/or galactoglucomannan, and a dose sufficient for inoculation of at least one strain of bacteria (such as Bifidobacteria or *Lactobacillus*) known to be of benefit in the human large intestine. Preferably said dairy-based foodstuff is a yoghurt or milk drink.

IX. Bag Man1 Polypeptides for Paper Pulp Bleaching

The Bag Man1 polypeptides described herein find further use in the enzyme aided bleaching of paper pulps such as chemical pulps, semi-chemical pulps, kraft pulps, mechanical pulps or pulps prepared by the sulfite method. In general terms, paper pulps are incubated with an isolated Bag Man1 polypeptide or fragment or variant thereof under conditions suitable for bleaching the paper pulp.

In some embodiments, the pulps are chlorine free pulps bleached with oxygen, ozone, peroxide or peroxyacids. In some embodiments, the Bag Man1 polypeptides are used in enzyme aided bleaching of pulps produced by modified or continuous pulping methods that exhibit low lignin contents. In some other embodiments, the Bag Man1 polypeptides are applied alone or preferably in combination with xylanase and/or endoglucanase and/or alpha-galactosidase and/or cellobiohydrolase enzymes.

X. Bag Man1 Polypeptides for Degrading Thickeners

Galactomannans such as guar gum and locust bean gum are widely used as thickening agents e.g., in food and print paste for textile printing such as prints on T-shirts. Thus the Bag Man1 polypeptides described herein also find use in reducing the thickness or viscosity of mannan-containing substrates. In certain embodiments, the Bag Man1 polypeptides described herein are used for reducing the viscosity of residual food in processing equipment and thereby facilitate cleaning after processing. In certain other embodiments, the disclosed Bag Man1 polypeptides are used for reducing viscosity of print paste, thereby facilitating wash out of surplus print paste after textile printings. In general terms, a mannan-containing substrate is incubated with an isolated Bag Man1 polypeptide or fragment or variant thereof under conditions suitable for reducing the viscosity of the mannan-containing substrate.

Other aspects and embodiments of the present compositions and methods will be apparent from the foregoing description and following examples.

EXAMPLES

The following examples are provided to demonstrate and illustrate certain preferred embodiments and aspects of the present disclosure and should not be construed as limiting.

In the experimental disclosure which follows, the following abbreviations apply: M (molar); mM (millimolar); μM (micromolar); nM (nanomolar); mol (moles); mmol (millimoles); μmol (micromoles); nmol (nanomoles); g and gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); MW (molecular weight); sec (seconds); min(s) (minute/minutes); h(s) and hr(s) (hour/hours); ° C. (degrees Centigrade); QS (quantity sufficient); ND (not done); rpm (revolutions per minute); $H_2O$ (water); $dH_2O$ (deionized water); HCl (hydrochloric acid); aa (amino acid); bp (base pair); kb (kilobase pair); kD (kilodaltons); $MgCl_2$ (magnesium chloride); NaCl (sodium chloride); Ca (calcium); Mg (magnesium); HEPES (4-(2-hydroxyethyl)-1-piperazineethanesulfonic acid); CHES (N-cyclohexyl-2-aminoethanesulfonic acid); w/v (weight to volume); v/v (volume to volume); g (gravity); OD (optical density); ppm (parts per million); m- (meta-); o- (ortho-); p- (para-); PAHBAH (p-hydroxybenzoic acid hydrazide); Bag Man1 (*Bacillus agaradhaerens* mannanase1); SRI (stain removal index).

Example 1

Cloning of *Bacillus agaradhaerens* Glycosyl Hydrolase Bag Man1

*Bacillus agaradhaerens* was selected as a potential source for various glycosyl hydrolases and other enzymes, useful for industrial applications. Genomic DNA for sequencing was obtained by first growing a strain of *Bacillus agaradhaerens* on GAM agar plates (Jones et al., IJSEM, 55: 1711-1714, 2005) at 30° C. for 24 h. Cell material was scraped from the plates and used to prepare genomic DNA with the ZF Fungal/Bacterial DNA miniprep kit from Zymo (Cat No. D6005). The genomic DNA was used for sequencing and to amplify the Bag Man1 gene for expression cloning. The entire genome of *Bacillus agaradhaerens* was sequenced using Illumina® sequencing by synthesis (SBS) technology (www.baseclear.com/sequencing/illumina-sequencing). Genome sequencing and assembly of the sequence data was performed by BaseClear (Leiden, The Netherlands). Contigs were annotated by BioXpr (Namur, Belgium). One of genes identified in this way encodes a glycosyl hydrolase that showed homology by BLASTP to mannanases of various other bacteria. The nucleic acid sequence of this gene, Bag Man1, is listed as SEQ ID NO:1. The amino acid sequence of the protein encoded by the Bag Man1 gene is listed as SEQ ID NO:2. At the N-terminus, the protein is predicted to have a signal peptide with a length of 32 amino acids as determined by the Signal P 3.0 program (www.cbs.dtu/services/SignalP) set to SignalP-NN system (Emanuelsson et al., Nature Protocols, 2: 953-971, 2007). The presence of a signal sequence suggests that Bag Man1 is a secreted glycosyl hydrolase.

The nucleotide sequence of the Bag Man1 coding region is set forth as SEQ ID NO:1. The coding region of the predicted signal peptide sequence is italicized. *atggaaaataagaaaaaaagatcatttaagaataaggcattaatggttgttagcattcttatagtaggcattctcttaat tataatgattcgaaatatgacaaactatgaatcagaggtgcgacgatttgaagcaga* agatgctacgttgaatggggtaacagttaaaaattctgaaccaggattttcgggtact ggctacgtaggtgactttgaagatagctctcagagtgtgacgtttcat gtagatgttc-ctgaaacggatttatacacattaactatcggctatggtgcgatttatggaagtgaaaa agtagccaatgtccttgtaaatggcgagaagctgagctcttttacaatgggaagtgg atttggtaaagcctcagcaggcaacatagtacttaactcaggttcgaatactatttca attacacctgattggacacactttgccattgattatattgaagttaaacttacacctgaa cctataaaacataatgtagagaagaagttaatcaatccaaatgcaacggatgaagc caaagttttaatgagttacttggtggataactttggcgaaaaaatcctttctggacaac atgattttccaaatacaaggccagatgatttagagtatatttatgaaattactggaaag tatcctgctattttaggtttagactttattgataatagcccttcaagagttgagtatgcgag cctttgctgatgaaacaccggtagcaatcaactggtggaataaggggaattgt acctttacttggcattggaatgctcctaaagacttattggatgaaccaggaaatgaat ggtggagaggcttttatacagaagcaacaacattcgacgttgaatacgctttaaatc atccagactcggaagactataaactttaatacgtgatattgatgtgatagctgatga acttaagaaattacaaaaagcagatgttcctgtgttatggagaccgcttcatgaagc ggagggtaaatggttttggtggggaaaaagggccctgaaccagctaaggagtt atggctattaatgtatgacagaatgacgaactatcataacttaaataatttaatatggg tatggaactccattgaagaagattggtaccccggagatgagtatgtggatatagtaa gcttcgattcctacccaggtgactataactacagtccaatgagtg gtcagtatgag-gcgttaaaagagttatcaagtaacaaaaaaataattgcaatagcagaaatggtcc aataccagatcctgatttactacaacgttatcatgctcattatagctggtttactacgtg gaatggcgacatattaagggagcaaaatagtgaagagcatctgaagaacgtcta taatcacgattatgtaattaccttagatgaacttccagattttgaaacatataaggaag acgtaccgttagag.

The amino acid sequence of the Bag Man 1 precursor protein is set forth as SEQ ID NO:2. The predicted native signal peptide is shown in italics. *MENKKKRSFKNKALMVVSILIVGILLIIMIRNMTNYESEVRRFEAEDATL*NGV TVKNSEPGFSGTGYVGDFEDSSQSVTFHVDVPETDL YTLTIGYGAIYGSEKVANVLVNGEKLSSFTMGSGFG KASAGNIVLNSGSNTISITPDWTHFAIDYIEVKLTPEPI KHNVEKKLINPNATDEAKVLMSYLVDNFGEKILSGQ HDFPNTRPDDLEYIYEITGKYPAILGLDFIDNSPSRVE YGAFADETPVAINWWNKGGIVTFTWHWNAPKDLLD EPGNEWWRGFYTEATTFDVEYALNHPDSEDYKLLIR DIDVIADELKKLQKADVPVLWRPLHEAEGKWFWW GKKGPEPAKELWLLMYDRMTNYHNLNNLIVVVWN SIEEDWYPGDEYVDIVSFDSYPGDYNYSPMSGQYEA LKELSSNKKIIAIAENGPIPDPDLLQRYHAHYSWFTT WNGDILREQNSEEHLKNVYNHDYVITLDELPDFETY KEDVPLE.

Example 2

Expression of *Bacillus agaradhaerens* Glycosyl Hydrolase (Bag Man1)

The Bag Man1 gene was amplified by PCR from *Bacillus agaradhaerens* genomic DNA using the following primers: Primer1 (BssHII) 5'-TGAGCGCGCA GGCTGCTGGA AAAATGACAA ACTATGAATC AGAGGT-3' (SEQ ID NO:8), and Primer 2 (BamHI) 5'-TGTGGATCCT TACTCTAACG GTACGTCTTC CTTAT-3' (SEQ ID NO:9). The amplified Bag Man1 gene was cloned into expression plasmid p2JM by BssHII/BamHI double digestion and ligation. The *Bacillus subtilis* expression vector p2JM103BBI (Vogtentanz, *Protein Expr Purif*, 55:40-52, 2007) was digested with the restriction enzymes BssHII and BamHI. The DNA fragment devoid of the BCE103-BBI fusion gene sequence was isolated and used as the expression backbone. Ligation of this DNA fragment to the PCR amplified gene encoding the Bag Man1 mature protein resulted in the addition of three codons between the 3' end of the *Bacillus subtilis* AprE pro-peptide and the 5' end of the Bag Man1 gene. The resulting plasmid shown in FIG. 1 was labeled pML353 (aprE-Bag Man1). Following the natural signal peptidase cleavage in the host, the recombinant Bag Man1 protein produced in this manner was predicted to have three additional amino acids (Ala-Gly-Lys) at its amino-terminus.

The sequence of the Bag Man1 gene was confirmed by DNA sequencing (SEQ ID NO: 3). The Bag Man1 protein was produced in *Bacillus subtilis* cells using previously described methods (Vogtentanz, *Protein Expr Purif*, 55:40-52, 2007). The protein was secreted into the extracellular medium and filtered culture medium was used for the cleaning assays.

Bag Man1 was also purified from a concentrated culture supernatant using the following three chromatography columns: a hydrophobic interaction chromatography column [HiPrep Phenyl (high sub) 16/10] equilibrated with 20 mM Tris pH 8.0, 1M $(NH_4)_2SO_4$ buffer from which the protein was eluted using a linear gradient of equilibration/wash buffer to 20 mM Tris pH 8.0, an anion exchange Sepharose column (HiPrep Q FF 16/10) equilibrated with 20 mM Tris, pH 8.0 from which the protein was eluted using a linear gradient of equilibration/wash buffer to 20 mM Tris, pH 8.0 buffer containing 0.5 M NaCl, and a gel filtration HiLoad Superdex 75 pg 26/60 column from which the protein was eluted using 20 mM sodium phosphate, pH 7.0, containing 0.15 M NaCl. The protein purity and relative size was confirmed by SDS-PAGE. Purified protein was used to perform the pH, temperature profile and activity tests. The predicted molecular weight of the 463 residue protein produced from plasmid pML353 was calculated to be ~53 kDa.

The nucleotide sequence of the Bag Man1 gene from plasmid pML353 (aprE signal sequence is in italics) is set forth as SEQ ID NO: 3: *gtgagaagcaaaaaattgtggatcagcttgttgtttgcgttaacgttaatctttacgatggcgttcagcaacatgagcgcgcaggctgctggaaaa* atgacaaactatgaatcagaggtgcgacgatttgaagcagaagatgctacgttgaat ggggtaacagttaaaaattctgaaccaggattttcgggtactggctacgtaggtgac tttgaagatagctctcagagtgtgacgtttcatgtagatgttcctgaaac ggatttata-cacattaactatcggctatggtgcgatttatggaagtgaaaagtagccaatgtcctt gtaaatggcgagaagctgagctcttttacaatgggaagtggatttggtaaagcctc agcaggcaacatagtacttaactcaggttcgaatactatttcaattacacctgattgga cacactttgccattgattatattgaagttaaacttacacctgaacctataaaacataat-gtagagaagaagttaatcaatccaaatgcaacggatgaagccaaagttttaatgag ttacttggtggataactttggcgaaaaaatcctttctggacaacatgattttccaaata caaggccagatgatttagagtatatttatgaaattactggaaagtatcctgctatttta ggtttagactttattgataatagcccttcaagagttgagtatggagcctttgctgatga aacaccggtagcaatcaactggtggaataaaggggggaattgttacctttacttggca
ttggaatgctcctaaagacttattggatgaaccaggaaatgaatggtggagaggctt
ttatacagaagcaacaacattcgacgttgaatacgctttaaatcatccagactcgga
agactataaactttaatacgtgatattgatgtgatagctgatgaacttaagaaattaca
aaaagcagatgttcctgtgttatggagaccgcttcatgaagcggagggtaaatgg
ttttggtgggggaaaaagggccctgaaccagctaaggagttatggctattaatgtat
gacagaatgacgaactatcataacttaaataatttaatatgggtatggaactccattg
aagaagattggtaccccggagatgagtatgtggatatagtaagcttcgattcctacc
caggtgactataactacagtccaatgagtggtcagtatgaggcgttaaaagagttat
caagtaacaaaaaaataattgcaatagcagaaaatggtccaataccagatcctgat
ttactacaacgttatcatgctcattatagctggtttactacgtggaatggcgacatatta
agggagcaaaatagtgaagagcatctgaagaacgtctataatcacgattatgtaat
tacctagatgaacttccagattttgaaacatataaggaagacgtaccgttagag.

The amino acid sequence of the Bag Man1 precursor expressed from plasmid pML353 is set forth as SEQ ID NO:4, with the signal sequence shown in italics and the three residue addition shown in bold: MRSKKLWISLLFAL-TLIFTMAFSNMSAQAAGKMTNYESEVRRFEAEDATL
NGVTVKNSEPGFSGTGYVGDFEDSSQSVTFHVDVPE
TDLYTLTIGYGAIYGSEKVANVLVNGEKLSSFTMGSG
FGKASAGNIVLNSGSNTISITPDWTHFAIDYIEVKLTPE
PIKHNVEKKLINPNATDEAKVLMSYLVDNFGEKILSG
QHDFPNTRPDDLEYIYEITGKYPAILGLDFIDNSPSRV
EYGAFADETPVAINWWNKGGIVTFTWHWNAPKDLL
DEPGNEWWRGFYTEATTFDVEYALNHPDSEDYKLLI
RDIDVIADELKKLQKADVPVLWRPLHEAEGKWFWW
GKKGPEPAKELWLLMYDRMTNYHNLNNLIwVWNSI
EEDWYPGDEYVDIVSFDSYPGDYNYSPMSGQYEAL
KELSSNKKIIAIAENGPIPDPDLLQRYHAHYSWFTTW
NGDILREQNSEEHLKNVYNHDYVITLDELPDFETYK
EDVPLE.

The amino acid sequence of the Bag Man 1 mature protein expressed from pML353 is set forth as SEQ ID NO:5, with the three residue amino-terminal extension based on the predicted cleavage site shown in bold: AGKMTNYESEVRRFE-AEDATLNGVTVKNSEPGFSGTGYVGDFEDSSQSVTF
HVDVPETDLYTLTIGYGAIYGSEKVANVLVNGEKLSS
FTMGSGFGKASAGNIVLNSGSNTISITPDWTHFAIDYI
EVKLTPEPIKHNVEKKLINPNATDEAKVLMSYLVDNF
GEKILSGQHDFPNTRPDDLEYIYEITGKYPAILGLDFI
DNSPSRVEYGAFADETPVAINWWNKGGIVTFTWHW
NAPKDLLDEPGNEWWRGFYTEATTFDVEYALNHPD
SEDYKLLIRDIDVIADELKKLQKADVPVLWRPLHEAE
GKWFWWGKKGPEPAKELWLLMYDRMTNYHNLNN
LIWVWNSIEEDWYPGDEYVDIVSFDSYPGDYNYSPM
SGQYEALKELSSNKKIIAIAENGPIPDPDLLQRYHAH
YSWFTTWNGDILREQNSEEHLKNVYNHDYVITLDEL
PDFETYKEDVPLE.

The amino acid sequence of the Bag Man 1 mature protein, based on the predicted cleavage of the naturally occurring sequence, is set forth as SEQ ID NO:6: MTNYESEVRRFE-AEDATLNGVTVKNSEPGFSGTGYVGDFEDSSQSVTF
HVDVPETDLYTLTIGYGAIYGSEKVANVLVNGEKLSS
FTMGSGFGKASAGNIVLNSGSNTISITPDWTHFAIDYI
EVKLTPEPIKHNVEKKLINPNATDEAKVLMSYLVDNF
GEKILSGQHDFPNTRPDDLEYIYEITGKYPAILGLDFI
DNSPSRVEYGAFADETPVAINWWNKGGIVTFTWHW
NAPKDLLDEPGNEWWRGFYTEATTFDVEYALNHPD
SEDYKLLIRDIDVIADELKKLQKADVPVLWRPLHEAE
GKWFWWGKKGPEPAKELWLLMYDRMTNYHNLNN
LIWVWNSIEEDWYPGDEYVDIVSFDSYPGDYNYSPM
SGQYEALKELSSNKKIIAIAENGPIPDPDLLQRYHAH
YSWFTTWNGDILREQNSEEHLKNVYNHDYVITLDE
LPDFETYKEDVPLE.

The amino acid sequence of the Bag Man 1 mature protein, based on amino-terminal sequencing of the recombinant protein expressed in B subtilis, is set forth as SEQ ID NO:7: NYESEVRRFEAEDATLNGVTVKNSEPGFSGTGYVGD
FEDSSQSVTFHVDVPETDLYTLTIGYGAIYGSEKVAN
VLVNGEKLSSFTMGSGFGKASAGNIVLNSGSNTISIT-
PDWTHFAIDYIEVKLTPEPIKHNVEKKLINPNATDEA
KVLMSYLVDNFGEKILSGQHDFPNTRPDDLEY IYEIT-
GKYPAILGLDFIDNSPSRVEYGAFADETPVAINWWNK
GGIVTFTWHWNAPKDLLDEPGNEWWRGFYTEATTF
DVEYALNHPDSEDYKLLIRDIDVIADELKKLQKADV
PVLWRPLHEAEGKWFWWGKKGPEPAKELWLLMYD
RMTNYHNLNNLIWVWNSIEEDWYPGDEYVDIVSFD
SYPGDYNYSPMSGQYEALKELSSNKKIIAIAENGPIP
DPDLLQRYHAHYSWFTTWNGDILREQNSEEHLKNV
YNHDYVITLDELPDFETYKEDVPLE.

Example 3

Cleaning Performance of Bag Man1

Bag Man1 produced in *B. subtilis* was secreted into the extracellular medium. After filtration, the culture medium containing Bag Man1 was tested in various cleaning assays.
A. Microswatch 96 Well Assay Format.

Cleaning performance of Bag Man1 (SEQ ID NO.7) was tested in a microswatch assay in combination with a protease. Stain removal experiments were carried out using CS-73 Locust bean gum and CS-43 Guar gum pre-stained cotton swatches (Center For Testmaterials (CFT), the Netherlands) in a 96-well plate format (G080F, Kisker GbR, Germany) using a final volume of 250 µl. Five mm pieces of swatches were cut and placed in each well of the plate. The performance of Bag Man1 was tested in the presence of commercially available heat-inactivated detergents TIDE® powder, TIDE® 2× Ultra Liquid and Ariel® Color, Actilift (Procter & Gamble) tested at a final concentration of 0.3 g/l. The cleaning performance of Bag Man1 was measured in the presence of a protease and compared to the cleaning performance of the protease alone. The proteases used was PURAFECT® (Genencor) for powder detergents and PURAFECT®Prime (Genencor) for liquid detergents.

Bag Man1 was used as a sterile filtered ferment and the dosing was based on total protein determined by a Bradford type assay using the Biorad protein assay (500-0006EDU) and corrected for purity determined by SDS-PAGE using a Criterion stain free system from Bio-Rad. Bag Man1 and a commercial mannanase (Mannastar™ from Genencor International) were tested at a concentration of 0.25 ppm and 1 ppm, and protease was added at 0.5 ppm. Water hardness was adjusted to a final concentration of 100 ppm 2:1 Ca:Mg and the solution was buffered with 5 mM (HEPES pH 8.2 for Tide Liquid and Ariel Gel detergents or CAPS pH 10 for Tide Powder detergent). Each plate contained 3-4 replicates and 2-3 plates were run per swatch type giving a total of 6-12 replicate determinations. The plates were sealed and shaken for 30 minutes at 900 rpm at 30° C. in an iEMS shaker (Thermo Scientific). After incubation, the fabrics were rinsed three times with deionized water using a well washer 4MK2 (Thermo) and dried at 50° C. over night. Stain removal was quantified using RGB measurements taken with a scanner (Microtek Scan Maker 900). The images were imported into Photoshop CSII where RGB values were extracted from the swatch containing areas using IPTK5.0 from Reindeer Graphics. Stain removal was quantified using RGB color measurements taken with a scanner (Microtek Scan Maker 900). The images were imported into Photoshop CSII where RGB color values were extracted from the swatch containing areas using IPTK5.0 from Reindeer Graphics. Stain removal was calculated using the RGB color values as the difference of the post- and pre-cleaning RGB color measurements for each swatch.

ΔSRI (change in Soil Removal Index) values of the washed fabric were calculated in relation to the unwashed fabrics using the formula:

% Soil Removal(*RGB*)=(soil removal *dE*(*RGB*)/initial soil *dE*(*RGB*))×100%

Where:

Soil Removal *dE*(*RGB*)=SQRT((*R* after–*R* before)$^2$+(*G* after–*G* before)+(*B* after–*B* before)$^2$)

and

Initial soil *dE*(*RGB*)=SQRT((*R* ref–*R* before)$^2$+(*G* ref–*G* before)$^2$+(*B* ref–*B* before)$^2$)

RGB ref values are the values of the unsoiled cotton (white). Results are shown in Tables 3-1 and 3-2.

TABLE 3-1

Cleaning performance (% SRI ± 95% confidence interval for n = 12) of Bag Man1 in the presence of protease in different detergents on CFT C-S-73 Locust Bean Gum

| Detergent | Enzyme | Bag Man1 | Mannastar |
|---|---|---|---|
| Ariel gel detergent | 0.5 ppm Protease | 25 ± 8 | 22 ± 6 |
| | 0.25 ppm Mannanase + 0.5 ppm Protease | 43 ± 4 | 41 ± 2 |
| | 1 ppm Mannanase + 0.5 ppm Protease | 43 ± 4 | 42 ± 4 |
| Tide powder detergent | 0.5 ppm Protease | 23 ± 5 | 29 ± 3 |
| | 0.25 ppm Mannanase + 0.5 ppm Protease | 35 ± 2 | 31 ± 2 |
| | 1 ppm Mannanase + 0.5 ppm Protease | 40 ± 1 | 35 ± 2 |
| Tide liquid detergent | 0.5 ppm Protease | 25 ± 6 | 19 ± 4 |
| | 0.25 ppm Mannanase + 0.5 ppm Protease | 40 ± 3 | 26 ± 3 |
| | 1 ppm Mannanase + 0.5 ppm Protease | 42 ± 3 | 30 ± 2 |

TABLE 3-2

Cleaning performance (% SRI ± 95% confidence interval for n =12) of Bag Man1 in the presence of protease in different detergents on CFT C-S-43 Guar Gum

| | Ariel gel detergent | | | Tide Powder detergent | | |
|---|---|---|---|---|---|---|
| | 0.5 ppm Protease | 0.25 ppm Mannanase + 0.5 ppm Protease | 1 ppm Mannanase + 0.5 ppm Protease | 0.5 ppm Protease | 0.25 ppm Mannanase + 0.5 ppm Protease | 1 ppm Mannanase + 0.5 ppm Protease |
| Bag Man1 | 15 ± 5 | 25 ± 3 | 25 ± 3 | 14 ± 4 | 20 ± 3 | 19 ± 2 |
| Mannastar | 18 ± 4 | 17 ± 3 | 16 ± 4 | 10 ± 3 | 16 ± 3 | 14 ± 2 |

The cleaning performance of Bag Man1 protein was also tested in combination with a protease (PURAFECT® or PURAFECT® Prime) and an amylase (ACE prime described in WO2010/115021 or POWERASE®) in a microswatch format. The combination of a protease and an amylase is referred to as CWS (Cold Water System). The assay was performed as described above using 0.25 ppm mannanase with 0.5 ppm PURAFECT® Prime and 0.1 ppm ACE prime with liquid detergents, and 0.8 ppm PURAFECT® and 0.2 ppm POWERASE® with powder detergent. Results are shown in Table 3-3.

TABLE 3-3

Cleaning performance (% SRI ± 95% CI for n = 12) of Bag Man1 in the presence of protease + amylase (CWS) in different detergents on CFT C-S-73 Locust Bean Gum

| | Ariel Gel Detergent | | Tide Powder Detergent | | Tide Liquid Detergent | |
|---|---|---|---|---|---|---|
| | CWS | CWS + Mannanase | CWS | CWS + Mannanase | CWS | CWS + Mannanase |
| Bag Man1 | 34 ± 6 | 43 ± 3 | 30 ± 5 | 36 ± 2 | 29 ± 6 | 40 ± 3 |
| Mannastar | 28 ± 6 | 41 ± 2 | 27 ± 4 | 34 ± 1 | 28 ± 5 | 40 ± 2 |

B. Launder-O-Meter Mid-Scale Assay Format

Figure 2A:
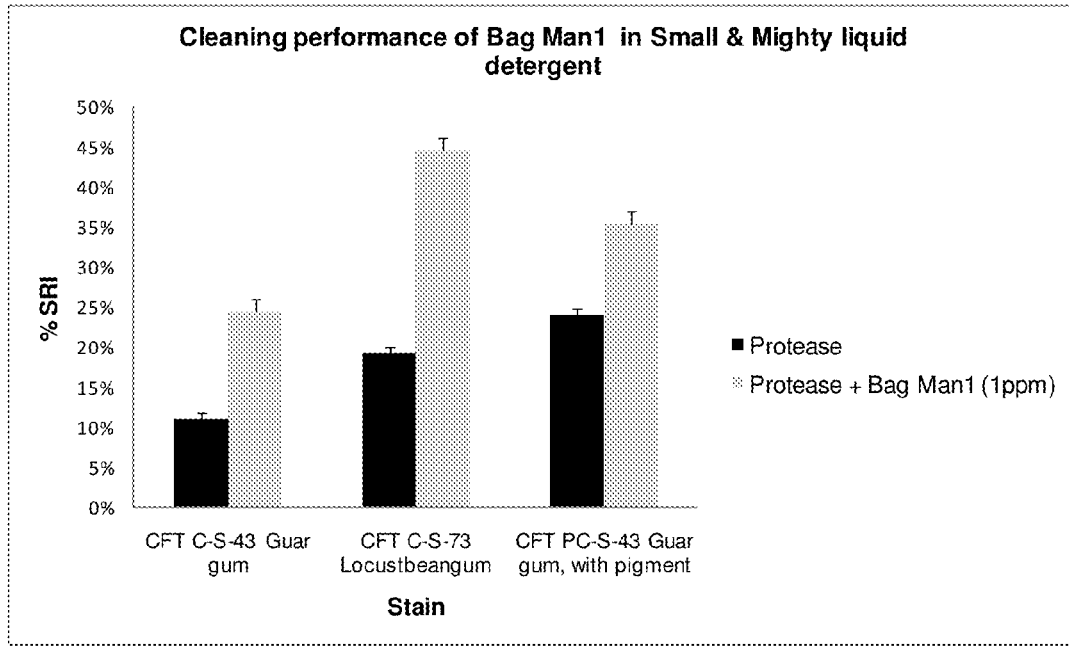
FIG. 2A shows the cleaning performance of Bag Man1 in Small & Mighty liquid detergent.
Figure 2B:
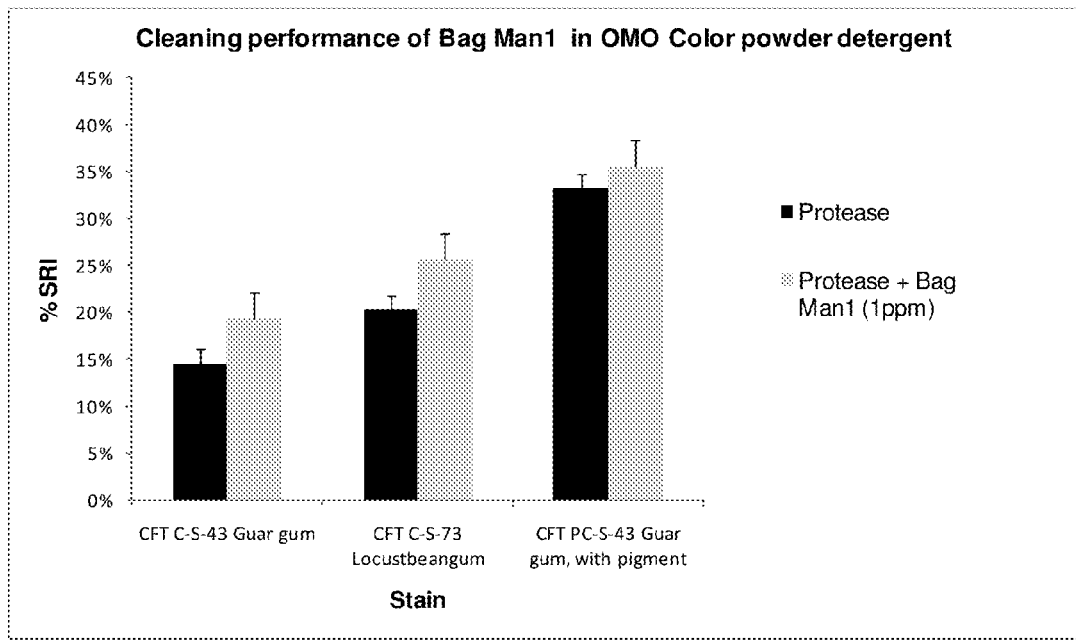
FIG. 2B shows the cleaning performance of Bag Man1 in OMO Color powder detergent.

The cleaning performance of Bag Man1 (SEQ ID NO.7) was tested in a Launder-O-meter LP-2 (Atlas Electric Devices Co., Chicago, Ill.) or equivalent using the CS-43 (Guar Gum), CS-73 (Locust Bean Gum), and PCS-43 (pigment stained Guar Gum) swatches purchased from Center for Testmaterials, Netherlands. The cleaning performance of the protein was tested in combination with a protease (PURAFECT® or PURAFECT® Prime). Swatches were cut to 3 cm×3 cm in size, read on a Konica Minolta CR-400 reflectometer for pre-wash RGB values, and four swatches of each stain type (12 g including ballast soil) were added to each test beaker along with six stainless steel balls. Water hardness was adjusted to a final concentration of 100 ppm and used to dilute the detergents. The commercially available detergent OMO color powder (Unilever) was heat-inactivated and used at a dose of 5.25 g/L. The commercially available Small and Mighty bio liquid detergent (Unilever) contained no enzymes and was used without heat-inactivation at a dose of 2.33 g/L. Varying doses (0.25, 1 and 2.5 ppm) of Bag Man1 along with 0.5 ppm of PURAFECT® Prime for liquid detergent or 0.8 ppm of PURAFECT® for powder detergent were added to each beaker. The washing cycle time was 45 minutes at 40° C. After the wash, the swatches were removed, rinsed for five minutes in cold tap water, spun in a laundry centrifuge and laid flat in a heating cabinet to dry. The dry swatches were covered with dark cloth at room temperature and stain removal was assessed by measuring the RGB values with a Konica Minolta CR-400 reflectometer. The % SRI readings for 1 ppm Bag Man1 dose are shown in FIGS. 2A and 2B.

Figure 3:
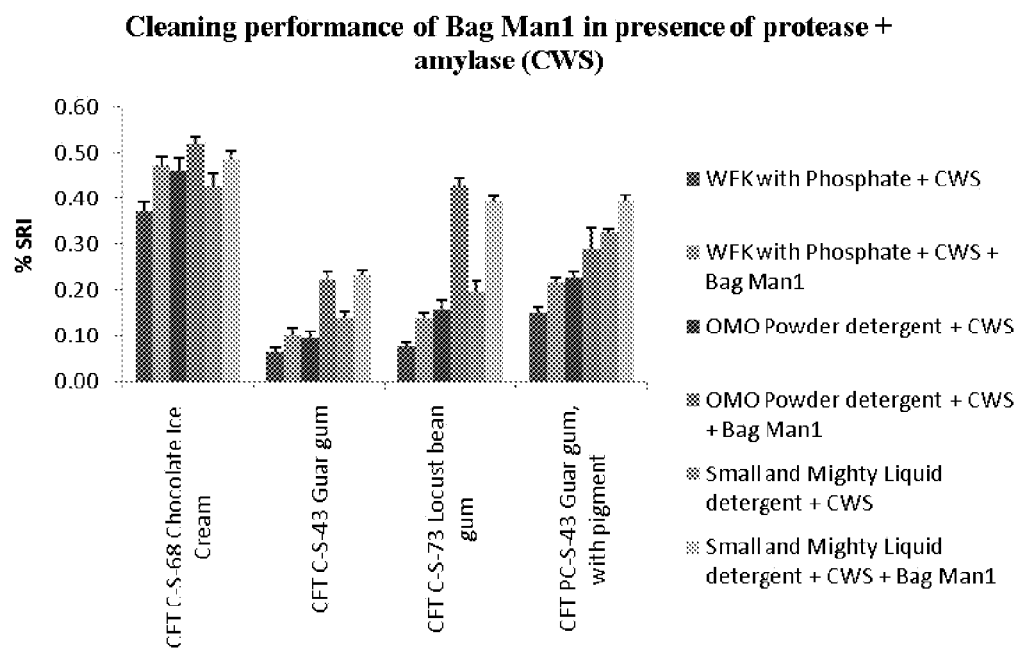
FIG. 3 shows the cleaning performance of Bag Man 1 in the presence of a protease and an amylase.

Additional experiments were performed to test the cleaning performance of Bag Man1 in a Launder-O-meter LP-2 (Atlas Electric Devices Co., Chicago, Ill.) or equivalent using the CS-43 (Guar Gum), CS-73 (Locust Bean Gum), PCS-43 (pigment stained Guar Gum), and CFT CS-68 (Chocolate Ice Cream) swatches purchased from Center for Testmaterials, Netherlands. The cleaning performance of Bag Man1 was tested at 1 ppm in combination with a protease (PURAFECT®, PURAFECT® Prime, or EXCELLASE®) and an amylase (ACE prime described in WO2010/115021, POWERASE®, or POWERASE® 1600HS). The assay was performed as described above using heat-inactivated commercially available OMO color powder detergent (Unilever) at a dose of 5.25 g/L, commercially available Small and Mighty bio liquid detergent (Unilever) containing no enzymes at a dose of 2.33 g/L, and phosphate-containing IEC-60436 WFK Type C Detergent without the presence of enzymes (www.testgewebe.de/en/products/detergents/) at 3 g/L. For powder detergent, PURAFECT® was used at 0.8 ppm and POWERASE® at 0.2 ppm, for liquid detergent, PURAFECT® Prime was used at 0.5 ppm and ACE prime at 0.1 ppm, and for WFK detergent, EXCELLASE® was used at 48 ppm of the granule product and POWERASE® 1600HS was used at 15 ppm of granule product. The % SRI readings (±95% confidence interval) for the cleaning performance are shown in FIG. 3.

Example 4 pH Profile of Bag Man1

Figure 4A:
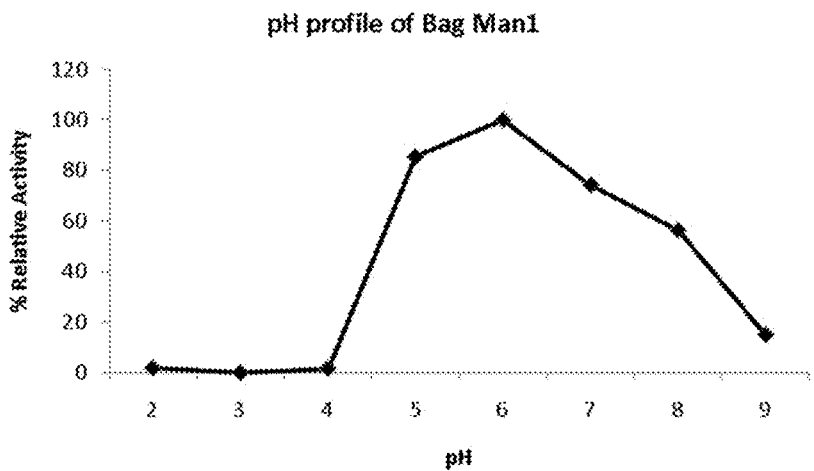
FIG. 4A provides a pH profile of Bag Man1.

The pH profile of purified Bag Man1 (SEQ ID NO. 7) was determined using the beta-mannazyme tablet assay from Megazyme (TMNZ 1/02; Azurine-crosslinked carob galactomannan) with minor modifications to the suggested protocol. The assay was performed in 50 mM Acetate/Bis-Tris/HEPES/CHES buffer adjusted to pH values between 4 and 11. The enzyme solution was diluted to a final concentration of 1 ppm into the assay buffer, and 500 µL of the enzyme solution was equilibrated at 40° C. before adding one substrate tablet. After 10 minutes, the reaction was stopped by adding 10 mL of 2% Tris pH 12 solution. The tubes were left at room temperature for five minutes, stirred and the liquid filtered through a Whatman No. 1 paper filter. Release of blue dye from the substrate was quantified by measuring the optical density at 590 nm. Enzyme activity at each pH is reported as relative activity where the activity at the pH optimum was set to 100%. The pH profile of Bag Man1 is shown in FIG. 4A. Bag Man1 was found to have an optimum at about pH 6, and was found to retain greater than 70% relative activity between pH 4.8 to 7.4. This is in contrast to a previously described mannanase obtained from *Bacillus* strain C11SB.G17, which was found to have a pH optimum of about 9 (see, e.g., EP 0 766 727 B1, and U.S. Pat. No. 6,602,842).

Figure 4B:
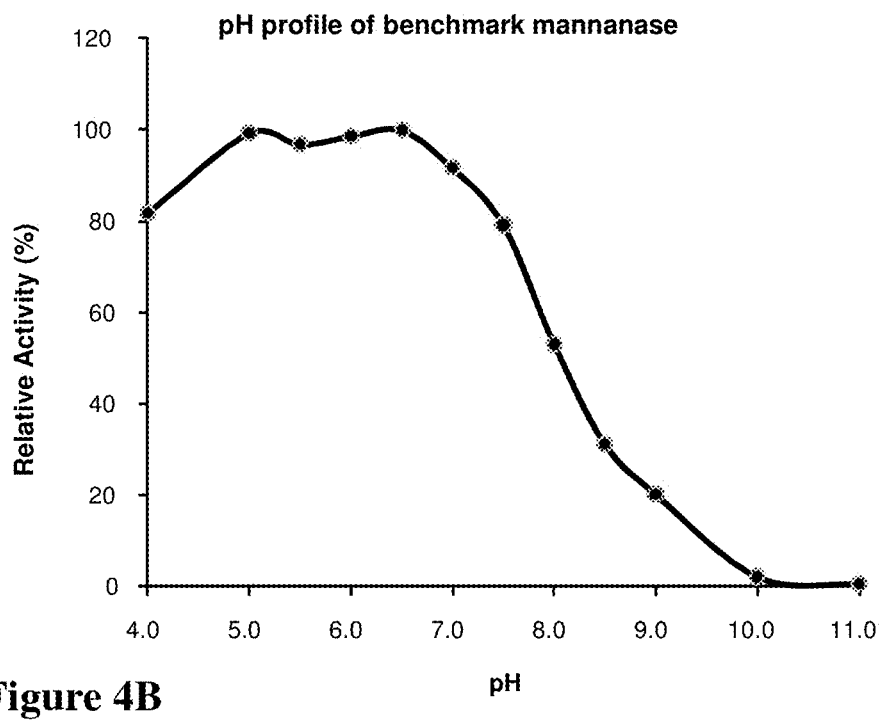
FIG. 4B provides a pH profile for a benchmark endo-β-mannanase (Mannastar™).

The pH profile of Mannastar™ was studied by assaying for mannanase activity at varying pH values ranging from 4-11 using the beta-mannazyme tablet assay (Megazyme, Ireland). The generation of water soluble dye fragments was monitored after 10 min at OD 590 nm at each pH value. A pH profile plot was made by setting the highest OD value for activity to 100 and determining the activity at the other pH values relative to the highest OD value. The pH profile of Mannastar™ is shown in FIG. 4B. Mannastar™ was found to retain greater than 70% of maximum activity between pH 4 and 7.5.

Example 5

Temperature Profile of Bag Man1

Figure 5A:
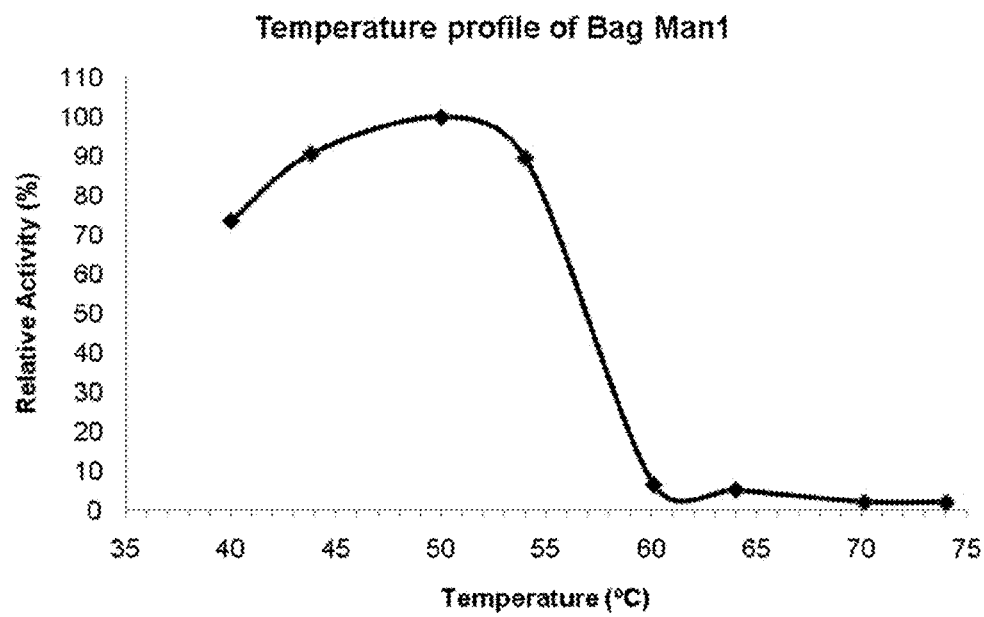
FIG. 5A provides a temperature profile of Bag Man1.

The temperature optimum of purified Bag Man1 (SEQ ID No.7) was determined by assaying enzyme activity at a concentration of 1 ppm at temperatures varying between 35° C. and 75° C. for 10 minutes in 50 mM sodium citrate buffer at pH 6. The activity is reported as relative activity where the activity at the temperature optimum was set to 100%. The temperature profile of Bag Man1 is shown in FIG. 5A. Bag Man1 was found to have an optimum temperature of about 50° C., and was found to retain greater than 70% relative activity between 40° C. and 55° C.

Figure 5B:
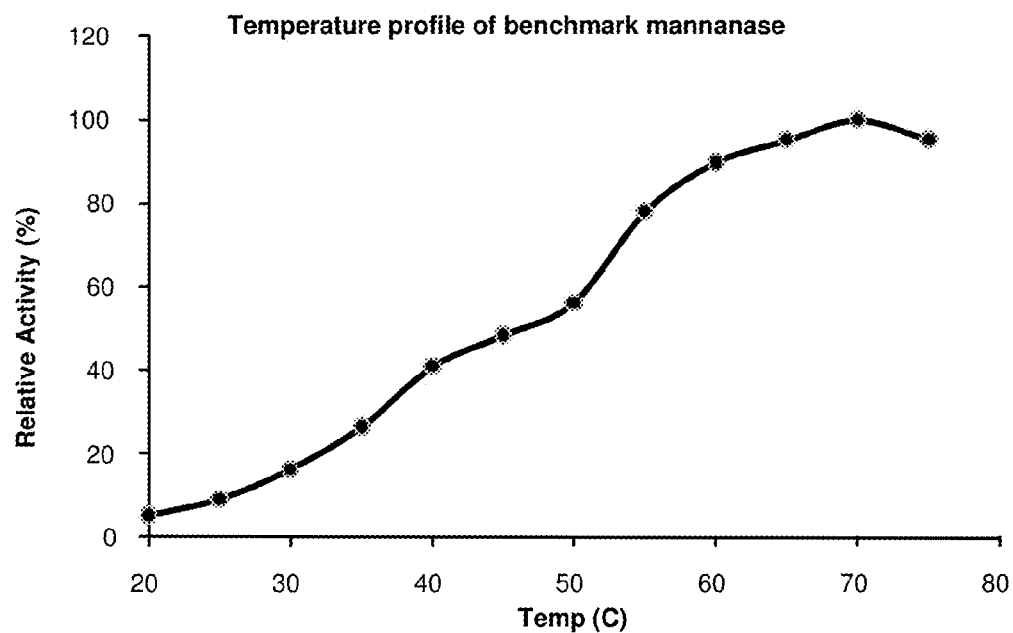
FIG. 5B provides a temperature profile of a benchmark endo-β-mannanase (Mannastar™).

The temperature profile of Mannastar™ was studied by assaying for mannanase activity at varying temperatures ranging from 20° C. to 75° C. using the beta-mannazyme tablet assay (Megazyme, Ireland) in 50 mM sodium acetate buffer at pH 6. The generation of water soluble dye fragments was monitored after 10 min at OD 590 nm at each temperature. The temperature profile was made by setting the highest OD value for activity to 100% and determining the activity at the other temperatures relative to the maximum. The temperature profile of Mannastar™ is shown in FIG. 5B. Mannastar™ was found to retain greater than 70% maximum activity 55° C. and 75° C.

Example 6

Mannanase Activity of Bag Man1

Figure 6A:
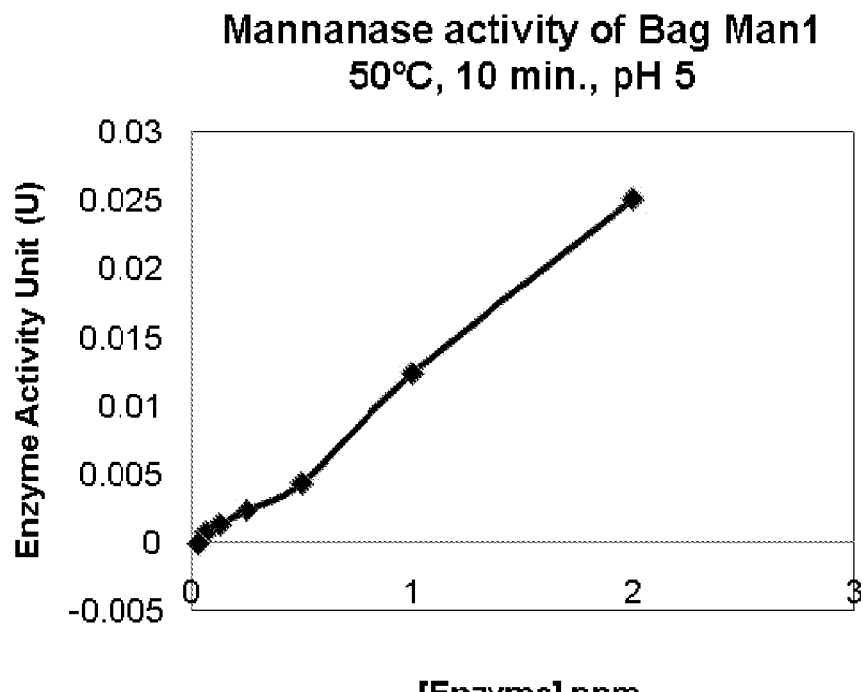
FIG. 6A shows the mannanase activity of Bag Man1 at 50° C., for 10 min at pH 5.
Figure 6B:
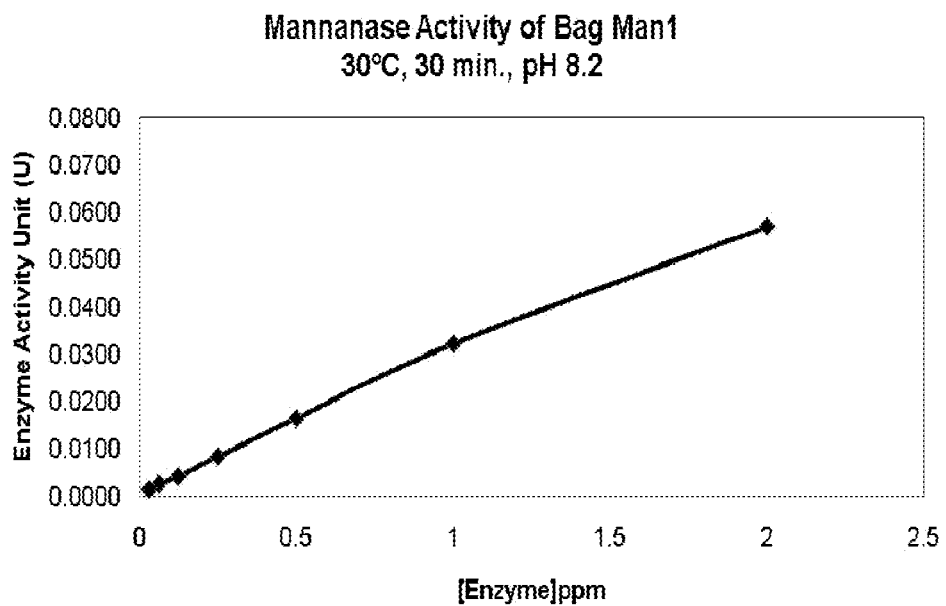
FIG. 6B shows the mannanase activity of Bag Man1 at 30° C., for 30 min at pH 8.2.

Bag Man1 (EC number 3.2.1.78) belongs to the CAZy number GH26 glycosyl hydrolase family. The beta 1-4 mannanase activity of Bag Man1 was measured using 1% Megazyme Low Viscosity Carob Galactomannan (Megazyme International, Ireland Lot #9030) as substrate in a PAHBAH assay (Lever, Anal. Biochem. 47:248, 1972). The assay was performed either in 50 mM sodium acetate pH5, 0.005% Tween-80 buffer at 50° C. for 10 minutes or 50 mM HEPES pH8.2, 0.005% Tween-80 buffer at 30° C. for 30 minutes. A standard curve using mannose was created for each buffer and used to calculate enzyme activity units Enzyme Specific Activity Unit Definition: One mannanase unit is defined as the amount of enzyme required to generate 1 umole of mannose reducing sugar equivalents per minute under the conditions of the assay. The mannanase activity of Bag Man1 under different conditions is shown in FIGS. 6A and 6B.

The specific activity of Mannastar™ was determined with a beta-mannazyme tablet assay (Megazyme, Ireland) using Azurine-crosslinked carob galactomannan as a substrate at pH 8.0 (50 mM Acetate/Bis-Tris/HEPES/CHES). The generation of water soluble dye fragments was monitored after 10 min at OD 590 nm. A standard curve of purified *A. niger* 1,4-β-mannanase was used to convert absorbance values to units and the specific activity was calculated to be 20.6 U/mg protein. One Unit of activity is defined as the amount of enzyme required to release one micromole of mannose reducing-sugar equivalents per minute under the defined assay conditions.

Example 7

Comparison of Bag Man1 to Other Mannanases

A. Identification of Homologous Mannanases
Homologs were identified by a BLAST search (Altschul et al., Nucleic Acids Res, 25:3389-402, 1997) against the NCBI non-redundant protein database, nr, using the mature protein amino acid sequence for Bag Man1 as query sequence (SEQ ID NO:6). Only sequences having a percent identity of 40% or greater were retained. Percent identity (PID) is defined as the number of identical residues divided by the number of aligned residues in the pairwise alignment. Table 7-1 provides a list of sequences having a percent identity of 40% or greater to Bag Man1. Table 7-1 provides NCBI and SEQ ID NOs for each homolog, as well as the length in amino acids of each protein sequence, and the PID (percent identity).
B. Alignment of Homologous Mannanase Sequences
The amino acid sequence of Bag Man1 and selected homologs were aligned using CLUSTALW software (Thompson et al., Nucleic Acids Research, 22:4673-4680, 1994) using default parameters. Alignments were subsequently refined with MUSCLE (Edgar, Nucleic Acids Res, 32:1792-1797, 2004) using default parameters. For homologous sequences, only regions that correspond to seed sequences are shown. Redundant sequences with a PID of 98% or higher to a listed sequence were excluded from further analysis. FIG. 7 shows the alignment of Bag Man1 with other mannanase sequences.

C. Phylogenetic Tree

Figure 8:
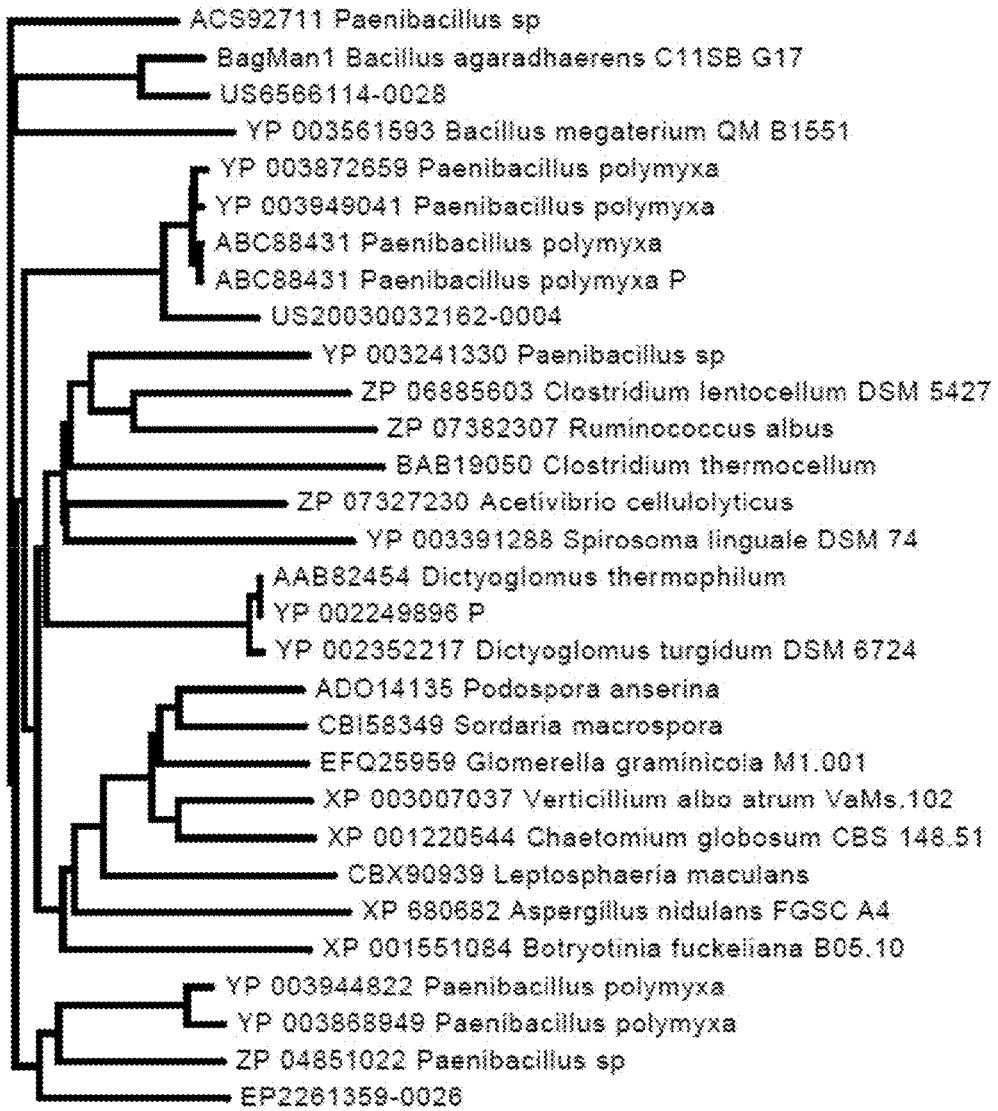
FIG. 8 provides a phylogenetic tree for Bag Man1.

A phylogenetic tree was built for Bag Man1 with the Neighbor-Joining algorithm using ClustalW software with 10000 bootstraps based on the refined alignments described above. Bootstrapping was used to assess the reliability of the tree branches (Felsenstein, *Evolution* 39:783-791, 1985). Other ClustalW parameters were set at the default values. The phylogenetic tree was rendered by the program PhyloWidget (Jordan and Piel, Bioinformatics, 24:1641-1642, 2008; and www.phylowidget.org). FIG. 8 depicts the phylogentic tree built for Bag Man1 mannanase.

TABLE 7-1

List of Bag Man1 Homologs with Percent Identity of 40 or greater to the Mature Form of SEQ ID NO: 6.

| Homolog | SEQ ID NO: | LENGTH (# residues) | % IDENTITY (PID) |
|---|---|---|---|
| US6566114-0028 | 11 | 496 | 83.0 |
| YP_003872659 | 12 | 1353 | 57.5 |
| YP_003949041 | 13 | 1373 | 57.3 |
| ABC88431 | 14 | 1352 | 56.4 |
| ABC88431_P | 15 | 1352 | 56.4 |
| ACS92711 | 16 | 475 | 54.8 |
| YP_003241330 | 17 | 338 | 54.6 |
| AAB82454 | 18 | 398 | 53.7 |
| YP_002249896_P | 19 | 398 | 53.7 |
| ZP_04851022 | 20 | 645 | 53.4 |
| EP2261359-0026 | 21 | 815 | 53.2 |
| US20030032162-0004 | 22 | 1350 | 53.1 |
| YP_003868949 | 23 | 656 | 52.8 |
| YP_003944822 | 24 | 656 | 52.5 |
| YP_002352217 | 25 | 469 | 51.9 |
| YP_003561593 | 26 | 479 | 51.0 |
| ZP_07327230 | 27 | 558 | 50.1 |
| XP_003007037 | 28 | 442 | 48.4 |
| ADO14135 | 29 | 449 | 48.1 |
| XP_001220544 | 30 | 476 | 47.4 |
| ZP_06885603 | 31 | 834 | 46.6 |
| EFQ25959 | 32 | 472 | 45.9 |
| XP_680682 | 33 | 355 | 45.8 |
| YP_003391288 | 34 | 584 | 45.7 |
| CBI58349 | 35 | 466 | 45.6 |
| XP_001551084 | 36 | 471 | 45.1 |
| CBX90939 | 37 | 461 | 44.4 |
| BAB19050 | 38 | 591 | 44.0 |
| ZP_07382307 | 39 | 553 | 43.1 |

TABLE 7-2

List of BagMan1 Homologs with a Percent Identity of 40 or Greater to the Catalytic Domain (306 residues) of SEQ ID NO: 10

| Homolog | Length | PID (%) |
|---|---|---|
| US6566114-0028 | 496 | 88.6 |
| YP_003949041 | 1373 | 66.1 |
| ABC88431 | 1352 | 66.1 |
| ABC88431_P | 1352 | 66.1 |
| YP_003872659 | 1353 | 65.8 |
| ACS92711 | 475 | 64.1 |
| ZP_04851022 | 645 | 63.8 |
| YP_003944822 | 656 | 63.5 |
| YP_003868949 | 656 | 63.1 |
| EP2261359-0026 | 815 | 60.8 |
| US20030032162-0004 | 1350 | 60.5 |
| YP_003561593 | 479 | 59.8 |
| YP_002352217 | 469 | 59.1 |
| AAB82454 | 398 | 58.5 |
| YP_002249896_P | 398 | 58.5 |
| ZP_07327230 | 558 | 56.8 |
| YP_003241330 | 338 | 55.7 |
| ADO14135 | 449 | 54.8 |
| XP_001220544 | 476 | 52.8 |

TABLE 7-2-continued

List of BagMan1 Homologs with a Percent Identity of 40 or Greater to the Catalytic Domain (306 residues) of SEQ ID NO: 10

| Homolog | Length | PID (%) |
|---|---|---|
| XP_003007037 | 442 | 52.2 |
| CBI58349 | 466 | 52.2 |
| ZP_06885603 | 834 | 51.3 |
| YP_003391288 | 584 | 50.8 |
| EFQ25959 | 472 | 50.5 |
| XP_001551084 | 471 | 50 |
| CBX90939 | 461 | 49.7 |
| BAB19050 | 591 | 49 |
| ZP_07382307 | 553 | 48.7 |
| XP_680682 | 355 | 48.3 |

Example 8

Identification of the Catalytic Domain of Bag Man1

The location of structural and functional domains (e.g., catalytic region and carbohydrate binding domains) of Bag Man1 was defined using reference sequences within the BLAST result list of Example 7 and the Conserved Domain Search Service (CD Search) tool located in the NCBI web site. CD Search uses RPS-BLAST (Reverse Position-Specific BLAST) to compare a query sequence against position-specific score matrices that have been prepared from conserved domain alignments present in the Conserved Domain Database (CDD). The results of CD-Search are presented as an annotation of protein domains on the user query sequence, as shown in FIG. 9. As a reference for Bag Man1, the protein sequence of homolog YP_003872659 (57.5% identity) was used.

Domains were predicted using ClustalW alignments between Bag Man1 and the previously noted homologs using AlignX within Vector NTI (Invitrogen). Based on the alignment with YP_003872659, the catalytic domain of Bag Man1 was predicted to start at position 1141 and end with E446 (e.g., 306 residue domain). Catalytic residues of Bag Man1 were predicted to be E303 and E395 based on conserved glutamic acid residues contained within the initial pairwise alignment previously described. All the positions were calculated from the start of the native mature protein sequence (SEQ ID NO:6).

The amino acid sequence of the catalytic domain of Bag Man 1 is set forth as SEQ ID NO:10: INPNATDEAKVLM-SYLVDNFGEKILSGQHDFPNTRPDDLEYIYEITGKYP AILGLDFIDNSPSRVEYGAFADETPVAINWWNKGGIV TFTWHWNAPKDLLDEPGNEWWRGFYTEATTFDVE YALNHPDSEDYKLLIRDIDVIADELKKLQKADVPVLW RPLHEAEGKWFWWGKKGPEPAKELWLLMYDRMTN YHNLNNLIWVWNSIEEDWYPGDEYVDIVSFDSYPG DYNYSPMSGQYEALKELSSNKKIIAIAENGPIPDPDL LQRYHAHYSWFTTWNGDILREQNSEEHLKNVYNHD YVITLDE.

Example 9

Liquid Laundry Detergent Compositions Comprising Bag Man1

In this example, various formulations for liquid laundry detergent compositions are provided. In each of these formulations, Bag Man1 is included at a concentration of from about 0.0001 to about 10 weight percent. In some alternative embodiments, other concentrations will find use, as determined by the formulator, based on their needs.

TABLE 9-1

Liquid Laundry Detergent Compositions

| Compound | Formulations | | | | |
|---|---|---|---|---|---|
| | I | II | III | IV | V |
| LAS | 24.0 | 32.0 | 6.0 | 3.0 | 6.0 |
| NaC$_{16}$-C$_{17}$ HSAS | — | — | — | 5.0 | — |
| C$_{12}$-C$_{15}$ AE$_{1.8}$S | — | — | 8.0 | 7.0 | 5.0 |
| C$_8$-C$_{10}$ propyl dimethyl amine | 2.0 | 2.0 | 2.0 | 2.0 | 1.0 |
| C$_{12}$-C$_{14}$ alkyl dimethyl amine oxide | — | — | — | — | 2.0 |
| C$_{12}$-C$_{15}$ AS | — | — | 17.0 | — | 8.0 |
| CFAA | — | 5.0 | 4.0 | 4.0 | 3.0 |
| C$_{12}$-C$_{14}$ Fatty alcohol ethoxylate | 12.0 | 6.0 | 1.0 | 1.0 | 1.0 |
| C$_{12}$-C$_{18}$ Fatty acid | 3.0 | — | 4.0 | 2.0 | 3.0 |
| Citric acid (anhydrous) | 4.5 | 5.0 | 3.0 | 2.0 | 1.0 |
| DETPMP | — | — | 1.0 | 1.0 | 0.5 |
| Monoethanolamine | 5.0 | 5.0 | 5.0 | 5.0 | 2.0 |
| Sodium hydroxide | — | — | 2.5 | 1.0 | 1.5 |
| 1N HCl aqueous solution | #1 | #1 | — | — | — |
| Propanediol | 12.7 | 14.5 | 13.1 | 10. | 8.0 |
| Ethanol | 1.8 | 2.4 | 4.7 | 5.4 | 1.0 |
| DTPA | 0.5 | 0.4 | 0.3 | 0.4 | 0.5 |
| Pectin Lyase | — | — | — | 0.005 | — |
| Amylase | 0.001 | 0.002 | — | — | — |
| Cellulase | — | — | 0.0002 | — | 0.0001 |
| Lipase | 0.1 | — | 0.1 | — | 0.1 |
| NprE (optional) | 0.05 | 0.3 | — | 0.5 | 0.2 |
| PMN | — | — | 0.08 | — | — |
| Protease A (optional) | — | — | — | — | 0.1 |
| Aldose Oxidase | — | — | 0.3 | — | 0.003 |
| ZnCl2 | 0.1 | 0.05 | 0.05 | 0.05 | 0.02 |
| Ca formate | 0.05 | 0.07 | 0.05 | 0.06 | 0.07 |
| DETBCHD | — | — | 0.02 | 0.01 | — |
| SRP1 | 0.5 | 0.5 | — | 0.3 | 0.3 |
| Boric acid | — | — | — | — | 2.4 |
| Sodium xylene sulfonate | — | — | 3.0 | — | — |
| Sodium cumene sulfonate | — | — | — | 0.3 | 0.5 |
| DC 3225C | 1.0 | 1.0 | 1.0 | 1.0 | 1.0 |
| 2-butyl-octanol | 0.03 | 0.04 | 0.04 | 0.03 | 0.03 |
| Brightener 1 | 0.12 | 0.10 | 0.18 | 0.08 | 0.10 |
| Balance to 100% perfume/dye and/or water | | | | | |

1: Add 1N HCl aq. soln to adjust the neat pH of the formula in the range from about 3 to about 5. The pH of Examples 9(I)-(II) is about 5 to about 7, and of 9(III)-(V) is about 7.5 to about 8.5.

Example 10

Liquid Hand Dishwashing Detergent Compositions Comprising Bag Man1

In this example, various hand dish liquid detergent formulations are provided. In each of these formulations, Bag Man1 is included at a concentration of from about 0.0001 to about 10 weight percent. In some alternative embodiments, other concentrations will find use, as determined by the formulator, based on their needs.

TABLE 10-1

Liquid Hand Dishwashing Detergent Compositions

| Compound | Formulations | | | | | |
|---|---|---|---|---|---|---|
| | I | II | III | IV | V | VI |
| C$_{12}$-C$_{15}$ AE$_{1.8}$S | 30.0 | 28.0 | 25.0 | — | 15.0 | 10.0 |
| LAS | — | — | — | 5.0 | 15.0 | 12.0 |
| Paraffin Sulfonate | — | — | — | 20.0 | — | — |
| C$_{10}$-C$_{18}$ Alkyl Dimethyl Amine Oxide | 5.0 | 3.0 | 7.0 | — | — | — |
| Betaine | 3.0 | — | 1.0 | 3.0 | 1.0 | — |
| C$_{12}$ poly-OH fatty acid amide | — | — | — | 3.0 | 1.0 | — |
| C$_{14}$ poly-OH fatty acid amide | — | 1.5 | — | — | — | — |
| C$_{11}$E$_9$ | 2.0 | — | 4.0 | — | — | 20.0 |
| DTPA | — | — | — | — | 0.2 | — |
| Tri-sodium Citrate dehydrate | 0.25 | — | — | 0.7 | — | — |
| Diamine | 1.0 | 5.0 | 7.0 | 1.0 | 5.0 | 7.0 |
| MgCl$_2$ | 0.25 | — | — | 1.0 | — | — |
| nprE (optional) | 0.02 | 0.01 | — | 0.01 | — | 0.05 |
| PMN | — | — | 0.03 | — | 0.02 | — |
| Protease A (optional) | — | 0.01 | — | — | — | — |
| Amylase | 0.001 | — | — | 0.002 | — | 0.001 |
| Aldose Oxidase | 0.03 | — | 0.02 | — | 0.05 | — |
| Sodium Cumene Sulphonate | — | — | — | 2.0 | 1.5 | 3.0 |
| PAAC | 0.01 | 0.01 | 0.02 | | | |
| DETBCHD | — | — | — | 0.01 | 0.02 | 0.01 |
| Balance to 100% perfume/dye and/or water | | | | | | |

The pH of Examples 10(I)-(VI) is about 8 to about 11

Example 11

Liquid Automatic Dishwashing Detergent Compositions Comprising Bag Man1

In this example, various liquid automatic dishwashing detergent formulations are provided. In each of these formulations, Bag Man1 polypeptide is included at a concentration of from about 0.0001 to about 10 weight percent. In some alternative embodiments, other concentrations will find use, as determined by the formulator, based on their needs.

TABLE 11-1

Liquid Automatic Dishwashing Detergent Compositions

| Compound | Formulations | | | | |
|---|---|---|---|---|---|
| | I | II | III | IV | V |
| STPP | 16 | 16 | 18 | 16 | 16 |
| Potassium Sulfate | — | 10 | 8 | — | 10 |
| 1,2 propanediol | 6.0 | 0.5 | 2.0 | 6.0 | 0.5 |
| Boric Acid | — | — | — | 4.0 | 3.0 |
| CaCl$_2$ dihydrate | 0.04 | 0.04 | 0.04 | 0.04 | 0.04 |
| Nonionic | 0.5 | 0.5 | 0.5 | 0.5 | 0.5 |
| nprE (optional) | 0.1 | 0.03 | — | 0.03 | — |
| PMN | — | — | 0.05 | — | 0.06 |
| Protease B (optional) | — | — | — | 0.01 | — |
| Amylase | 0.02 | — | 0.02 | 0.02 | — |
| Aldose Oxidase | — | 0.15 | 0.02 | — | 0.01 |
| Galactose Oxidase | — | — | 0.01 | — | 0.01 |
| PAAC | 0.01 | — | — | 0.01 | — |
| DETBCHD | — | 0.01 | — | — | 0.01 |
| Balance to 100% perfume/dye and/or water | | | | | |

Example 12

Granular and/or Tablet Laundry Compositions Comprising Bag Man1

This example provides various formulations for granular and/or tablet laundry detergents. In each of these formulations, Bag Man1 is included at a concentration of from about 0.0001 to about 10 weight percent. In some alternative embodiments, other concentrations will find use, as determined by the formulator, based on their needs.

TABLE 12-1

Granular and/or Tablet Laundry Compositions

| Compound Base Product | I | II | III | IV | V |
|---|---|---|---|---|---|
| $C_{14}$-$C_{15}$AS or TAS | 8.0 | 5.0 | 3.0 | 3.0 | 3.0 |
| LAS | 8.0 | — | 8.0 | — | 7.0 |
| $C_{12}$-$C_{15}$AE$_3$S | 0.5 | 2.0 | 1.0 | — | — |
| $C_{12}$-$C_{15}$E$_5$ or E$_3$ | 2.0 | — | 5.0 | 2.0 | 2.0 |
| QAS | — | — | — | 1.0 | 1.0 |
| Zeolite A | 20.0 | 18.0 | 11.0 | — | 10.0 |
| SKS-6 (dry add) | — | — | 9.0 | — | — |
| MA/AA | 2.0 | 2.0 | 2.0 | — | — |
| AA | — | — | — | — | 4.0 |
| 3Na Citrate 2H$_2$O | — | 2.0 | — | — | — |
| Citric Acid (Anhydrous) | 2.0 | — | 1.5 | 2.0 | — |
| DTPA | 0.2 | 0.2 | — | — | — |
| EDDS | — | — | 0.5 | 0.1 | — |
| HEDP | — | — | 0.2 | 0.1 | — |
| PB1 | 3.0 | 4.8 | — | — | 4.0 |
| Percarbonate | — | — | 3.8 | 5.2 | — |
| NOBS | 1.9 | — | — | — | — |
| NACA OBS | — | — | 2.0 | — | — |
| TAED | 0.5 | 2.0 | 2.0 | 5.0 | 1.00 |
| BB1 | 0.06 | — | 0.34 | — | 0.14 |
| BB2 | — | 0.14 | — | 0.20 | — |
| Anhydrous Na Carbonate | 15.0 | 18.0 | — | 15.0 | 15.0 |
| Sulfate | 5.0 | 12.0 | 5.0 | 17.0 | 3.0 |
| Silicate | — | 1.0 | — | — | 8.0 |
| nprE (optional) | 0.03 | — | 0.1 | 0.06 | — |
| PMN | — | 0.05 | — | — | 0.1 |
| Protease B (optional) | — | 0.01 | — | — | — |
| Protease C (optional) | — | — | — | 0.01 | — |
| Lipase | — | 0.008 | — | — | — |
| Amylase | 0.001 | — | — | — | 0.001 |
| Cellulase | — | 0.0014 | — | — | — |
| Pectin Lyase | 0.001 | 0.001 | 0.001 | 0.001 | 0.001 |
| Aldose Oxidase | 0.03 | — | 0.05 | — | — |
| PAAC | — | 0.01 | — | — | 0.05 |
| Balance to 100% Moisture and/or Minors* | | | | | |

*Perfume, dye, brightener/SRP1/Na carboxymethylcellulose/photobleach/MgSO$_4$/PVPVI/suds suppressor/high molecular PEG/clay.

Example 13

Additional Liquid Laundry Detergents Comprising Bag Man1

This example provides further formulations for liquid laundry detergents. In each of these formulations, Bag Man1 is included at a concentration of from about 0.0001 to about 10 weight percent. In some alternative embodiments, other concentrations will find use, as determined by the formulator, based on their needs.

TABLE 13-1

Liquid Laundry Detergents

| Compound | IA | IB | II | III | IV | V |
|---|---|---|---|---|---|---|
| LAS | 11.5 | 11.5 | 9.0 | — | 4.0 | — |
| $C_{12}$-$C_{15}$AE$_{2.85}$S | — | — | 3.0 | 18.0 | — | 16.0 |
| $C_{14}$-$C_{15}$E$_{2.5}$ S | 11.5 | 11.5 | 3.0 | — | 16.0 | — |
| $C_{12}$-$C_{13}$E$_9$ | — | — | 3.0 | 2.0 | 2.0 | 1.0 |
| $C_{12}$-$C_{13}$E$_7$ | 3.2 | 3.2 | — | — | — | — |
| CFAA | — | — | — | 5.0 | — | 3.0 |
| TPKFA | 2.0 | 2.0 | — | 2.0 | 0.5 | 2.0 |
| Citric Acid (Anhy.) | 3.2 | 3.2 | 0.5 | 1.2 | 2.0 | 1.2 |
| Ca formate | 0.1 | 0.1 | 0.06 | 0.1 | — | — |
| Na formate | 0.5 | 0.5 | 0.06 | 0.1 | 0.05 | 0.05 |
| ZnC12 | 0.1 | 0.05 | 0.06 | 0.03 | 0.05 | 0.05 |
| Na Culmene Sulfonate | 4.0 | 4.0 | 1.0 | 3.0 | 1.2 | — |
| Borate | 0.6 | 0.6 | 1.5 | — | — | — |
| Na Hydroxide | 6.0 | 6.0 | 2.0 | 3.5 | 4.0 | 3.0 |
| Ethanol | 2.0 | 2.0 | 1.0 | 4.0 | 4.0 | 3.0 |
| 1,2 Propanediol | 3.0 | 3.0 | 2.0 | 8.0 | 8.0 | 5.0 |
| Monoethanol-amine | 3.0 | 3.0 | 1.5 | 1.0 | 2.5 | 1.0 |
| TEPAE | 2.0 | 2.0 | — | 1.0 | 1.0 | 1.0 |
| nprE (optional) | 0.03 | 0.05 | — | 0.03 | — | 0.02 |
| PMN | — | — | 0.01 | — | 0.08 | — |
| Protease A (optional) | — | — | 0.01 | — | — | — |
| Lipase | — | — | — | 0.002 | — | — |
| Amylase | — | — | — | — | 0.002 | — |
| Cellulase | — | — | — | — | — | 0.0001 |
| Pectin Lyase | 0.005 | 0.005 | — | — | — | — |
| Aldose Oxidase | 0.05 | — | — | 0.05 | — | 0.02 |
| Galactose oxidase | — | 0.04 | — | — | — | — |
| PAAC | 0.03 | 0.03 | 0.02 | — | — | — |
| DETBCHD | — | — | — | 0.02 | 0.01 | — |
| SRP 1 | 0.2 | 0.2 | — | 0.1 | — | — |
| DTPA | — | — | — | 0.3 | — | — |
| PVNO | — | — | — | 0.3 | — | 0.2 |
| Brightener 1 | 0.2 | 0.2 | 0.07 | 0.1 | — | — |
| Silicone antifoam | 0.04 | 0.04 | 0.02 | 0.1 | 0.1 | 0.1 |
| Balance to 100% perfume/dye and/or water | | | | | | |

Example 14

High Density Dishwashing Detergents Comprising Bag Man1

This example provides various formulations for high density dishwashing detergents. In each of these compact formulations, Bag Man1 is included at a concentration of from about 0.0001 to about 10 weight percent. In some alternative embodiments, other concentrations will find use, as determined by the formulator, based on their needs.

TABLE 14-1

High Density Dishwashing Detergents

| Compound | I | II | III | IV | V | VI |
|---|---|---|---|---|---|---|
| STPP | — | 45.0 | 45.0 | — | — | 40.0 |
| 3Na Citrate 2H$_2$O | 17.0 | — | — | 50.0 | 40.2 | — |
| Na Carbonate | 17.5 | 14.0 | 20.0 | — | 8.0 | 33.6 |
| Bicarbonate | — | — | — | 26.0 | — | — |
| Silicate | 15.0 | 15.0 | 8.0 | — | 25.0 | 3.6 |
| Metasilicate | 2.5 | 4.5 | 4.5 | — | — | — |
| PB 1 | — | — | 4.5 | — | — | — |
| PB4 | — | — | — | 5.0 | — | — |

TABLE 14-1-continued

High Density Dishwashing Detergents

| Compound | \multicolumn{6}{c}{Formulations} | | | | | |
|---|---|---|---|---|---|---|
| | I | II | III | IV | V | VI |
| Percarbonate | — | — | — | — | — | 4.8 |
| BB 1 | — | 0.1 | 0.1 | — | 0.5 | — |
| BB2 | 0.2 | 0.05 | — | 0.1 | — | 0.6 |
| Nonionic | 2.0 | 1.5 | 1.5 | 3.0 | 1.9 | 5.9 |
| HEDP | 1.0 | — | — | — | — | — |
| DETPMP | 0.6 | — | — | — | — | — |
| PAAC | 0.03 | 0.05 | 0.02 | — | — | — |
| Paraffin | 0.5 | 0.4 | 0.4 | 0.6 | — | — |
| nprE (optional) | 0.072 | 0.053 | — | 0.026 | — | 0.01 |
| PMN | — | — | 0.053 | — | 0.059 | — |
| Protease B (optional) | — | — | — | — | — | 0.01 |
| Amylase | 0.012 | — | 0.012 | — | 0.021 | 0.006 |
| Lipase | — | 0.001 | — | 0.005 | — | — |
| Pectin Lyase | 0.001 | 0.001 | 0.001 | — | — | — |
| Aldose Oxidase | 0.05 | 0.05 | 0.03 | 0.01 | 0.02 | 0.01 |
| BTA | 0.3 | 0.2 | 0.2 | 0.3 | 0.3 | 0.3 |
| Polycarboxylate | 6.0 | — | — | — | 4.0 | 0.9 |
| Perfume | 0.2 | 0.1 | 0.1 | 0.2 | 0.2 | 0.2 |
| Balance to 100% Moisture and/or Minors* | | | | | | |

*Brightener/dye/SRP1/Na carboxymethylcellulose/photobleach/MgSO$_4$/VPVI suds suppressor/high molecular PEG/clay.
The pH of Examples 14(I) through (VI) is from about 9.6 to about 11.3.

Example 15

Tablet Dishwashing Detergent Compositions Comprising Bag Man1

This example provides various tablet dishwashing detergent formulations. The following tablet detergent compositions of the present disclosure are prepared by compression of a granular dishwashing detergent composition at a pressure of 13 KN/cm using a standard 12 head rotary press. In each of these formulations, Bag Man1 is included at a concentration of from about 0.0001 to about 10 weight percent. In some alternative embodiments, other concentrations will find use, as determined by the formulator, based on their needs.

TABLE 15-1

Tablet Dishwashing Detergent Compositions

| Compound | I | II | III | IV | V | VI | VII | VIII |
|---|---|---|---|---|---|---|---|---|
| STPP | — | 48.8 | 44.7 | 38.2 | — | 42.4 | 46.1 | 46.0 |
| 3Na Citrate 2H$_2$O | 20.0 | — | — | — | 35.9 | — | — | — |
| Na Carbonate | 20.0 | 5.0 | 14.0 | 15.4 | 8.0 | 23.0 | 20.0 | — |
| Silicate | 15.0 | 14.8 | 15.0 | 12.6 | 23.4 | 2.9 | 4.3 | 4.2 |
| Lipase | 0.001 | — | 0.01 | — | 0.02 | — | — | — |
| Protease B (optional) | 0.01 | — | — | — | — | — | — | — |
| Protease C (optional) | — | — | — | — | — | — | 0.01 | — |
| nprE (optional) | 0.01 | 0.08 | — | 0.04 | — | 0.023 | — | 0.05 |
| PMN | — | — | 0.05 | — | 0.052 | — | 0.023 | — |
| Amylase | 0.012 | 0.012 | 0.012 | — | 0.015 | — | 0.017 | 0.002 |
| Pectin Lyase | 0.005 | — | — | 0.002 | — | — | — | — |
| Aldose Oxidase | — | 0.03 | — | 0.02 | 0.02 | — | 0.03 | — |
| PB1 | — | — | 3.8 | — | 7.8 | — | — | 4.5 |
| Percarbonate | 6.0 | — | — | 6.0 | — | 5.0 | — | — |
| BB1 | 0.2 | — | 0.5 | — | 0.3 | 0.2 | — | — |
| BB2 | — | 0.2 | — | 0.5 | — | — | 0.1 | 0.2 |
| Nonionic | 1.5 | 2.0 | 2.0 | 2.2 | 1.0 | 4.2 | 4.0 | 6.5 |
| PAAC | 0.01 | 0.01 | 0.02 | — | — | — | — | — |
| DETBCHD | — | — | — | 0.02 | 0.02 | — | — | — |
| TAED | — | — | — | — | — | 2.1 | — | 1.6 |
| HEDP | 1.0 | — | — | 0.9 | — | 0.4 | 0.2 | — |
| DETPMP | 0.7 | — | — | — | — | — | — | — |
| Paraffin | 0.4 | 0.5 | 0.5 | 0.5 | — | — | 0.5 | — |
| BTA | 0.2 | 0.3 | 0.3 | 0.3 | 0.3 | 0.3 | 0.3 | — |
| Polycarboxylate | 4.0 | — | — | — | 4.9 | 0.6 | 0.8 | — |
| PEG 400-30,000 | — | — | — | — | — | 2.0 | — | 2.0 |
| Glycerol | — | — | — | — | — | 0.4 | — | 0.5 |
| Perfume | — | — | — | 0.05 | 0.2 | 0.2 | 0.2 | 0.2 |
| Balance to 100% Moisture and/or Minors* | | | | | | | | |

*Brightener/SRP1/Na carboxymethylcellulose/photobleach/MgSO$_4$/PVPVI/suds suppressor/high molecular PEG/clay.
The pH of Examples 15(I) through 15(VII) is from about 10 to about 11.5; pH of 15(VIII) is from 8-10.
The tablet weight of Examples 15(I) through 15(VIII) is from about 20 grams to about 30 grams.

Example 16

Liquid Hard Surface Cleaning Detergents Comprising Bag Man1

This example provides various formulations for liquid hard surface cleaning detergents. In each of these formulations, Bag Man1 is included at a concentration of from about 0.0001 to about 10 weight percent. In some alternative embodiments, other concentrations will find use, as determined by the formulator, based on their needs.

TABLE 16-1

Liquid Hard Surface Cleaning Detergents

| Compound | I | II | III | IV | V | VI | VII |
|---|---|---|---|---|---|---|---|
| $C_9$-$C_{11}E_5$ | 2.4 | 1.9 | 2.5 | 2.5 | 2.5 | 2.4 | 2.5 |
| $C_{12}$-$C_{14}E_5$ | 3.6 | 2.9 | 2.5 | 2.5 | 2.5 | 3.6 | 2.5 |
| $C_7$-$C_9E_6$ | — | — | — | — | 8.0 | — | — |
| $C_{12}$-$C_{14}E_{21}$ | 1.0 | 0.8 | 4.0 | 2.0 | 2.0 | 1.0 | 2.0 |
| LAS | — | — | — | 0.8 | 0.8 | — | 0.8 |
| Sodium cumene sulfonate | 1.5 | 2.6 | — | 1.5 | 1.5 | 1.5 | 1.5 |
| Isachem ® AS | 0.6 | 0.6 | — | — | — | 0.6 | — |
| Na$_2$CO$_3$ | 0.6 | 0.13 | 0.6 | 0.1 | 0.2 | 0.6 | 0.2 |
| 3Na Citrate 2H$_2$O | 0.5 | 0.56 | 0.5 | 0.6 | 0.75 | 0.5 | 0.75 |
| NaOH | 0.3 | 0.33 | 0.3 | 0.3 | 0.5 | 0.3 | 0.5 |
| Fatty Acid | 0.6 | 0.13 | 0.6 | 0.1 | 0.4 | 0.6 | 0.4 |
| 2-butyl octanol | 0.3 | 0.3 | — | 0.3 | 0.3 | 0.3 | 0.3 |
| PEG DME-2000 ® | 0.4 | — | 0.3 | 0.35 | 0.5 | — | — |
| PVP | 0.3 | 0.4 | 0.6 | 0.3 | 0.5 | — | — |
| MME PEG (2000) ® | — | — | — | — | — | 0.5 | 0.5 |
| Jeffamine ® ED-2001 | — | 0.4 | — | — | 0.5 | — | — |
| PAAC | — | — | — | 0.03 | 0.03 | 0.03 | — |
| DETBCHD | 0.03 | 0.05 | 0.05 | — | — | — | — |
| nprE (optional) | 0.07 | — | 0.08 | 0.03 | — | 0.01 | 0.04 |
| PMN | — | 0.05 | — | — | 0.06 | — | — |
| Protease B (optional) | — | — | — | — | — | 0.01 | — |
| Amylase | 0.12 | 0.01 | 0.01 | — | 0.02 | — | 0.01 |

TABLE 16-1-continued

Liquid Hard Surface Cleaning Detergents

| Compound | Formulations | | | | | | |
|---|---|---|---|---|---|---|---|
| | I | II | III | IV | V | VI | VII |
| Lipase | — | 0.001 | — | 0.005 | — | 0.005 | — |
| Pectin Lyase | 0.001 | — | 0.001 | — | — | — | 0.002 |
| ZnC12 | 0.02 | 0.01 | 0.03 | 0.05 | 0.1 | 0.05 | 0.02 |
| Calcium Formate | 0.03 | 0.03 | 0.01 | — | — | — | — |

TABLE 16-1-continued

Liquid Hard Surface Cleaning Detergents

| Compound | Formulations | | | | | | |
|---|---|---|---|---|---|---|---|
| | I | II | III | IV | V | VI | VII |
| PB 1 | — | 4.6 | — | 3.8 | — | — | — |
| Aldose Oxidase | 0.05 | — | 0.03 | — | 0.02 | 0.02 | 0.05 |
| Balance to 100% perfume / dye and/or water | | | | | | | |

The pH of Examples 16(I) through (VII) is from about 7.4 to about 9.5.

We claim:

1. An expression vector comprising an isolated nucleic acid encoding a recombinant endo-β-mannanase polypeptide comprising a catalytic domain of an endo-β-mannanase, wherein the catalytic domain is at least 95% identical to the amino acid sequence of SEQ ID NO:10 or a mature from of an endo-β-mannanase, wherein the mature form is at least 90% identical to the amino acid sequence of SEQ ID NO:7, in operable combination to a regulatory sequence.

2. A host cell comprising the expression vector of claim 1.

3. The host cell of claim 2, wherein the host cell is a bacterial cell or a fungal cell.

4. A method of producing an endo-β-mannanase, comprising: culturing the host cell of claim 2 in a culture medium, under suitable conditions to produce a culture comprising the endo-β-mannanase.

5. The method of claim 4, further comprising removing the host cells from the culture by centrifugation, and removing debris of less than 10 kDa by filtration to produce an endo-β-mannanase-enriched supernatant.

6. The expression vector of claim 1, wherein the nucleic acid comprises a sequence that is at least 90% identical to SEQ ID NO:3 with or without an aprE signal sequence.

* * * * *

SEQUENCE LISTING

<160> NUMBER OF SEQ ID NOS: 39

<210> SEQ ID NO 1
<211> LENGTH: 1476
<212> TYPE: DNA
<213> ORGANISM: Bacillus agaradhaerens

<400> SEQUENCE: 1

```
atggaaaata agaaaaaaag atcatttaag aataaggcat taatggttgt tagcattctt      60
atagtaggca ttctcttaat tataatgatt cgaaatatga caaactatga atcagaggtg     120
cgacgatttg aagcagaaga tgctacgttg aatggggtaa cagttaaaaa ttctgaacca     180
ggattttcgg gtactggcta cgtaggtgac tttgaagata gctctcagag tgtgacgttt     240
catgtagatg ttcctgaaac ggatttatac acattaacta tcggctatgg tgcgatttat     300
ggaagtgaaa aagtagccaa tgtccttgta aatggcgaga agctgagctc ttttacaatg     360
ggaagtggat ttggtaaagc ctcagcaggc aacatagtac ttaactcagg ttcgaatact     420
atttcaatta cacctgattg gacacacttt gccattgatt atattgaagt taaacttaca     480
cctgaaccta taaaacataa tgtagagaag aagttaatca atccaaatgc aacggatgaa     540
gccaaagttt taatgagtta cttggtggat aactttggcg aaaaaatcct ttctggacaa     600
catgattttc caaatacaag gccagatgat ttagagtata tttatgaaat tactggaaag     660
tatcctgcta ttttaggttt agactttatt gataatagcc cttcaagagt tgagtatgga     720
gcctttgctg atgaaacacc ggtagcaatc aactggtgga ataaaggggg aattgttacc     780
tttacttggc attggaatgc tcctaaagac ttattggatg aaccaggaaa tgaatggtgg     840
agaggctttt atacagaagc aacaacattc gacgttgaat acgctttaaa tcatccagac     900
tcggaagact ataaactttt aatacgtgat attgatgtga tagctgatga acttaagaaa     960
ttacaaaaag cagatgttcc tgtgttatgg agaccgcttc atgaagcgga gggtaaatgg    1020
ttttggtggg ggaaaaaggg ccctgaacca gctaaggagt tatggctatt aatgtatgac    1080
agaatgacga actatcataa cttaaataat ttaatatggg tatggaactc cattgaagaa    1140
gattggtacc ccggagatga gtatgtggat atagtaagct tcgattccta cccaggtgac    1200
tataactaca gtccaatgag tggtcagtat gaggcgttaa aagagttatc aagtaacaaa    1260
aaaataattg caatagcaga aaatggtcca ataccagatc ctgatttact acaacgttat    1320
catgctcatt atagctggtt tactacgtgg aatggcgaca tattaaggga gcaaaatagt    1380
gaagagcatc tgaagaacgt ctataatcac gattatgtaa ttaccttaga tgaacttcca    1440
gattttgaaa catataagga agacgtaccg ttagag                              1476
```

<210> SEQ ID NO 2
<211> LENGTH: 492

<212> TYPE: PRT
<213> ORGANISM: Bacillus agaradhaerens

<400> SEQUENCE: 2

```
Met Glu Asn Lys Lys Arg Ser Phe Lys Asn Lys Ala Leu Met Val
1               5                   10                  15

Val Ser Ile Leu Ile Val Gly Ile Leu Ile Ile Met Ile Arg Asn
                20                  25                  30

Met Thr Asn Tyr Glu Ser Glu Val Arg Arg Phe Glu Ala Glu Asp Ala
            35                  40                  45

Thr Leu Asn Gly Val Thr Val Lys Asn Ser Glu Pro Gly Phe Ser Gly
50                  55                  60

Thr Gly Tyr Val Gly Asp Phe Glu Asp Ser Ser Gln Ser Val Thr Phe
65                  70                  75                  80

His Val Asp Val Pro Glu Thr Asp Leu Tyr Thr Leu Thr Ile Gly Tyr
                85                  90                  95

Gly Ala Ile Tyr Gly Ser Glu Lys Val Ala Asn Val Leu Val Asn Gly
                100                 105                 110

Glu Lys Leu Ser Ser Phe Thr Met Gly Ser Gly Phe Gly Lys Ala Ser
            115                 120                 125

Ala Gly Asn Ile Val Leu Asn Ser Gly Ser Asn Thr Ile Ser Ile Thr
130                 135                 140

Pro Asp Trp Thr His Phe Ala Ile Asp Tyr Ile Glu Val Lys Leu Thr
145                 150                 155                 160

Pro Glu Pro Ile Lys His Asn Val Glu Lys Leu Ile Asn Pro Asn
                165                 170                 175

Ala Thr Asp Glu Ala Lys Val Leu Met Ser Tyr Leu Val Asp Asn Phe
            180                 185                 190

Gly Glu Lys Ile Leu Ser Gly Gln His Asp Phe Pro Asn Thr Arg Pro
            195                 200                 205

Asp Asp Leu Glu Tyr Ile Tyr Glu Ile Thr Gly Lys Tyr Pro Ala Ile
210                 215                 220

Leu Gly Leu Asp Phe Ile Asp Asn Ser Pro Ser Arg Val Glu Tyr Gly
225                 230                 235                 240

Ala Phe Ala Asp Glu Thr Pro Val Ala Ile Asn Trp Trp Asn Lys Gly
                245                 250                 255

Gly Ile Val Thr Phe Thr Trp His Trp Asn Ala Pro Lys Asp Leu Leu
            260                 265                 270

Asp Glu Pro Gly Asn Glu Trp Trp Arg Gly Phe Tyr Thr Glu Ala Thr
            275                 280                 285

Thr Phe Asp Val Glu Tyr Ala Leu Asn His Pro Asp Ser Glu Asp Tyr
290                 295                 300

Lys Leu Leu Ile Arg Asp Ile Asp Val Ile Ala Asp Glu Leu Lys Lys
305                 310                 315                 320

Leu Gln Lys Ala Asp Val Pro Val Leu Trp Arg Pro Leu His Glu Ala
            325                 330                 335

Glu Gly Lys Trp Phe Trp Trp Gly Lys Lys Gly Pro Glu Pro Ala Lys
            340                 345                 350

Glu Leu Trp Leu Leu Met Tyr Asp Arg Met Thr Asn Tyr His Asn Leu
            355                 360                 365

Asn Asn Leu Ile Trp Val Trp Asn Ser Ile Glu Glu Asp Trp Tyr Pro
370                 375                 380

Gly Asp Glu Tyr Val Asp Ile Val Ser Phe Asp Ser Tyr Pro Gly Asp
385                 390                 395                 400
```

```
Tyr Asn Tyr Ser Pro Met Ser Gly Gln Tyr Glu Ala Leu Lys Glu Leu
                405                 410                 415

Ser Ser Asn Lys Lys Ile Ile Ala Ile Ala Glu Asn Gly Pro Ile Pro
            420                 425                 430

Asp Pro Asp Leu Leu Gln Arg Tyr His Ala His Tyr Ser Trp Phe Thr
        435                 440                 445

Thr Trp Asn Gly Asp Ile Leu Arg Glu Gln Asn Ser Glu Glu His Leu
    450                 455                 460

Lys Asn Val Tyr Asn His Asp Tyr Val Ile Thr Leu Asp Glu Leu Pro
465                 470                 475                 480

Asp Phe Glu Thr Tyr Lys Glu Asp Val Pro Leu Glu
            485                 490

<210> SEQ ID NO 3
<211> LENGTH: 1476
<212> TYPE: DNA
<213> ORGANISM: Artificial Sequence
<220> FEATURE:
<223> OTHER INFORMATION: synthetic Bag Man1 gene from plasmid

<400> SEQUENCE: 3
gtgagaagca aaaaattgtg gatcagcttg ttgtttgcgt aacgttaat ctttacgatg      60 gcgttcagca acatgagcgc gcaggctgct ggaaaaatga caaactatga atcgagggtg    120
cgacgatttg aagcagaaga tgctacgttg aatggggtaa cagttaaaaa ttctgaacca    180 ggatttttcgg gtactggcta cgtaggtgac tttgaagata gctctcagag tgtgacgttt    240
catgtagatg ttcctgaaac ggatttatac acattaacta tcggctatgg tgcgatttat    300
ggaagtgaaa aagtagccaa tgtccttgta aatggcgaga agctgagctc ttttacaatg    360
ggaagtggat ttggtaaagc tcagcaggc aacatagtac ttaactcagg ttcgaatact    420
atttcaatta cacctgattg gacacacttt gccattgatt atattgaagt taaacttaca    480
cctgaaccta taaaacataa tgtagagaag aagttaatca atccaaatgc aacggatgaa    540
gccaaagttt taatgagtta cttggtggat aactttggcg aaaaaatcct ttctggacaa    600
catgattttc caaatacaag gccagatgat ttagagtata tttatgaaat tactggaaag    660
tatcctgcta ttttaggttt agactttatt gataatagcc cttcaagagt tgagtatgga    720
gcctttgctg atgaaacacc ggtagcaatc aactggtgga ataaagggg aattgttacc    780 tttacttggc attggaatgc tcctaaagac ttattggatg aaccaggaaa tgaatggtgg    840
agaggctttt atacagaagc aacaacattc gacgttgaat acgctttaaa tcatccagac    900
tcggaagact ataaactttt aatacgtgat attgatgtga tagctgatga acttaagaaa    960
ttacaaaaag cagatgttcc tgtgttatgg agaccgcttc atgaagcgga gggtaaatgg   1020
ttttggtggg ggaaaaaggg ccctgaacca gctaaggagt tatggctatt aatgtatgac   1080
agaatgacga actatcataa cttaaataat ttaatatggg tatggaactc cattgaagaa   1140
gattggtacc ccggagatga gtatgtggat atagtaagct tcgattccta cccaggtgac   1200
tataactaca gtccaatgag tggtcagtat gaggcgttaa agagttatc aagtaacaaa   1260 aaaataattg caatagcaga aaatggtcca ataccagatc ctgatttact acaacgttat   1320
catgctcatt atagctggtt tactacgtgg aatggcgaca tattaaggga gcaaaatagt   1380
gaagagcatc tgaagaacgt ctataatcac gattatgtaa ttaccttaga tgaacttcca   1440
gattttgaaa catataagga agacgtaccg ttagag                              1476
```

<210> SEQ ID NO 4
<211> LENGTH: 492
<212> TYPE: PRT
<213> ORGANISM: Artificial Sequence
<220> FEATURE:
<223> OTHER INFORMATION: synthetic Bag Man1 precursor

<400> SEQUENCE: 4

```
Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Met Thr Asn Tyr Glu Ser Glu Val Arg Arg Phe Glu Ala Glu Asp Ala
        35                  40                  45

Thr Leu Asn Gly Val Thr Val Lys Asn Ser Glu Pro Gly Phe Ser Gly
    50                  55                  60

Thr Gly Tyr Val Gly Asp Phe Glu Asp Ser Ser Gln Ser Val Thr Phe
65                  70                  75                  80

His Val Asp Val Pro Glu Thr Asp Leu Tyr Thr Leu Thr Ile Gly Tyr
                85                  90                  95

Gly Ala Ile Tyr Gly Ser Glu Lys Val Ala Asn Val Leu Val Asn Gly
            100                 105                 110

Glu Lys Leu Ser Ser Phe Thr Met Gly Ser Gly Phe Gly Lys Ala Ser
        115                 120                 125

Ala Gly Asn Ile Val Leu Asn Ser Gly Ser Asn Thr Ile Ser Ile Thr
    130                 135                 140

Pro Asp Trp Thr His Phe Ala Ile Asp Tyr Ile Glu Val Lys Leu Thr
145                 150                 155                 160

Pro Glu Pro Ile Lys His Asn Val Glu Lys Leu Ile Asn Pro Asn
                165                 170                 175

Ala Thr Asp Glu Ala Lys Val Leu Met Ser Tyr Leu Val Asp Asn Phe
            180                 185                 190

Gly Glu Lys Ile Leu Ser Gly Gln His Asp Phe Pro Asn Thr Arg Pro
        195                 200                 205

Asp Asp Leu Glu Tyr Ile Tyr Glu Ile Thr Gly Lys Tyr Pro Ala Ile
    210                 215                 220

Leu Gly Leu Asp Phe Ile Asp Asn Ser Pro Ser Arg Val Glu Tyr Gly
225                 230                 235                 240

Ala Phe Ala Asp Glu Thr Pro Val Ala Ile Asn Trp Trp Asn Lys Gly
                245                 250                 255

Gly Ile Val Thr Phe Thr Trp His Trp Asn Ala Pro Lys Asp Leu Leu
            260                 265                 270

Asp Glu Pro Gly Asn Glu Trp Trp Arg Gly Phe Tyr Thr Glu Ala Thr
        275                 280                 285

Thr Phe Asp Val Glu Tyr Ala Leu Asn His Pro Asp Ser Glu Asp Tyr
    290                 295                 300

Lys Leu Leu Ile Arg Asp Ile Asp Val Ile Ala Asp Glu Leu Lys Lys
305                 310                 315                 320

Leu Gln Lys Ala Asp Val Pro Val Leu Trp Arg Pro Leu His Glu Ala
                325                 330                 335

Glu Gly Lys Trp Phe Trp Trp Gly Lys Lys Gly Pro Glu Pro Ala Lys
            340                 345                 350

Glu Leu Trp Leu Leu Met Tyr Asp Arg Met Thr Asn Tyr His Asn Leu
        355                 360                 365
```

```
Asn Asn Leu Ile Trp Val Trp Asn Ser Ile Glu Glu Asp Trp Tyr Pro
    370                 375                 380

Gly Asp Glu Tyr Val Asp Ile Val Ser Phe Asp Ser Tyr Pro Gly Asp
385                 390                 395                 400

Tyr Asn Tyr Ser Pro Met Ser Gly Gln Tyr Glu Ala Leu Lys Glu Leu
                405                 410                 415

Ser Ser Asn Lys Lys Ile Ile Ala Ile Ala Glu Asn Gly Pro Ile Pro
            420                 425                 430

Asp Pro Asp Leu Leu Gln Arg Tyr His Ala His Tyr Ser Trp Phe Thr
        435                 440                 445

Thr Trp Asn Gly Asp Ile Leu Arg Glu Gln Asn Ser Glu Glu His Leu
    450                 455                 460

Lys Asn Val Tyr Asn His Asp Tyr Val Ile Thr Leu Asp Glu Leu Pro
465                 470                 475                 480

Asp Phe Glu Thr Tyr Lys Glu Asp Val Pro Leu Glu
                485                 490

<210> SEQ ID NO 5
<211> LENGTH: 463
<212> TYPE: PRT
<213> ORGANISM: Bacillus agaradhaerens

<400> SEQUENCE: 5

Ala Gly Lys Met Thr Asn Tyr Glu Ser Glu Val Arg Arg Phe Glu Ala
1               5                   10                  15

Glu Asp Ala Thr Leu Asn Gly Val Thr Val Lys Asn Ser Glu Pro Gly
            20                  25                  30

Phe Ser Gly Thr Gly Tyr Val Gly Asp Phe Glu Asp Ser Ser Gln Ser
        35                  40                  45

Val Thr Phe His Val Asp Val Pro Glu Thr Asp Leu Tyr Thr Leu Thr
    50                  55                  60

Ile Gly Tyr Gly Ala Ile Tyr Gly Ser Glu Lys Val Ala Asn Val Leu
65                  70                  75                  80

Val Asn Gly Glu Lys Leu Ser Ser Phe Thr Met Gly Ser Gly Phe Gly
                85                  90                  95

Lys Ala Ser Ala Gly Asn Ile Val Leu Asn Ser Gly Ser Asn Thr Ile
            100                 105                 110

Ser Ile Thr Pro Asp Trp Thr His Phe Ala Ile Asp Tyr Ile Glu Val
        115                 120                 125

Lys Leu Thr Pro Glu Pro Ile Lys His Asn Val Glu Lys Lys Leu Ile
    130                 135                 140

Asn Pro Asn Ala Thr Asp Glu Ala Lys Val Leu Met Ser Tyr Leu Val
145                 150                 155                 160

Asp Asn Phe Gly Glu Lys Ile Leu Ser Gly Gln His Asp Phe Pro Asn
                165                 170                 175

Thr Arg Pro Asp Asp Leu Glu Tyr Ile Tyr Glu Ile Thr Gly Lys Tyr
            180                 185                 190

Pro Ala Ile Leu Gly Leu Asp Phe Ile Asp Asn Ser Pro Ser Arg Val
        195                 200                 205

Glu Tyr Gly Ala Phe Ala Asp Glu Thr Pro Val Ala Ile Asn Trp Trp
    210                 215                 220

Asn Lys Gly Gly Ile Val Thr Phe Thr Trp His Trp Asn Ala Pro Lys
225                 230                 235                 240

Asp Leu Leu Asp Glu Pro Gly Asn Glu Trp Trp Arg Gly Phe Tyr Thr
                245                 250                 255
```

```
Glu Ala Thr Thr Phe Asp Val Glu Tyr Ala Leu Asn His Pro Asp Ser
            260                 265                 270

Glu Asp Tyr Lys Leu Leu Ile Arg Asp Ile Asp Val Ile Ala Asp Glu
            275                 280                 285

Leu Lys Lys Leu Gln Lys Ala Asp Val Pro Val Leu Trp Arg Pro Leu
            290                 295                 300

His Glu Ala Glu Gly Lys Trp Phe Trp Trp Gly Lys Lys Gly Pro Glu
305                 310                 315                 320

Pro Ala Lys Glu Leu Trp Leu Leu Met Tyr Asp Arg Met Thr Asn Tyr
            325                 330                 335

His Asn Leu Asn Asn Leu Ile Trp Val Trp Asn Ser Ile Glu Glu Asp
            340                 345                 350

Trp Tyr Pro Gly Asp Glu Tyr Val Asp Ile Val Ser Phe Asp Ser Tyr
            355                 360                 365

Pro Gly Asp Tyr Asn Tyr Ser Pro Met Ser Gly Gln Tyr Glu Ala Leu
            370                 375                 380

Lys Glu Leu Ser Ser Asn Lys Lys Ile Ile Ala Ile Ala Glu Asn Gly
385                 390                 395                 400

Pro Ile Pro Asp Pro Asp Leu Leu Gln Arg Tyr His Ala His Tyr Ser
            405                 410                 415

Trp Phe Thr Thr Trp Asn Gly Asp Ile Leu Arg Glu Gln Asn Ser Glu
            420                 425                 430

Glu His Leu Lys Asn Val Tyr Asn His Asp Tyr Val Ile Thr Leu Asp
            435                 440                 445

Glu Leu Pro Asp Phe Glu Thr Tyr Lys Glu Asp Val Pro Leu Glu
            450                 455                 460

<210> SEQ ID NO 6
<211> LENGTH: 460
<212> TYPE: PRT
<213> ORGANISM: Bacillus agaradhaerens

<400> SEQUENCE: 6

Met Thr Asn Tyr Glu Ser Glu Val Arg Arg Phe Glu Ala Glu Asp Ala
1               5                   10                  15

Thr Leu Asn Gly Val Thr Val Lys Asn Ser Glu Pro Gly Phe Ser Gly
            20                  25                  30

Thr Gly Tyr Val Gly Asp Phe Glu Asp Ser Ser Gln Ser Val Thr Phe
            35                  40                  45

His Val Asp Val Pro Glu Thr Asp Leu Tyr Thr Leu Thr Ile Gly Tyr
            50                  55                  60

Gly Ala Ile Tyr Gly Ser Glu Lys Val Ala Asn Val Leu Val Asn Gly
65                  70                  75                  80

Glu Lys Leu Ser Ser Phe Thr Met Gly Ser Gly Phe Gly Lys Ala Ser
            85                  90                  95

Ala Gly Asn Ile Val Leu Asn Ser Gly Ser Asn Thr Ile Ser Ile Thr
            100                 105                 110

Pro Asp Trp Thr His Phe Ala Ile Asp Tyr Ile Glu Val Lys Leu Thr
            115                 120                 125

Pro Glu Pro Ile Lys His Asn Val Glu Lys Lys Leu Ile Asn Pro Asn
            130                 135                 140

Ala Thr Asp Glu Ala Lys Val Leu Met Ser Tyr Leu Val Asp Asn Phe
145                 150                 155                 160

Gly Glu Lys Ile Leu Ser Gly Gln His Asp Phe Pro Asn Thr Arg Pro
```

```
                165                 170                 175
Asp Asp Leu Glu Tyr Ile Tyr Glu Ile Thr Gly Lys Tyr Pro Ala Ile
            180                 185                 190

Leu Gly Leu Asp Phe Ile Asp Asn Ser Pro Ser Arg Val Glu Tyr Gly
        195                 200                 205

Ala Phe Ala Asp Glu Thr Pro Val Ala Ile Asn Trp Asn Lys Gly
    210                 215                 220

Gly Ile Val Thr Phe Thr Trp His Trp Asn Ala Pro Lys Asp Leu Leu
225                 230                 235                 240

Asp Glu Pro Gly Asn Glu Trp Trp Arg Gly Phe Tyr Thr Glu Ala Thr
            245                 250                 255

Thr Phe Asp Val Glu Tyr Ala Leu Asn His Pro Asp Ser Glu Asp Tyr
        260                 265                 270

Lys Leu Leu Ile Arg Asp Ile Asp Val Ile Ala Asp Glu Leu Lys Lys
    275                 280                 285

Leu Gln Lys Ala Asp Val Pro Val Leu Trp Arg Pro Leu His Glu Ala
    290                 295                 300

Glu Gly Lys Trp Phe Trp Trp Gly Lys Lys Gly Pro Glu Pro Ala Lys
305                 310                 315                 320

Glu Leu Trp Leu Leu Met Tyr Asp Arg Met Thr Asn Tyr His Asn Leu
            325                 330                 335

Asn Asn Leu Ile Trp Val Trp Asn Ser Ile Glu Glu Asp Trp Tyr Pro
        340                 345                 350

Gly Asp Glu Tyr Val Asp Ile Val Ser Phe Asp Ser Tyr Pro Gly Asp
    355                 360                 365

Tyr Asn Tyr Ser Pro Met Ser Gly Gln Tyr Glu Ala Leu Lys Glu Leu
    370                 375                 380

Ser Ser Asn Lys Lys Ile Ile Ala Ile Ala Glu Asn Gly Pro Ile Pro
385                 390                 395                 400

Asp Pro Asp Leu Leu Gln Arg Tyr His Ala His Tyr Ser Trp Phe Thr
            405                 410                 415

Thr Trp Asn Gly Asp Ile Leu Arg Glu Gln Asn Ser Glu Glu His Leu
        420                 425                 430

Lys Asn Val Tyr Asn His Asp Tyr Val Ile Thr Leu Asp Glu Leu Pro
    435                 440                 445

Asp Phe Glu Thr Tyr Lys Glu Asp Val Pro Leu Glu
    450                 455                 460

<210> SEQ ID NO 7
<211> LENGTH: 458
<212> TYPE: PRT
<213> ORGANISM: Bacillus agaradhaerens

<400> SEQUENCE: 7

Asn Tyr Glu Ser Glu Val Arg Arg Phe Glu Ala Glu Asp Ala Thr Leu
1               5                   10                  15

Asn Gly Val Thr Val Lys Asn Ser Glu Pro Gly Phe Ser Gly Thr Gly
            20                  25                  30

Tyr Val Gly Asp Phe Glu Asp Ser Ser Gln Ser Val Thr Phe His Val
        35                  40                  45

Asp Val Pro Glu Thr Asp Leu Tyr Thr Leu Thr Ile Gly Tyr Gly Ala
    50                  55                  60

Ile Tyr Gly Ser Glu Lys Val Ala Asn Val Leu Val Asn Gly Glu Lys
65                  70                  75                  80
```

```
Leu Ser Ser Phe Thr Met Gly Ser Gly Phe Gly Lys Ala Ser Ala Gly
                    85                  90                  95
Asn Ile Val Leu Asn Ser Gly Ser Asn Thr Ile Ser Ile Thr Pro Asp
            100                 105                 110
Trp Thr His Phe Ala Ile Asp Tyr Ile Glu Val Lys Leu Thr Pro Glu
            115                 120                 125
Pro Ile Lys His Asn Val Glu Lys Lys Leu Ile Asn Pro Asn Ala Thr
        130                 135                 140
Asp Glu Ala Lys Val Leu Met Ser Tyr Leu Val Asp Asn Phe Gly Glu
145                 150                 155                 160
Lys Ile Leu Ser Gly Gln His Asp Phe Pro Asn Thr Arg Pro Asp Asp
                165                 170                 175
Leu Glu Tyr Ile Tyr Glu Ile Thr Gly Lys Tyr Pro Ala Ile Leu Gly
            180                 185                 190
Leu Asp Phe Ile Asp Asn Ser Pro Ser Arg Val Glu Tyr Gly Ala Phe
            195                 200                 205
Ala Asp Glu Thr Pro Val Ala Ile Asn Trp Trp Asn Lys Gly Gly Ile
        210                 215                 220
Val Thr Phe Thr Trp His Trp Asn Ala Pro Lys Asp Leu Leu Asp Glu
225                 230                 235                 240
Pro Gly Asn Glu Trp Trp Arg Gly Phe Tyr Thr Glu Ala Thr Thr Phe
                245                 250                 255
Asp Val Glu Tyr Ala Leu Asn His Pro Asp Ser Glu Asp Tyr Lys Leu
            260                 265                 270
Leu Ile Arg Asp Ile Asp Val Ile Ala Asp Glu Leu Lys Lys Leu Gln
            275                 280                 285
Lys Ala Asp Val Pro Val Leu Trp Arg Pro Leu His Glu Ala Glu Gly
        290                 295                 300
Lys Trp Phe Trp Trp Gly Lys Lys Gly Pro Glu Pro Ala Lys Glu Leu
305                 310                 315                 320
Trp Leu Leu Met Tyr Asp Arg Met Thr Asn Tyr His Asn Leu Asn Asn
                325                 330                 335
Leu Ile Trp Val Trp Asn Ser Ile Glu Glu Asp Trp Tyr Pro Gly Asp
            340                 345                 350
Glu Tyr Val Asp Ile Val Ser Phe Asp Ser Tyr Pro Gly Asp Tyr Asn
            355                 360                 365
Tyr Ser Pro Met Ser Gly Gln Tyr Glu Ala Leu Lys Glu Leu Ser Ser
        370                 375                 380
Asn Lys Lys Ile Ile Ala Ile Ala Glu Asn Gly Pro Ile Pro Asp Pro
385                 390                 395                 400
Asp Leu Leu Gln Arg Tyr His Ala His Tyr Ser Trp Phe Thr Thr Trp
                405                 410                 415
Asn Gly Asp Ile Leu Arg Glu Gln Asn Ser Glu Glu His Leu Lys Asn
            420                 425                 430
Val Tyr Asn His Asp Tyr Val Ile Thr Leu Asp Glu Leu Pro Asp Phe
            435                 440                 445
Glu Thr Tyr Lys Glu Asp Val Pro Leu Glu
    450                 455

<210> SEQ ID NO 8
<211> LENGTH: 46
<212> TYPE: DNA
<213> ORGANISM: Artificial Sequence
<220> FEATURE:
<223> OTHER INFORMATION: synthetic primer
```

<400> SEQUENCE: 8
tgagcgcgca ggctgctgga aaaatgacaa actatgaatc agaggt   46

<210> SEQ ID NO 9
<211> LENGTH: 35
<212> TYPE: DNA
<213> ORGANISM: Artificial Sequence
<220> FEATURE:
<223> OTHER INFORMATION: synthetic primer

<400> SEQUENCE: 9
tgtggatcct tactctaacg gtacgtcttc cttat   35

<210> SEQ ID NO 10
<211> LENGTH: 306
<212> TYPE: PRT
<213> ORGANISM: Bacillus agaradhaerens

<400> SEQUENCE: 10

```
Ile Asn Pro Asn Ala Thr Asp Glu Ala Lys Val Leu Met Ser Tyr Leu
 1               5                  10                  15

Val Asp Asn Phe Gly Glu Lys Ile Leu Ser Gly Gln His Asp Phe Pro
            20                  25                  30

Asn Thr Arg Pro Asp Asp Leu Glu Tyr Ile Tyr Glu Ile Thr Gly Lys
        35                  40                  45

Tyr Pro Ala Ile Leu Gly Leu Asp Phe Ile Asp Asn Ser Pro Ser Arg
    50                  55                  60

Val Glu Tyr Gly Ala Phe Ala Asp Glu Thr Pro Val Ala Ile Asn Trp
65                  70                  75                  80

Trp Asn Lys Gly Gly Ile Val Thr Phe Thr Trp His Trp Asn Ala Pro
                85                  90                  95

Lys Asp Leu Leu Asp Glu Pro Gly Asn Glu Trp Trp Arg Gly Phe Tyr
            100                 105                 110

Thr Glu Ala Thr Thr Phe Asp Val Glu Tyr Ala Leu Asn His Pro Asp
        115                 120                 125

Ser Glu Asp Tyr Lys Leu Leu Ile Arg Asp Ile Asp Val Ile Ala Asp
    130                 135                 140

Glu Leu Lys Lys Leu Gln Lys Ala Asp Val Pro Val Leu Trp Arg Pro
145                 150                 155                 160

Leu His Glu Ala Glu Gly Lys Trp Phe Trp Trp Gly Lys Lys Gly Pro
                165                 170                 175

Glu Pro Ala Lys Glu Leu Trp Leu Leu Met Tyr Asp Arg Met Thr Asn
            180                 185                 190

Tyr His Asn Leu Asn Asn Leu Ile Trp Val Trp Asn Ser Ile Glu Glu
        195                 200                 205

Asp Trp Tyr Pro Gly Asp Glu Tyr Val Asp Ile Val Ser Phe Asp Ser
    210                 215                 220

Tyr Pro Gly Asp Tyr Asn Tyr Ser Pro Met Ser Gly Gln Tyr Glu Ala
225                 230                 235                 240

Leu Lys Glu Leu Ser Ser Asn Lys Lys Ile Ile Ala Ile Ala Glu Asn
                245                 250                 255

Gly Pro Ile Pro Asp Pro Asp Leu Leu Gln Arg Tyr His Ala His Tyr
            260                 265                 270

Ser Trp Phe Thr Thr Trp Asn Gly Asp Ile Leu Arg Glu Gln Asn Ser
        275                 280                 285
```

```
Glu Glu His Leu Lys Asn Val Tyr Asn His Asp Tyr Val Ile Thr Leu
            290                 295                 300

Asp Glu
305

<210> SEQ ID NO 11
<211> LENGTH: 452
<212> TYPE: PRT
<213> ORGANISM: Bacillus sp.

<400> SEQUENCE: 11

Ile Phe Glu Ala Glu Asp Ala Ile Leu Asn Gly Leu Thr Ile Lys Asn
1               5                   10                  15

Ser Glu Pro Gly Phe Ser Gly Thr Gly Tyr Val Gly Asp Phe Glu Asn
            20                  25                  30

Ser Ser Gln Ser Val Thr Phe Gln Ile Glu Ala Pro Lys Ala Gly Leu
        35                  40                  45

Tyr Asn Leu Asn Ile Gly Tyr Gly Ala Ile Tyr Gly Ser Gly Lys Val
    50                  55                  60

Ala Asn Val Ile Val Asn Gly Glu Lys Leu Ser Thr Phe Thr Met Gly
65                  70                  75                  80

Ser Gly Phe Gly Lys Ala Ser Ala Gly Lys Val Leu Leu Asn Ser Gly
                85                  90                  95

Leu Asn Thr Ile Ser Ile Thr Pro Asn Trp Thr Trp Phe Thr Ile Asp
            100                 105                 110

Tyr Ile Glu Val Ile His Ala Pro Glu Pro Glu Asn His Asn Val Glu
        115                 120                 125

Lys Thr Leu Ile Asn Pro Asn Ala Thr Asp Glu Ala Lys Ala Leu Ile
    130                 135                 140

Ser Tyr Leu Val Asp Asn Phe Gly Glu Lys Ile Leu Ala Gly Gln His
145                 150                 155                 160

Asp Tyr Pro Asn Thr Arg Pro Arg Asp Leu Glu Tyr Ile Tyr Glu Thr
                165                 170                 175

Thr Gly Lys Tyr Pro Ala Val Leu Gly Leu Asp Phe Ile Asp Asn Ser
            180                 185                 190

Pro Ser Arg Val Glu Arg Gly Ala Ser Ala Asp Glu Thr Pro Val Ala
        195                 200                 205

Ile Asp Trp Trp Asn Lys Gly Ile Val Thr Phe Thr Trp His Trp
    210                 215                 220

Asn Ala Pro Lys Asp Leu Leu Asp Glu Pro Gly Asn Glu Trp Trp Ser
225                 230                 235                 240

Gly Phe Tyr Thr Arg Ala Thr Thr Phe Asp Val Glu Tyr Ala Leu Lys
                245                 250                 255

His Pro Lys Ser Glu Asp Tyr Met Leu Leu Ile Arg Asp Ile Asp Val
            260                 265                 270

Ile Ala Gly Glu Leu Lys Lys Leu Gln Glu Ala Asn Val Pro Val Leu
        275                 280                 285

Trp Arg Pro Leu His Glu Ala Glu Gly Gly Trp Phe Trp Trp Gly Ala
    290                 295                 300

Lys Gly Pro Glu Ser Thr Lys Gly Leu Trp Arg Leu Met Tyr Asp Arg
305                 310                 315                 320

Met Thr Asn Tyr His Asn Leu Asn Asn Leu Ile Trp Val Trp Asn Ser
                325                 330                 335

Ile Glu Glu Asp Trp Tyr Pro Gly Asp Glu Tyr Val Asp Ile Val Ser
            340                 345                 350
```

```
Phe Asp Ser Tyr Pro Gly Glu Tyr Asn Tyr Ser Pro Met Ser Arg Glu
            355                 360                 365

Tyr Glu Ala Leu Lys Glu Leu Ser Ser Asn Lys Lys Leu Ile Ala Ile
    370                 375                 380

Ala Glu Asn Gly Pro Ile Pro Asp Pro Asp Leu Leu Gln Leu Tyr His
385                 390                 395                 400

Ala Asn Tyr Ser Trp Phe Ala Thr Trp Asn Gly Asp Ile Leu Arg Asn
                405                 410                 415

Gln Asn Ser Glu Glu His Leu Arg Lys Val Tyr Asn His Asp Tyr Val
            420                 425                 430

Ile Thr Leu Asn Lys Leu Pro Asn Leu Lys Thr Tyr Arg Gly Arg Cys
            435                 440                 445

Thr Tyr Thr Asp
    450

<210> SEQ ID NO 12
<211> LENGTH: 491
<212> TYPE: PRT
<213> ORGANISM: Paenibacillus polymyxa

<400> SEQUENCE: 12

Val Pro Gln Thr Pro Val Asp Gly Gln Asp Arg Tyr Glu Ala Glu Asp
1               5                   10                  15

Gly Thr Leu Lys Gly Thr Thr Val Glu Ser Ser Gly Thr Gly Phe Ser
            20                  25                  30

Gly Thr Gly Tyr Val Thr Asn Phe His Asn Ala Gly Asp Ser Leu Thr
        35                  40                  45

Met Thr Ile Gln Ala Glu Ala Ala Gly Leu Tyr Asn Leu Thr Ile Gly
    50                  55                  60

Tyr Arg Ser Pro Tyr Asp Asp Lys Arg Thr Asn Phe Ser Leu Asn Gly
65                  70                  75                  80

Lys Ala Ser Gly Glu Leu Ile Leu Ser Lys Ser Ala Asp Phe Lys Glu
                85                  90                  95

Thr Ser Gly Gly Lys Val Leu Leu Asn Ala Gly Ala Asn Thr Ile Gly
            100                 105                 110

Phe Glu Thr Gly Trp Gly Trp Tyr Asp Ile Asp Tyr Val Lys Leu Lys
        115                 120                 125

Pro Ala Ala Asp Arg Pro Pro His Ala Val Thr Lys Thr Leu Thr Asn
130                 135                 140

Pro Asn Ala Thr Val Glu Ala Arg Ala Leu Met Asn Tyr Leu Val Asp
145                 150                 155                 160

Gln Tyr Gly Lys Asn Met Leu Ser Gly Gln Glu Glu Ile Thr Glu Ile
                165                 170                 175

Asp Trp Leu Gln Ala Asn Val Gly Lys Lys Pro Ala Ile Ala Ala Leu
            180                 185                 190

Asp Leu Ile Asp Tyr Ser Pro Ser Arg Ala Glu His Gly Leu Ser Ser
        195                 200                 205

Thr Glu Thr Glu Lys Ala Ile Ala Trp Asp Lys Gln Gly Gly Ile Val
    210                 215                 220

Thr Phe Ala Trp His Trp Asn Ala Pro Lys Gly Leu Ile Asp Thr Gln
225                 230                 235                 240

Gly Lys Glu Trp Trp Arg Gly Phe Tyr Ala Asp Ser Thr Thr Phe Asp
                245                 250                 255

Ile Glu Tyr Ala Met Asn His Pro Glu Ser Glu Asp Tyr Lys Leu Leu
```

Ile Arg Asp Ile Asp Val Ile Ala Gly Gln Leu Lys Lys Leu Gln Asp
260              265                 270

Ala Lys Val Pro Val Leu Phe Arg Pro Leu His Glu Ala Glu Gly Lys
275              280                 285

Trp Phe Trp Trp Gly Ala Lys Gly Pro Glu Pro Val Lys Lys Leu Tyr
290              295                 300

Ile Leu Met His Asp Arg Leu Thr Asn Val His Lys Leu Asn Asn Leu
305              310                 315                 320

Ile Trp Val Trp Asn Ser Val Ala Pro Asp Trp Tyr Pro Gly Asp Glu
325              330                 335

Tyr Val Asp Ile Leu Ser Phe Asp Ser Tyr Pro Gln Ala Gly Asp Tyr
340              345                 350

Ser Pro Gln Ile Ala Lys Tyr Glu Asp Leu Val Thr Leu Gly Lys Asp
355              360                 365

Lys Lys Leu Val Ala Met Ser Glu Asn Gly Pro Ile Pro Asp Pro Asp
370              375                 380

Leu Met Lys Ala Tyr Gln Ala His Trp Ser Trp Phe Ala Thr Trp Tyr
385              390                 395                 400

Gly Asp Phe Leu Arg Asp Gly Lys Gln Asn Ser Leu Glu His Leu Lys
405              410                 415

Lys Val Tyr Asn His Pro Asn Val Ile Thr Leu Glu Lys Leu Pro Thr
420              425                 430

Asn Leu Lys Thr Tyr Gly Ile Thr Glu Gln Pro Ser Val Pro Gly Ser
435              440                 445

Phe Thr Leu Asn Ala Ala Gly Glu Thr Ala Lys Val Lys Leu Ser Trp
450              455                 460

Thr Ala Ser Ala Asn Ala Ala Ser Tyr Glu Val
465              470                 475                 480

485              490

<210> SEQ ID NO 13
<211> LENGTH: 491
<212> TYPE: PRT
<213> ORGANISM: Paenibacillus polymyxa

<400> SEQUENCE: 13

Val Pro Lys Val Ser Val Asn Asp Pro Val Arg Tyr Glu Ala Glu Asp
1                5                  10                  15

Gly Thr Leu Lys Gly Thr Ile Val Glu Ser Ser Gly Thr Gly Tyr Ser
                20                 25                  30

Gly Thr Gly Tyr Val Thr Asn Phe His Asn Ala Gly Asp Ser Leu Thr
            35                 40                  45

Met Thr Ile Gln Ala Pro Thr Ala Gly Leu Tyr Asn Leu Thr Ile Gly
    50                 55                  60

Tyr Arg Ser Pro His Asp Asp Lys Arg Thr Asn Phe Ser Leu Asn Gly
65                 70                  75                  80

Lys Ala Phe Gly Glu Leu Val Leu Gly Lys Thr Ala Asp Phe Lys Glu
                85                 90                  95

Thr Ser Gly Gly Lys Leu Leu Leu Asn Ala Gly Ala Asn Thr Ile Gly
            100                105                 110

Phe Glu Thr Gly Trp Gly Trp Tyr Asp Ile Asp Tyr Val Arg Leu Glu
        115                120                 125

Pro Ala Ala Asp Arg Pro Pro His Ala Val Thr Lys Thr Leu Thr Asn
    130                135                 140

```
Pro Asn Ala Thr Val Glu Lys Ala Leu Met Asn Tyr Leu Val Asp
145                 150                 155                 160

Gln Tyr Gly Lys Asn Met Leu Ser Gly Gln Glu Glu Ile Asn Glu Ile
            165                 170                 175

Asp Trp Leu Gln Ala Asn Val Gly Lys Lys Pro Ala Ile Ala Ala Leu
        180                 185                 190

Asp Leu Ile Asp Tyr Ser Pro Ser Arg Ala Glu His Gly Leu Ser Ser
    195                 200                 205

Thr Glu Ala Glu Lys Ala Ile Ala Trp Asp Lys Gln Gly Gly Ile Val
210                 215                 220

Thr Phe Ala Trp His Trp Asn Ala Pro Lys Gly Leu Ile Asp Thr Gln
225                 230                 235                 240

Gly Lys Glu Trp Trp Arg Gly Phe Tyr Ala Asp Ser Thr Thr Phe Asp
            245                 250                 255

Ile Glu Tyr Ala Met Ser His Pro Glu Ser Glu Asp Tyr Lys Leu Leu
        260                 265                 270

Ile Arg Asp Ile Asp Val Ile Ala Ala Gln Leu Lys Lys Leu Gln Asp
    275                 280                 285

Ala Lys Val Pro Val Leu Phe Arg Pro Leu His Glu Ala Glu Gly Lys
290                 295                 300

Trp Phe Trp Trp Gly Ala Lys Gly Pro Glu Pro Val Lys Lys Leu Tyr
305                 310                 315                 320

Ile Leu Met His Asp Arg Leu Thr Asn Val His Lys Leu Asn Asn Leu
            325                 330                 335

Ile Trp Val Trp Asn Ser Val Ala Pro Asp Trp Tyr Pro Gly Asp Glu
        340                 345                 350

Tyr Val Asp Ile Leu Ser Phe Asp Ser Tyr Pro Gln Ala Gly Asp Tyr
    355                 360                 365

Ser Pro Gln Ile Ala Lys Tyr Glu Asp Leu Val Thr Leu Gly Lys Asp
370                 375                 380

Lys Lys Leu Val Ala Met Ser Glu Asn Gly Pro Ile Pro Asp Pro Asp
385                 390                 395                 400

Leu Met Lys Ala Tyr Gln Ala His Trp Ser Trp Phe Ala Thr Trp Tyr
            405                 410                 415

Gly Asp Phe Leu Arg Asp Gly Lys Gln Asn Ser Leu Glu His Leu Lys
        420                 425                 430

Lys Val Tyr Asn His Pro Asn Val Ile Thr Leu Asp Glu Leu Pro Thr
    435                 440                 445

Asn Leu Lys Thr Tyr Gly Ile Thr Glu Gln Pro Ser Val Pro Gly Ser
450                 455                 460

Phe Thr Leu Asn Ala Ala Gly Glu Thr Ala Lys Val Ser Leu Ser Trp
465                 470                 475                 480

Thr Ala Ser Ala Asn Ala Lys Ser Tyr Glu Val
                485                 490

<210> SEQ ID NO 14
<211> LENGTH: 491
<212> TYPE: PRT
<213> ORGANISM: Paenibacillus polymyxa

<400> SEQUENCE: 14

Val Pro Lys Thr Pro Val Asn Gly Pro Ala Arg Tyr Glu Ala Glu Glu
1               5                   10                  15

Gly Ala Leu Lys Gly Thr Ile Val Glu Ser Ser Gly Thr Gly Tyr Ser
            20                  25                  30
```

-continued

Gly Thr Gly Tyr Val Thr Asn Phe His Asn Pro Gly Asp Ser Leu Thr
             35                  40                  45

Met Thr Ile Gln Ala Pro Thr Ala Gly Leu Tyr Asn Leu Thr Ile Gly
 50                  55                  60

Tyr Arg Ser Pro His Asp Asp Lys Arg Thr Asn Phe Ser Leu Asn Gly
 65                  70                  75                  80

Lys Ala Phe Gly Glu Leu Leu Leu Lys Lys Thr Thr Asp Phe Lys Glu
                 85                  90                  95

Thr Ser Gly Gly Lys Val Leu Leu Asn Ala Gly Ala Asn Thr Ile Gly
            100                 105                 110

Phe Glu Thr Gly Trp Gly Trp Tyr Asp Ile Asp Tyr Val Arg Leu Glu
            115                 120                 125

Pro Ala Ala Asp Arg Pro Pro His Ala Val Thr Lys Thr Leu Thr Asn
130                 135                 140

Pro Asn Ala Thr Val Glu Ala Lys Ala Leu Met Asn Tyr Leu Val Asp
145                 150                 155                 160

Gln Tyr Gly Lys Asn Met Leu Ser Gly Gln Glu Ile Asn Glu Ile
                165                 170                 175

Asp Trp Leu Gln Ala Asn Val Gly Lys Lys Pro Ala Ile Ala Ala Leu
            180                 185                 190

Asp Leu Ile Asp Tyr Ser Pro Ser Arg Ala Glu His Gly Leu Ser Ser
            195                 200                 205

Thr Glu Ala Glu Lys Ala Ile Ala Trp Asp Lys Gln Gly Gly Ile Val
            210                 215                 220

Thr Phe Ala Trp His Trp Asn Ala Pro Lys Gly Leu Ile Asp Thr Gln
225                 230                 235                 240

Gly Lys Glu Trp Trp Arg Gly Phe Tyr Ala Asp Ser Thr Thr Phe Asp
                245                 250                 255

Ile Glu Tyr Ala Met Asn His Pro Glu Ser Glu Asp Tyr Lys Leu Leu
            260                 265                 270

Ile Arg Asp Ile Asp Val Ile Ala Gly Gln Leu Lys Lys Leu Gln Asp
            275                 280                 285

Ala Lys Val Pro Val Leu Phe Arg Pro Leu His Glu Ala Glu Gly Lys
290                 295                 300

Trp Phe Trp Trp Gly Ala Lys Gly Pro Glu Pro Val Lys Lys Leu Tyr
305                 310                 315                 320

Ile Leu Met His Asp Arg Leu Thr Asn Val His Lys Leu Asn Asn Leu
                325                 330                 335

Ile Trp Val Trp Asn Ser Val Ala Pro Asp Trp Tyr Pro Gly Asp Glu
            340                 345                 350

Tyr Val Asp Ile Leu Ser Phe Asp Ser Tyr Pro Gln Ala Gly Asp Tyr
            355                 360                 365

Ser Pro Gln Ile Ala Lys Tyr Glu Asp Leu Val Ala Leu Gly Lys Asp
370                 375                 380

Lys Lys Leu Val Ala Met Ser Glu Asn Gly Pro Ile Pro Asp Pro Asp
385                 390                 395                 400

Leu Met Lys Ala Tyr Gln Ala His Trp Ser Trp Phe Ala Thr Trp Tyr
                405                 410                 415

Gly Asp Phe Val Arg Asp Gly Lys Gln Asn Ser Leu Glu His Leu Lys
            420                 425                 430

Lys Val Tyr Asn His Pro Asn Val Ile Thr Leu Asp Glu Leu Pro Thr
            435                 440                 445

```
Asn Leu Lys Thr Tyr Gly Ile Thr Glu Gln Pro Pro Val Pro Gly Ser
    450                 455                 460

Phe Thr Leu Asn Ala Ala Gly Glu Thr Ala Lys Val Ser Leu Ser Trp
465                 470                 475                 480

Thr Ala Ser Ala Asn Ala Lys Ser Tyr Glu Val
                485                 490

<210> SEQ ID NO 15
<211> LENGTH: 491
<212> TYPE: PRT
<213> ORGANISM: Paenibacillus polymyxa

<400> SEQUENCE: 15

Val Pro Lys Met Pro Val Asn Gly Pro Ala Arg Tyr Glu Ala Glu Glu
1               5                   10                  15

Gly Thr Leu Lys Gly Thr Ile Val Glu Ser Ser Gly Thr Gly Tyr Ser
            20                  25                  30

Gly Ala Gly Tyr Val Thr Asn Phe His Asn Pro Gly Asp Ser Leu Thr
        35                  40                  45

Met Thr Ile Gln Ala Pro Thr Ala Gly Leu Tyr Asn Leu Thr Ile Gly
    50                  55                  60

Tyr Arg Ser Pro His Asp Asp Lys Arg Thr Asn Phe Ser Leu Asn Gly
65                  70                  75                  80

Lys Ala Phe Gly Glu Leu Leu Leu Lys Lys Thr Ala Asp Phe Lys Glu
                85                  90                  95

Thr Ser Gly Gly Lys Val Leu Leu Asn Ala Gly Ala Asn Thr Ile Ser
            100                 105                 110

Phe Glu Thr Gly Trp Gly Trp Tyr Asp Ile Asp Tyr Val Arg Leu Glu
        115                 120                 125

Pro Ala Ala Asp Arg Pro Pro His Ala Val Thr Lys Thr Leu Thr Asn
    130                 135                 140

Pro Asn Ala Thr Val Glu Ala Lys Ala Leu Met Asn Tyr Leu Val Asp
145                 150                 155                 160

Gln Tyr Gly Lys Asn Met Leu Ser Gly Gln Glu Glu Ile Asn Glu Ile
                165                 170                 175

Asp Trp Leu Gln Ala Asn Val Gly Lys Lys Pro Ala Ile Ala Ala Leu
            180                 185                 190

Asp Leu Ile Asp Tyr Ser Pro Ser Arg Ala Glu His Gly Leu Ser Ser
        195                 200                 205

Thr Glu Ala Glu Lys Ala Ile Ala Trp Asp Lys Gln Gly Gly Ile Val
    210                 215                 220

Thr Phe Ala Trp His Trp Asn Ala Pro Lys Gly Leu Ile Asp Thr Gln
225                 230                 235                 240

Gly Lys Glu Trp Trp Arg Gly Phe Tyr Ala Asp Ser Thr Thr Phe Asp
                245                 250                 255

Ile Glu Tyr Ala Met Asn His Pro Glu Ser Glu Asp Tyr Lys Leu Leu
            260                 265                 270

Ile Arg Asp Ile Asp Val Ile Ala Gly Gln Leu Lys Lys Leu Gln Asp
        275                 280                 285

Ala Lys Val Pro Val Leu Phe Arg Pro Leu His Glu Ala Glu Gly Lys
    290                 295                 300

Trp Phe Trp Trp Gly Ala Lys Gly Pro Glu Pro Val Lys Lys Leu Tyr
305                 310                 315                 320

Ile Leu Met His Asp Arg Leu Thr Asn Val His Lys Leu Asn Asn Leu
                325                 330                 335
```

```
Ile Trp Val Trp Asn Ser Val Ala Pro Asp Trp Tyr Pro Gly Asp Glu
            340                 345                 350

Tyr Val Asp Ile Leu Ser Phe Asp Ser Tyr Pro Gln Ala Gly Asp Tyr
            355                 360                 365

Ser Pro Gln Ile Ser Lys Tyr Glu Asp Leu Val Ala Leu Gly Lys Asp
            370                 375                 380

Lys Lys Leu Val Ala Met Ser Glu Asn Gly Pro Ile Pro Asp Pro Asp
385                 390                 395                 400

Leu Met Lys Ala Tyr Gln Ala His Trp Ser Trp Phe Ala Thr Trp Tyr
                405                 410                 415

Gly Asp Phe Val Arg Asp Gly Lys Gln Asn Ser Leu Glu His Leu Lys
            420                 425                 430

Lys Val Tyr Asn His Pro Asn Val Ile Thr Leu Asp Glu Leu Pro Thr
            435                 440                 445

Asn Leu Lys Thr Tyr Gly Ile Thr Glu Gln Pro Ser Val Pro Gly Ser
            450                 455                 460

Phe Thr Leu Asn Ala Ala Gly Glu Thr Ala Lys Val Ser Leu Ser Trp
465                 470                 475                 480

Thr Ala Ser Ala Asn Ala Lys Ser Tyr Glu Val
                485                 490

<210> SEQ ID NO 16
<211> LENGTH: 443
<212> TYPE: PRT
<213> ORGANISM: Paenibacillus sp. BME-14

<400> SEQUENCE: 16

Ile Phe Glu Ala Glu Asp Gly Leu Leu Asn Gly Val Asp Val Met Thr
1               5                   10                  15

Gln Phe Gln Gly Tyr Ser Gly Thr Gly Tyr Val Gly Gly Phe Asp Ala
            20                  25                  30

Gln Asn Asp Lys Leu Ser Val Gln Val Thr Val Pro Thr Gly Leu
            35                  40                  45

Tyr Asn Leu Ser Ile Gly Tyr Gln Ala Pro His Gly Thr Lys Asn Thr
50                  55                  60

Ser Leu Val Val Gly Asp Thr Ala Gln Gly Glu Ile Thr Leu His Glu
65                  70                  75                  80

Thr Thr Asn Phe Ser Glu Val Gly Ala Gly Lys Ile Met Leu Gln Ala
                85                  90                  95

Gly Ser Thr Gln Ile Ser Phe Ser Asn Trp Gly Trp Tyr Tyr Ile
            100                 105                 110

Asp Tyr Val Arg Leu Glu Arg Ala Ile Asp Pro Pro His Gln Ile
            115                 120                 125

Asn Ala Ser Leu Val Asn Pro Asp Ala Ser Ser Val Ala Gln Ser Leu
            130                 135                 140

Tyr Asn Tyr Leu Arg Ser Glu Tyr Gly Gln His Ile Leu Ser Gly Gln
145                 150                 155                 160

Gln Thr Leu Ala Asp Ala Asn Trp Ile His Ser Thr Leu Gly Lys Lys
                165                 170                 175

Pro Ala Val Leu Gly Leu Asp Leu Met Asp Tyr Ser Pro Ser Arg Ile
            180                 185                 190

Glu Arg Gly Thr Val Ser Thr Asp Ile Glu His Ala Ile Glu Trp Asp
            195                 200                 205

Ala Gly Gly Gly Ile Val Thr Phe Ala Trp His Trp Asn Ala Pro Lys
```

```
                210             215             220
Asp Leu Ile Asp Gln Pro Gly Lys Glu Trp Trp Arg Gly Phe Tyr Thr
225                 230                 235                 240

Glu Ala Thr Thr Phe Asp Ile Glu Tyr Ala Met Ser His Pro Glu Ser
                245                 250                 255

Gln Asp Tyr Gln Leu Leu Ile Arg Asp Met Asp Ala Ile Ala Val Gln
            260                 265                 270

Leu Lys Arg Leu Gln Gln Glu Asp Ile Pro Val Leu Trp Arg Pro Leu
        275                 280                 285

His Glu Ala Glu Gly Gly Trp Phe Trp Trp Gly Ala Lys Gly Pro Glu
    290                 295                 300

Pro Ala Lys Glu Leu Tyr Gln Leu Met Tyr Asp Arg Phe Thr Asn Phe
305                 310                 315                 320

His Gly Leu Asp Asn Leu Ile Trp Val Trp Asn Ser Glu Asn Pro Ala
                325                 330                 335

Trp Tyr Pro Gly Asp Pro Tyr Val Asp Ile Ile Ser Val Asp Ser Tyr
                340                 345                 350

Pro Gly Ala Gly Asn Tyr Gly Pro Val Ser Ser Arg Tyr Glu Asn Leu
            355                 360                 365

Lys Thr Leu Val Asn Asp Gln Lys Ile Ile Ala Leu Thr Glu Asn Gly
        370                 375                 380

Pro Ile Pro Asp Pro Asp Leu Leu Gln Ala Tyr His Ala Asp Trp Ser
385                 390                 395                 400

Trp Phe Val Thr Trp Ser Gly Glu Phe Ile Arg Asp Gly Val Gln Asn
                405                 410                 415

Ser Thr Gln His Leu Thr Lys Val Tyr Asn Ser Pro Tyr Val Ile Thr
                420                 425                 430

Leu Asp Glu Leu Pro Asp Trp Lys Asn Glu Tyr
                435                 440

<210> SEQ ID NO 17
<211> LENGTH: 338
<212> TYPE: PRT
<213> ORGANISM: Paenibacillus sp. Y412MC10

<400> SEQUENCE: 17

Met Thr Lys Ala Ser Ser Thr Arg Phe Glu Val Gln Pro Asn Leu Ile
1               5                   10                  15

Asn Pro Ala Ala Ser Asp Gln Ala Lys Arg Leu Met Gly Tyr Leu Cys
                20                  25                  30

Ser Ile Tyr Gly Lys Arg Met Leu Thr Gly Gln Gln Ile Gly Val Val
            35                  40                  45

Ser Thr Pro Glu Phe Asp Met Ile His Glu Val Thr Gly Lys Tyr Pro
        50                  55                  60

Ala Val Gly Gly Phe Asp Phe Met Asn Tyr Ser Pro Ser Arg Val Glu
65                  70                  75                  80

Arg Gly Ala Glu Cys Gln Asp Thr Asp Leu Ala Ile Lys Trp Trp Asn
                85                  90                  95

Arg Gly Gly Ile Val Thr Phe Cys Trp His Trp Asn Ala Pro Lys Asp
            100                 105                 110

Leu Val Asp Leu Pro Pro Asp Arg Thr Trp Gly Arg Gly Phe Tyr Thr
        115                 120                 125

Asn Ala Thr Thr Phe Asp Ile Ala Arg Ala Met Ala Glu Pro Ser Ser
    130                 135                 140
```

```
Glu Glu Tyr Gly Leu Ile Ile Arg Asp Ile Asp Ala Ile Ala Ala Glu
145                 150                 155                 160

Leu Lys Arg Leu Gln Asp Ala Gly Ile Pro Val Leu Trp Arg Pro Leu
                165                 170                 175

His Glu Ala Ser Gly Gly Trp Phe Trp Trp Gly Ala Lys Gly Pro Glu
            180                 185                 190

Pro Cys Ile Ala Leu Trp Lys Leu Met Tyr Glu Arg Met Thr His His
        195                 200                 205

His Glu Leu Asn Asn Leu Ile Trp Val Trp Asn Gly Gln His Lys Asp
        210                 215                 220

Trp Tyr Pro Gly Asp Ser Tyr Val Asp Ile Ile Gly Glu Asp Ile Tyr
225                 230                 235                 240

Pro Pro Ala Arg Asp Tyr Gly Ser Gln Ser Glu Arg Phe Arg Thr Ala
                245                 250                 255

Ala Ser Tyr Thr Asp Ala Ala Lys Ile Ile Ala Leu Thr Glu Asn Gly
            260                 265                 270

Val Ile Pro Asp Pro Asp Leu Met Gln Glu Asp Gly Cys Pro Trp Ala
        275                 280                 285

Trp Asn Cys Thr Trp Tyr Gly Asn Phe Val Phe Thr Gly Glu Gly Asn
290                 295                 300

Asn Arg Arg Tyr Ser Glu Glu Tyr Thr Asp Glu Leu Gln Leu Ile Arg
305                 310                 315                 320

Thr Tyr His His Pro Tyr Thr Val Thr Leu Asp Glu Leu Pro Asp Leu
                325                 330                 335

Lys Gly

<210> SEQ ID NO 18
<211> LENGTH: 398
<212> TYPE: PRT
<213> ORGANISM: Dictyoglomus thermophilum

<400> SEQUENCE: 18

Met His Glu Leu Ile Ile Gly Tyr Ala Ala Pro Tyr Gly Tyr Lys Glu
1               5                   10                  15

Asn Ser Leu Tyr Val Asn Gly Glu Phe Gln Thr Asn Val Lys Phe Pro
                20                  25                  30

Gln Ser Gln Lys Phe Thr Thr Val Tyr Ala Gly Leu Ile Pro Leu Lys
            35                  40                  45

Asn Gly Lys Asn Thr Ile Ser Ile Val Lys Ser Trp Gly Trp Phe Leu
        50                  55                  60

Leu Asp Tyr Phe Lys Ile Lys Lys Ala Glu Ile Pro Thr Met Asn Pro
65                  70                  75                  80

Thr Asn Lys Leu Val Thr Pro Asn Pro Ser Lys Glu Ala Gln Lys Leu
                85                  90                  95

Met Asp Tyr Leu Val Ser Ile Tyr Gly Lys Tyr Thr Leu Ser Gly Gln
            100                 105                 110

Met Gly Tyr Lys Asp Ala Phe Trp Ile Trp Asn Ile Thr Asp Lys Phe
        115                 120                 125

Pro Ala Ile Cys Gly Phe Asp Met Met Asp Tyr Ser Pro Ser Arg Val
        130                 135                 140

Glu Arg Gly Ala Ser Ser Arg Asp Val Glu Asp Ala Ile Asp Trp Trp
145                 150                 155                 160

Asn Met Gly Gly Ile Val Gln Phe Gln Trp His Trp Asn Ala Pro Lys
                165                 170                 175
```

```
Gly Leu Tyr Asp Thr Pro Gly Lys Glu Trp Trp Arg Gly Phe Tyr Thr
            180                 185                 190

Asn Ala Thr Ser Phe Asp Ile Glu Tyr Ala Leu Asn His Pro Glu Ser
        195                 200                 205

Glu Asp Tyr Lys Leu Ile Ile Arg Asp Ile Asp Ala Ile Ala Val Gln
    210                 215                 220

Leu Lys Arg Leu Gln Glu Ala Lys Val Pro Ile Leu Trp Arg Pro Leu
225                 230                 235                 240

His Glu Ala Glu Gly Arg Trp Phe Trp Trp Gly Ala Lys Gly Pro Glu
                245                 250                 255

Ala Cys Lys Lys Leu Trp Arg Leu Leu Phe Asp Arg Leu Val Asn Tyr
            260                 265                 270

His Lys Ile Asn Asn Leu Ile Trp Val Trp Thr Thr Thr Asp Ser Pro
        275                 280                 285

Asp Ala Leu Lys Trp Tyr Pro Gly Asp Glu Tyr Val Asp Ile Val Gly
    290                 295                 300

Ala Asp Ile Tyr Leu Lys Asp Lys Asp Tyr Ser Pro Ser Thr Gly Met
305                 310                 315                 320

Phe Tyr Asn Ile Val Lys Leu Phe Gly Gly Lys Lys Leu Val Ala Leu
                325                 330                 335

Thr Glu Asn Gly Ile Ile Pro Asp Pro Asp Leu Met Lys Glu Gln Lys
            340                 345                 350

Ala Tyr Trp Val Trp Phe Met Thr Trp Ser Gly Phe Glu Asn Asp Pro
        355                 360                 365

Asn Lys Asn Glu Ile Ser His Ile Lys Lys Val Phe Asn His Pro Phe
    370                 375                 380

Val Ile Thr Lys Asp Glu Leu Pro Asn Leu Lys Val Glu Glu
385                 390                 395

<210> SEQ ID NO 19
<211> LENGTH: 398
<212> TYPE: PRT
<213> ORGANISM: Dictyoglomus thermophilum

<400> SEQUENCE: 19

Met His Glu Leu Ile Ile Gly Tyr Ala Ala Pro Tyr Gly Tyr Lys Glu
1               5                   10                  15

Asn Ser Leu Tyr Val Asn Gly Phe Gln Thr Asn Val Lys Phe Pro
            20                  25                  30

Gln Ser Gln Lys Phe Thr Thr Val Tyr Ala Gly Leu Ile Pro Leu Lys
        35                  40                  45

Asn Gly Lys Asn Thr Ile Ser Ile Val Lys Ser Trp Gly Trp Phe Leu
50                  55                  60

Leu Asp Tyr Phe Lys Ile Lys Lys Ala Glu Ile Pro Thr Met Asn Pro
65                  70                  75                  80

Thr Asn Lys Leu Val Thr Pro Asn Pro Ser Lys Glu Ala Gln Lys Leu
            85                  90                  95

Met Asp Tyr Leu Val Ser Ile Tyr Gly Lys Tyr Thr Leu Ser Gly Gln
        100                 105                 110

Met Gly Tyr Lys Asp Ala Phe Trp Ile Trp Asn Ile Thr Asp Lys Phe
    115                 120                 125

Pro Ala Ile Cys Gly Phe Asp Met Met Asp Tyr Ser Pro Ser Arg Val
    130                 135                 140

Glu Arg Gly Ala Ser Ser Arg Asp Val Glu Asp Ala Ile Asp Trp Trp
145                 150                 155                 160
```

Asn Met Gly Gly Ile Val Gln Phe Gln Trp His Trp Asn Ala Pro Lys
            165                 170                 175

Gly Leu Tyr Asp Thr Pro Gly Lys Glu Trp Trp Arg Gly Phe Tyr Thr
            180                 185                 190

Asn Ala Thr Ser Phe Asp Ile Glu Tyr Ala Leu Asn His Pro Glu Ser
            195                 200                 205

Glu Asp Tyr Lys Leu Ile Ile Arg Asp Ile Asp Ala Ile Ala Val Gln
210                 215                 220

Leu Lys Arg Leu Gln Glu Ala Lys Val Pro Ile Leu Trp Arg Pro Leu
225                 230                 235                 240

His Glu Ala Glu Gly Arg Trp Phe Trp Trp Gly Ala Lys Gly Pro Glu
            245                 250                 255

Ala Cys Lys Lys Leu Trp Arg Leu Leu Phe Asp Arg Leu Val Asn Tyr
            260                 265                 270

His Lys Ile Asn Asn Leu Ile Trp Val Trp Thr Thr Thr Asp Ser Pro
            275                 280                 285

Asp Ala Leu Lys Trp Tyr Pro Gly Asp Glu Tyr Val Asp Ile Val Gly
            290                 295                 300

Ala Asp Ile Tyr Leu Lys Asp Lys Asp Tyr Ser Pro Ser Thr Gly Met
305                 310                 315                 320

Phe Tyr Asn Ile Val Lys Leu Phe Gly Gly Lys Lys Leu Val Ala Leu
            325                 330                 335

Thr Glu Asn Gly Ile Ile Pro Asp Pro Asp Leu Met Lys Glu Gln Lys
            340                 345                 350

Ala Tyr Trp Val Trp Phe Met Thr Trp Ser Gly Phe Glu Asn Asp Pro
            355                 360                 365

Asn Lys Asn Glu Ile Ser His Ile Lys Lys Val Phe Asn His Pro Phe
            370                 375                 380

Val Ile Thr Lys Asp Glu Leu Pro Asn Leu Lys Val Glu Glu
385                 390                 395

<210> SEQ ID NO 20
<211> LENGTH: 487
<212> TYPE: PRT
<213> ORGANISM: Paenibacillus sp. oral taxon 786

<400> SEQUENCE: 20

Ser Ala Lys Arg Met Ala Gly Ile Thr Val Thr Tyr Lys Glu Ala Val
1               5                   10                  15

Leu Glu Gly Tyr Gly Ile Glu Lys Arg Glu Arg Val Pro Glu Ala Asn
            20                  25                  30

Asp Thr Leu Tyr Asn Gly Glu Gly Tyr Val Ser Phe Phe Glu Glu
            35                  40                  45

Asn Lys Ser Thr Ser Asp Pro Ile Gly Ser Ala Thr Phe Lys Val Asn
50                  55                  60

Val Pro Glu Ala Gly Leu Tyr Ala Leu Thr Val Gly Tyr Tyr Ile Pro
65                  70                  75                  80

Gln Gly Tyr Gly Asn Lys Ala Thr Val Ile Gln Val Asn Gly Met Gly
            85                  90                  95

Thr Glu Glu Leu Thr Leu Glu Ala Leu Pro Ala Glu Gln Val Arg Glu
            100                 105                 110

Glu Lys Met Leu Thr Lys Ile Met Leu Asn Ala Gly Ser Asn Thr Ile
            115                 120                 125

Gln Phe Met Arg Gly Trp Gly Tyr Tyr Gly Ile Glu Tyr Ile Lys Leu

```
                  130                 135                 140
Asp Leu Ala Asp Pro Pro Glu Pro Gly Tyr Leu Lys Ala Thr Asp Ile
145                 150                 155                 160

Leu Thr Asn Pro Asn Ala Thr Leu Glu Ala Arg Ala Leu Met Asn Tyr
                165                 170                 175

Leu Leu Asn Gln Tyr Gly Arg Lys Ile Ile Ser Gly Gln His Thr Leu
            180                 185                 190

Gln Asp Ala Glu Trp Ile Asn Gln Gln Ile Gly Lys Tyr Pro Ala Ile
        195                 200                 205

Leu Ser Ser Asp Leu Met Asp Tyr Ser Pro Ser Arg Val Glu Lys Gly
    210                 215                 220

Ala Val Ser Ser Glu Ile Glu Lys Leu Leu Gln Trp His Glu Arg Gly
225                 230                 235                 240

Gly Ile Val Ser Leu Cys Trp His Trp Asn Ala Pro Lys Gly Ile Gly
                245                 250                 255

Gly Asp Glu Pro Asp Arg Glu Trp Trp Arg Gly Phe Tyr Thr Glu Phe
            260                 265                 270

Thr Thr Phe Asp Val Glu Tyr Ala Leu Gln His Pro Glu Ser Glu Asp
        275                 280                 285

Tyr Gln Leu Leu Leu Arg Asp Ile Asp Ala Ile Ala Val Gln Leu Lys
    290                 295                 300

Arg Leu Gln Asp His His Val Pro Val Leu Trp Arg Pro Leu His Glu
305                 310                 315                 320

Ala Glu Gly Gly Trp Phe Trp Trp Gly Ala Lys Gly Pro Glu Pro Ala
                325                 330                 335

Lys Gln Leu Tyr Arg Leu Met Tyr Asp Arg Leu Thr Asn His His Lys
            340                 345                 350

Leu Asn Asn Leu Ile Trp Val Trp Asn Ser Val Gln Glu Glu Trp Tyr
        355                 360                 365

Pro Gly Asp Asp Val Val Asp Val Val Thr Val Asp Ile Tyr Asn Pro
    370                 375                 380

Thr Gly Asp Tyr His Pro Asn Ile Ser Lys Tyr Asp Lys Leu Leu Ser
385                 390                 395                 400

Leu Thr Ser Ser Lys Lys Ile Ala Ala Leu Ala Glu Asn Gly Pro Ile
                405                 410                 415

Pro Asp Pro Asp Leu Leu Gln Gly Tyr Gly Ala Asp Trp Ser Phe Phe
            420                 425                 430

Thr Thr Trp Thr Gly Asp His Ile Arg Asp Gly Lys Thr Asn Thr Leu
        435                 440                 445

Glu His Leu His Lys Val Tyr His His Asp Tyr Val Leu Thr Leu Asp
    450                 455                 460

Glu Leu Pro Ala Asp Leu Phe Thr Ser Leu Ile Tyr Lys Ala Glu Tyr
465                 470                 475                 480

Gly Gln Pro Phe Gly Leu Phe
                485

<210> SEQ ID NO 21
<211> LENGTH: 471
<212> TYPE: PRT
<213> ORGANISM: Bacillus sp.

<400> SEQUENCE: 21

Glu Pro Val Asn Pro Thr Leu Pro Thr Ile Phe Ile Glu Ala Glu Glu
1               5                   10                  15
```

-continued

```
Asp Tyr Glu Ala Thr Gly Asn Val Ser Val Thr Asn Glu Ile Glu Gly
            20                  25                  30

Tyr Ser Gly Ala Gly Tyr Leu Phe Asn Gln Glu Gly Thr Ile His Trp
        35                  40                  45

Asn Val Thr Ser Pro Glu Thr Ser Ile Tyr Glu Val Ile Val Ala Tyr
    50                  55                  60

Ala Ala Pro Tyr Gly Asp Lys Gln Thr Asn Leu Thr Val Asn Gly Gln
65                  70                  75                  80

Gly Thr Val Asn Leu Asp Leu Lys Glu Thr Glu Val Phe Val Glu Leu
                85                  90                  95

Asn Val Gly Ile Val Ser Leu Asn Glu Gly Glu Asn Thr Leu Thr Leu
            100                 105                 110

His Ser Gly Trp Gly Trp Tyr Asn Ile Asp Tyr Ile Lys Leu Val Pro
        115                 120                 125

Val Val Ser Ser Asp Pro Glu Pro His Gln Val Glu Lys Thr Leu Val
    130                 135                 140

Asn Pro Asp Ala Ser Pro Glu Ala Arg Ala Leu Ile Asn Tyr Leu Val
145                 150                 155                 160

Asp Gln Tyr Gly Asn Lys Ile Leu Ser Gly Gln Thr Glu Leu Lys Asp
                165                 170                 175

Ala Arg Trp Ile His Glu Gln Val Gly Lys Tyr Pro Ala Val Met Ala
            180                 185                 190

Val Asp Phe Met Asp Tyr Ser Pro Ser Arg Val Val His Gly Ala Thr
        195                 200                 205

Gly Thr Ala Val Glu Glu Ala Ile Glu Trp Ala Glu Met Gly Gly Ile
    210                 215                 220

Ile Thr Phe His Trp His Trp Asn Ala Pro Lys Asp Leu Leu Asn Val
225                 230                 235                 240

Pro Gly Asn Glu Trp Trp Ser Gly Phe Tyr Thr Arg Ala Thr Thr Phe
                245                 250                 255

Asp Val Glu Tyr Ala Leu Glu Asn Arg Glu Ser Glu Asp Phe Gln Leu
            260                 265                 270

Leu Ile Ser Asp Met Asp Val Ile Ala Glu Gln Leu Lys Arg Leu Gln
        275                 280                 285

Ala Glu Asn Ile Pro Val Leu Trp Arg Pro Leu His Glu Ala Glu Gly
    290                 295                 300

Gly Trp Phe Trp Trp Gly Ala Lys Gly Pro Glu Ala Ala Ile Glu Leu
305                 310                 315                 320

Tyr Arg Leu Met Tyr Asp Arg Tyr Thr Asn His His Lys Leu Asn Asn
                325                 330                 335

Leu Ile Trp Met Trp Asn Ser Glu Ala Glu Glu Trp Tyr Pro Gly Asp
            340                 345                 350

Asp Val Val Asp Met Ile Ser Thr Asp Ile Tyr Asn Pro Val Gly Asp
        355                 360                 365

Phe Ser Pro Ser Ile Asn Lys Tyr Glu His Leu Lys Glu Leu Val Gln
    370                 375                 380

Asp Lys Lys Leu Val Ala Leu Pro Glu Thr Gly Ile Ile Pro Asp Pro
385                 390                 395                 400

Asp Gln Leu Gln Leu Phe Asn Ala Asn Trp Ser Trp Phe Ala Thr Trp
                405                 410                 415

Thr Gly Asp Tyr Ile Arg Asp Gly Ile Ser Asn Pro Ile Glu His Leu
            420                 425                 430

Gln Lys Val Phe His His Asp Tyr Val Ile Thr Leu Asp Glu Leu Pro
```

```
                    435                 440                 445
Glu Asn Leu Ser Arg Tyr Gly Leu Ser Glu Gly Val Trp Lys Ser Asp
    450                 455                 460

Ala Asp Leu Ser Val Lys Thr
465                 470

<210> SEQ ID NO 22
<211> LENGTH: 492
<212> TYPE: PRT
<213> ORGANISM: Paenibacillus polymyxa

<400> SEQUENCE: 22

Val Pro Arg Ala Pro Val Asp Gly Pro Asp Arg Tyr Glu Ala Glu Asp
1               5                   10                  15

Gly Thr Leu Lys Gly Thr Val Val Glu Ser Ser Gly Thr Gly Phe Ser
            20                  25                  30

Gly Thr Gly Tyr Val Thr Asn Phe His Asn Ala Gly Asp Ser Leu Thr
        35                  40                  45

Met Thr Ile Gln Ala Pro Thr Ala Gly Leu Tyr Asn Leu Thr Ile Gly
    50                  55                  60

Tyr Arg Ser Pro His Asp Asp Lys Arg Thr Asn Phe Ser Leu Asn Gly
65                  70                  75                  80

Lys Ala Ser Gly Glu Leu Val Leu Trp Lys Thr Ala Asp Phe Lys Glu
                85                  90                  95

Thr Ser Gly Gly Lys Val Leu Leu Asn Ala Gly Ala Asn Thr Ile Gly
            100                 105                 110

Phe Glu Thr Gly Trp Gly Trp Tyr Asp Ile Asp Tyr Val Lys Leu Glu
        115                 120                 125

Pro Ala Ala Asp Arg Pro Pro His Ala Val Thr Lys Thr Leu Ile Asn
130                 135                 140

Pro Asn Ala Thr Val Glu Ala Lys Ala Leu Met Asn Tyr Leu Val Asp
145                 150                 155                 160

Gln Tyr Gly Lys Asn Met Leu Ser Gly Gln Glu Asp Met Pro Glu Ile
                165                 170                 175

Asp Trp Leu Gln Ala Asn Val Gly Lys Lys Pro Ala Ile Ala Ala Leu
            180                 185                 190

Asp Leu Ile Asp Tyr Ser Pro Ser Arg Ala Glu His Gly Leu Ser Ser
        195                 200                 205

Thr Glu Thr Glu Lys Ala Ile Glu Trp Asp Lys Gln Gly Gly Ile Val
210                 215                 220

Thr Phe Ala Trp His Trp Asn Ala Pro Lys Gly Leu Ile Asp Thr Gln
225                 230                 235                 240

Gly Lys Glu Trp Trp Arg Gly Phe Tyr Ala Asp Ser Thr Thr Phe Asp
                245                 250                 255

Ile Glu Tyr Ala Met Asn His Pro Glu Ser Glu Asp Tyr Lys Leu Leu
            260                 265                 270

Ile Arg Asp Ile Asp Val Ile Ala Gly Gln Leu Lys Lys Leu Gln Asp
        275                 280                 285

Ala Lys Val Pro Val Leu Phe Arg Pro Leu His Glu Ala Glu Gly Lys
290                 295                 300

Trp Phe Trp Trp Gly Ala Lys Gly Pro Glu Pro Val Lys Lys Leu Tyr
305                 310                 315                 320

Ile Leu Met His Asp Arg Leu Thr Asn Val His Lys Leu Asn Asn Leu
                325                 330                 335
```

```
Ile Trp Val Trp Asn Ser Val Ala Pro Asp Trp Tyr Pro Gly Asp Glu
                340                 345                 350

Tyr Val Asp Ile Leu Ser Phe Asp Ser Tyr Pro Gln Ala Gly Asp Tyr
            355                 360                 365

Ser Pro Gln Ile Ala Lys Tyr Glu Asp Leu Val Thr Leu Gly Lys Asp
        370                 375                 380

Lys Lys Leu Val Cys His Glu Arg Lys Arg Thr Tyr Pro Gly Pro Gly
385                 390                 395                 400

Ser Asp Glu Gly Val Ser Ser Pro Leu Glu Leu Val Arg Tyr Met Val
                405                 410                 415

Trp Gly Phe Leu Glu Arg Arg Gln Thr Lys Gln Ser Leu Glu His Leu
            420                 425                 430

Lys Lys Val Tyr Asn His Pro Asn Val Ile Thr Leu Glu Lys Leu Pro
        435                 440                 445

Thr Asn Leu Lys Thr Tyr Gly Ile Thr Glu Gln Pro Ser Val Pro Gly
    450                 455                 460

Ser Phe Thr Leu Asn Ala Ala Gly Glu Thr Ala Lys Val Lys Leu Ser
465                 470                 475                 480

Trp Thr Ala Ser Ala Asn Ala Ala Ser Tyr Glu Val
                485                 490

<210> SEQ ID NO 23
<211> LENGTH: 457
<212> TYPE: PRT
<213> ORGANISM: Paenibacillus polymyxa

<400> SEQUENCE: 23

Glu Phe Ala Ser Leu Pro Ala Ala Ile Ser Lys Ile Glu Ala Glu Asp
1               5                   10                  15

Gly Val Ile Thr Gly Glu Val Ser Ile Glu Asp Ala Val Thr Gly Tyr
                20                  25                  30

Ser Gly Thr Gly Tyr Ala Ala Phe Lys Ser Thr Gly Ser Leu Thr Phe
            35                  40                  45

Ala Tyr Asn Ala Pro Ser Ser Gly Leu Tyr Thr Leu Ala Ile Gly Tyr
        50                  55                  60

Ser Asn Pro Asn Gly Asp Lys Lys Thr His Leu Val Val Asn Gly Gln
65                  70                  75                  80

Thr Ser Glu Ile Ser Leu Pro Lys Thr Ala Ser Tyr Thr Glu Val Ser
                85                  90                  95

Gly Gly Lys Leu Met Leu Ser Ser Gly Asn Asn Thr Ile Gln Phe Asn
            100                 105                 110

Val Asp Ser Asp Gln Tyr His Ile Asp Tyr Val Lys Leu Ser Ala Val
        115                 120                 125

Ser Pro Pro Lys Leu His Gln Ile Lys Lys Lys Pro Val Asn Pro Asn
    130                 135                 140

Ala Thr Ala Glu Thr Lys Ala Leu Met Ser Tyr Leu Val Asp Ser Tyr
145                 150                 155                 160

Ser Ser His Ile Leu Ser Gly Gln His Thr Leu Glu Asp Ala Gln Trp
                165                 170                 175

Ile Lys Asp Gln Thr Gly Lys Tyr Pro Ala Met Leu Ser Thr Asp Met
            180                 185                 190

Met Asp Tyr Ser Pro Ser Arg Val Glu His Gly Ala Thr Ser Asn Glu
        195                 200                 205

Val Glu Lys Ala Ile Gln Trp Ser Gln Glu Gly Gly Leu Val Thr Phe
    210                 215                 220
```

Ala Trp His Trp Asn Ala Pro Lys Gly Leu Gln Asp Ile Pro Gly Lys
225                 230                 235                 240

Glu Trp Trp Arg Gly Phe Tyr Thr Asp Ala Thr Thr Phe Asp Val Gln
            245                 250                 255

Tyr Ala Leu Asn His Pro Glu Ser Glu Glu Tyr Gln Leu Ile Leu Arg
        260                 265                 270

Asp Ile Asp Ala Ile Ala Ala Gln Leu Lys Arg Leu Gln Asp Ala His
    275                 280                 285

Val Pro Val Leu Trp Arg Pro Leu His Glu Ala Glu Gly Lys Trp Phe
290                 295                 300

Trp Trp Gly Ala Gln Gly Pro Asp Ser Ala Lys Gln Leu Tyr Arg Ile
305                 310                 315                 320

Met Tyr Asp Arg Leu Thr His Tyr His His Leu Asn Asn Leu Ile Trp
                325                 330                 335

Val Trp Asn Ser Glu Ser Pro Glu Trp Tyr Pro Gly Asp Asp Val Val
            340                 345                 350

Asp Ile Val Ser Val Asp Ile Tyr Asn Gln Ala Ala Asn Tyr Ser Pro
        355                 360                 365

Ser Ile Gly Lys Tyr Asp Ser Leu Val Lys Leu Val Gln Gly Lys Lys
    370                 375                 380

Leu Val Gly Leu Ser Glu Asn Gly Pro Ile Ser Asp Pro Glu Leu Leu
385                 390                 395                 400

Gln Ser Tyr Ser Ala His Trp Leu Phe Phe Thr Thr Trp Thr Gly Asp
                405                 410                 415

Phe Val Arg Asn Gly Gln Tyr Asn Ser Leu Asp His Leu Ile Lys Val
            420                 425                 430

Phe Asn Ser Asp Tyr Val Ile Thr Arg Asp Glu Leu Pro Gln Asp Leu
        435                 440                 445

Phe Thr Ser Ser Lys Asn Glu Ala Glu
    450                 455

<210> SEQ ID NO 24
<211> LENGTH: 457
<212> TYPE: PRT
<213> ORGANISM: Paenibacillus polymyxa

<400> SEQUENCE: 24

Glu Phe Ala Asn Leu Pro Ala Ala Ile Ser Lys Met Glu Ala Glu Asp
1               5                   10                  15

Gly Ala Ile Thr Gly Lys Val Ser Ile Glu Ala Ala Asp Thr Gly Tyr
            20                  25                  30

Ser Gly Thr Gly Tyr Ala Thr Phe Lys Gly Thr Gly Ser Leu Thr Phe
        35                  40                  45

Ala Tyr Asn Ala Ala Ser Ser Gly Leu Tyr Asn Leu Ala Ile Gly Tyr
    50                  55                  60

Ser Asn Pro Asn Gly Asp Lys Lys Thr Gln Leu Val Val Asn Gly Gln
65                  70                  75                  80

Thr Ser Glu Thr Ser Leu Pro Thr Thr Ala Ser Tyr Thr Glu Val Ser
                85                  90                  95

Gly Gly Lys Leu Met Leu Ser Ala Gly Asn Asn Thr Ile Gln Phe Asn
            100                 105                 110

Val Asp Ser Asp Gln Tyr His Ile Asp Tyr Val Lys Leu Ser Ala Val
        115                 120                 125

Ser Pro Pro Lys Leu Tyr Gln Ile Glu Lys Lys Pro Val Asn Pro Asn

```
                130            135            140
Ala Thr Ala Glu Thr Lys Ala Leu Met Gly Tyr Leu Val Asp Ser Tyr
145                150                155                160

Gly Ser Asn Ile Leu Ser Gly Gln His Thr Leu Glu Asp Ala Gln Trp
                165                170                175

Ile Lys Asp Gln Thr Gly Lys Tyr Pro Ala Ile Leu Ser Thr Asp Met
                180                185                190

Met Asp Tyr Ser Pro Ser Arg Ile Glu His Gly Ala Thr Ser Thr Glu
                195                200                205

Val Glu Lys Ala Ile Gln Trp Ala Lys Glu Gly Ile Val Thr Phe
    210                215                220

Ala Trp His Trp Asn Ala Pro Lys Gly Leu His Asp Ile Pro Gly Lys
225                230                235                240

Glu Trp Trp Arg Gly Phe Tyr Thr Asp Ala Thr Thr Phe Asp Val Gln
                245                250                255

Tyr Ala Leu Thr His Pro Glu Ser Glu Glu Tyr Gln Leu Ile Leu Arg
                260                265                270

Asp Ile Asp Ala Ile Ala Ala Gln Leu Lys Arg Leu Gln Asp Ala His
                275                280                285

Val Pro Val Leu Trp Arg Pro Leu His Glu Ala Glu Gly Lys Trp Phe
                290                295                300

Trp Trp Gly Ala Gln Gly Pro Asp Ser Ala Lys Gln Leu Tyr His Ile
305                310                315                320

Met Tyr Asp Arg Leu Thr Asn Tyr His His Leu Asn Asn Leu Ile Trp
                325                330                335

Val Trp Asn Ser Glu Ser Pro Glu Trp Tyr Pro Gly Asp Asp Val Val
                340                345                350

Asp Ile Val Ser Val Asp Ile Tyr Asn Gln Ala Ala Asn Tyr Ser Pro
                355                360                365

Ser Ile Gly Lys Tyr Asp Ser Leu Val Asn Leu Val Gln Gly Lys Lys
                370                375                380

Leu Val Gly Leu Ser Glu Asn Gly Pro Ile Gly Asp Pro Glu Leu Leu
385                390                395                400

Gln Thr Tyr Ser Ala His Trp Leu Phe Phe Thr Thr Trp Thr Gly Asp
                405                410                415

Phe Ile Arg Asn Gly Gln Tyr Asn Ser Leu Asp His Leu Ile Lys Val
                420                425                430

Phe Asn Ser Asp Tyr Val Ile Thr Arg Asp Glu Leu Pro Gln Asp Leu
                435                440                445

Phe Thr Ser Ser Lys Asn Glu Ala Glu
450                455

<210> SEQ ID NO 25
<211> LENGTH: 444
<212> TYPE: PRT
<213> ORGANISM: Dictyoglomus turgidum

<400> SEQUENCE: 25

Val Glu Ala Glu Asn Gly Val Leu Asn Gly Thr Tyr Val Ala Lys Asn
1               5                  10                  15

Leu Pro Gly Tyr Gln Gly Thr Gly Tyr Val Asp Gly Phe Asp Arg Asp
                20                  25                  30

Gly Asp Ser Cys Thr Ile Thr Phe Glu Val Lys Glu Ala Gly Met Tyr
                35                  40                  45
```

```
Glu Leu Ile Ile Gly Tyr Ala Ala Pro Tyr Gly Tyr Lys Glu Asn Ser
 50                  55                  60

Leu Tyr Val Asn Gly Val Phe Gln Thr Asn Val Lys Phe Pro Pro Ser
 65                  70                  75                  80

Gln Ser Phe Thr Thr Val Tyr Gly Gly Leu Ile Pro Leu Lys Ser Gly
                 85                  90                  95

Lys Asn Thr Ile Ser Ile Val Lys Ser Trp Gly Trp Phe Leu Leu Asp
                100                 105                 110

Tyr Phe Lys Ile Lys Lys Ala Glu Leu Pro Thr Met Asn Pro Thr Asn
            115                 120                 125

Lys Leu Val Thr Pro Asn Pro Ser Lys Glu Ala Gln Lys Leu Met Asp
130                 135                 140

Tyr Leu Val Ser Ile Tyr Gly Lys Tyr Thr Leu Ser Gly Gln Met Gly
145                 150                 155                 160

Tyr Lys Asp Ala Phe Trp Ile Trp Asn Ile Thr Asp Lys Phe Pro Ala
                165                 170                 175

Ile Cys Gly Phe Asp Met Ile Asp Tyr Ser Pro Ser Arg Val Glu Arg
                180                 185                 190

Gly Ala Ser Ser Arg Asp Val Glu Asp Ala Ile Asp Trp Trp Asn Met
                195                 200                 205

Gly Gly Ile Val Gln Phe Gln Trp His Trp Asn Ala Pro Lys Gly Leu
210                 215                 220

Tyr Asp Thr Pro Gly Lys Glu Trp Trp Arg Gly Phe Tyr Thr Asn Ala
225                 230                 235                 240

Thr Ser Phe Asp Ile Glu Tyr Ala Leu Asn His Pro Glu Ser Glu Asp
                245                 250                 255

Tyr Lys Leu Ile Ile Arg Asp Ile Asp Ala Ile Ala Val Gln Leu Lys
                260                 265                 270

Arg Leu Gln Glu Ala Arg Val Pro Ile Leu Trp Arg Pro Leu His Glu
            275                 280                 285

Ala Glu Gly Arg Trp Phe Trp Trp Gly Ala Lys Gly Pro Glu Pro Cys
290                 295                 300

Lys Lys Leu Trp Arg Leu Leu Phe Asp Arg Leu Val Asn Tyr His Lys
305                 310                 315                 320

Ile Asn Asn Leu Ile Trp Val Trp Thr Thr Thr Asp Ser Pro Asp Ala
                325                 330                 335

Leu Lys Trp Tyr Pro Gly Asp Glu Tyr Val Asp Ile Val Gly Ala Asp
                340                 345                 350

Val Tyr Leu Asn Asp Lys Asn Tyr Ser Pro Ser Thr Gly Met Phe Tyr
                355                 360                 365

Asn Ile Val Lys Ile Phe Gly Gly Lys Lys Leu Val Ala Leu Thr Glu
370                 375                 380

Asn Gly Ile Ile Pro Asp Pro Asp Leu Met Lys Glu Gln Lys Ala Tyr
385                 390                 395                 400

Trp Ala Trp Phe Met Thr Trp Ser Gly Phe Glu Asn Asp Pro Asn Lys
                405                 410                 415

Asn Glu Ile Ser His Ile Lys Lys Val Phe Asn His Pro Phe Val Ile
                420                 425                 430

Thr Lys Asp Glu Leu Pro Asn Leu Lys Val Glu Glu
                435                 440

<210> SEQ ID NO 26
<211> LENGTH: 446
<212> TYPE: PRT
```

<213> ORGANISM: Bacillus megaterium

<400> SEQUENCE: 26

```
Phe Glu Ala Glu Ala Lys Leu Ser Gly Val Glu Val Asp Asn Lys
1               5                   10                  15

Ile Lys Ala Tyr Ser Ser Glu Gly Tyr Val Thr Lys Phe Asn Lys Ser
            20                  25                  30

Asp Asp Asn Ile Val Phe Asp Val Asn Val Pro Arg Glu Gly Ile Tyr
            35                  40                  45

Asn Ile Ser Ile Arg Tyr Tyr Ile Pro Lys Thr Ser Gly Glu Lys Tyr
        50                  55                  60

Thr Leu Ile Asn Val Asn Gly Gly Tyr Leu Arg Lys Phe Ala Leu Pro
65                  70                  75                  80

Ala Leu Asn Thr Phe Gln Glu Ile Ser Val Gly Asn Phe Ser Leu Lys
                85                  90                  95

Lys Gly Glu Asn Asn Ile Met Leu Ile Ser Glu Trp Gly Phe Tyr Asn
            100                 105                 110

Ile Asp Tyr Ile Arg Ile Gln Asp Phe Pro Val Lys Gly Lys Leu Thr
        115                 120                 125

Ile Asn Asp Glu Leu Val Asn Lys Lys Ala Asn Asn Glu Thr Lys Lys
130                 135                 140

Leu Met Lys Phe Leu Val Ser Ile Gln Lys Ser His Ile Leu Ser Gly
145                 150                 155                 160

Gln Gln Gly Leu Lys Glu Val Glu Trp Ile Asp Glu His Leu Gly Lys
                165                 170                 175

Lys Pro Ala Val Val Gly Phe Asp Phe Arg Asp Tyr Ser Leu Ser Arg
            180                 185                 190

Val Arg Arg Gly Val Lys Ser Asn Glu Thr Glu Glu Ala Ile Lys Trp
        195                 200                 205

His Gln Glu Gly Gly Ile Val Ser Phe Ser Trp His Trp Asn Ala Pro
210                 215                 220

Lys Asp Leu Ile Asp Glu Pro Gly Lys Glu Trp Ser Glu Gly Phe Arg
225                 230                 235                 240

Thr Lys Ala Thr Thr Phe Asp Ile Gln Tyr Ala Leu Ser His Pro Thr
                245                 250                 255

Ser Glu Asp Tyr Lys Leu Leu Leu Lys Asp Ile Asp Ala Ile Ala Leu
            260                 265                 270

Gln Leu Thr Lys Leu Gln Glu Ala Asn Val Pro Val Leu Phe Arg Pro
        275                 280                 285

Leu His Glu Ala Glu Gly Gly Trp Phe Trp Trp Gly Ala Lys Gly Pro
290                 295                 300

Glu Pro Ala Lys Glu Leu Tyr Arg Leu Ile Tyr Asp Arg Ile Thr Asn
305                 310                 315                 320

Tyr His Lys Ile Asn Asn Val Ile Trp Ile Trp Asn Ser Ser Ser Lys
                325                 330                 335

Glu Trp Tyr Pro Gly Asn Lys Tyr Val Asp Ile Val Ser Tyr Asp Ser
            340                 345                 350

Tyr Pro Asp Ala Gly Asp Tyr Arg Pro Leu Ile Glu Lys Tyr Ala Glu
        355                 360                 365

Leu Thr Ser Leu Val Asn Asp Glu Lys Leu Ile Ala Leu Ser Glu Asn
370                 375                 380

Gly Pro Ile Pro Asp Pro Asn Leu Leu Lys Glu Tyr Gln Val Asn Trp
385                 390                 395                 400
```

```
Ser Trp Phe Leu Thr Trp Gln Glu Lys Phe Leu Lys Asp Gly Lys Thr
                405                 410                 415

Asn Ser Leu Glu His Leu Ser Asn Val Tyr Asn Asn Asp Tyr Val Ile
            420                 425                 430

Thr Leu Asp Lys Leu Gln Lys Tyr Lys Leu Tyr Asn Ser Lys
        435                 440                 445

<210> SEQ ID NO 27
<211> LENGTH: 452
<212> TYPE: PRT
<213> ORGANISM: Acetivibrio cellulolyticus

<400> SEQUENCE: 27

Val Tyr Glu Val Glu Asn Gly Arg Leu Thr Gly Thr Asn Ile Leu Ser
1               5                   10                  15

Ser Arg Ala Gly Phe Ser Gly Thr Gly Tyr Val Ser Gly Phe Asp Asn
            20                  25                  30

Asp Gly Asp Ser Val Ala Ile Asn Leu Thr Ile Gly Ser Thr Gly Leu
        35                  40                  45

Tyr Tyr Leu Ser Ile Gly Tyr Ala Ser Glu Phe Gly Asp Lys Thr Asn
    50                  55                  60

Asp Ile Tyr Val Asn Gly Asn Lys Gln Ala Ser Val Glu Phe Lys Gln
65                  70                  75                  80

Ser Ala Val Phe Thr Glu Ile Ser Val Gly Lys Ile Met Leu Asn Ser
                85                  90                  95

Gly Ser Asn Glu Ile Lys Ile Val Lys Ser Trp Gly Trp Phe Asp Val
            100                 105                 110

Asp Tyr Phe Lys Val Glu Lys Ala Pro Glu Asp Pro Pro Leu Ser Val
        115                 120                 125

Ser Asp Ser Leu Val Asn Pro Asn Ala Thr Met Glu Ala Arg Asn Leu
    130                 135                 140

Met Ser Phe Leu Ala Arg Asn Tyr Gly Lys Ser Ile Ile Ala Gly Leu
145                 150                 155                 160

Gln Asp Val Asp Lys Thr Gln Trp Leu Ser Glu Asn Thr Gly Arg Glu
                165                 170                 175

Pro Ala Leu Gly Gly Phe Asp Phe Met Asp Tyr Ser Pro Ser Arg Val
            180                 185                 190

Glu Phe Gly Thr Lys Ser Ser Glu Thr Asp Lys Ala Ile Glu Trp Trp
        195                 200                 205

Asn Ser Gly Gly Ile Val Thr Phe Cys Trp His Trp Asn Ala Pro Thr
    210                 215                 220

Asp Leu Ile Asn Gln Thr Gly Lys Glu Trp Trp Arg Gly Phe Tyr Thr
225                 230                 235                 240

Asp Ser Thr Asn Phe Asp Leu Ser Ala Ala Ile Ser Asn Pro Asp Ser
                245                 250                 255

Glu Asn Tyr Lys Leu Leu Ile Arg Asp Ile Asp Ala Ile Ala Val Gln
            260                 265                 270

Leu Lys Lys Leu Gln Asp Ala Gly Val Pro Val Leu Trp Arg Pro Leu
    275                 280                 285

His Glu Ala Gln Gly Gly Trp Phe Trp Trp Gly Ala Lys Gly Pro Asp
290                 295                 300

Val Cys Lys Lys Leu Tyr Leu Leu Met Tyr Asp Arg Leu Thr Asn Tyr
305                 310                 315                 320

Asn Lys Leu Asn Asn Leu Ile Trp Val Trp Thr Ser Ser Asp Asn Gln
                325                 330                 335
```

```
Asp Ala Leu Lys Trp Tyr Pro Gly Asp Gln Tyr Val Asp Ile Ile Gly
            340                 345                 350

Ala Asp Ile Tyr Leu Asn Gly Gly Asp Tyr Ser Ala Ser Ser Ala Thr
            355                 360                 365

Phe Arg Asn Leu Val Ser Leu Tyr Gln Gly Lys Lys Leu Val Thr Met
            370                 375                 380

Ser Glu Asn Gly Thr Leu Pro Asp Pro Asp Lys Leu Ile Ala Glu Lys
385                 390                 395                 400

Ala Gly Trp Ser Trp Phe Cys Thr Trp Val Asp Tyr Ile Thr Asn Ser
            405                 410                 415

Thr Gln Asn Asp Met Gly Gln Val Gln Lys Val Tyr Asn Ser Thr Tyr
            420                 425                 430

Val Lys Thr Lys Asp Glu Leu Asp Leu Ser Val Lys Pro Thr Glu Ile
            435                 440                 445

Pro Ser Ala Thr
    450

<210> SEQ ID NO 28
<211> LENGTH: 413
<212> TYPE: PRT
<213> ORGANISM: Verticillium albo-atrum VaMs.102

<400> SEQUENCE: 28

Thr Gly Asn Ala Thr Lys Val Tyr Glu Ala Glu Asp Ala Thr Leu Val
1               5                   10                  15

Gly Ser Thr Arg Val Ala Thr Glu Leu Ala Gly Phe Thr Gly Thr Gly
            20                  25                  30

Tyr Val Thr Gly Phe Glu Gly Pro Asn Asp Lys Leu Thr Phe Thr Val
            35                  40                  45

Thr Ser Ala Lys Gln Gly Leu Tyr Asp Leu Thr Ile Arg Tyr Ala Gly
    50                  55                  60

Ile Tyr Gly Asn Lys Tyr Thr Asn Ile Val Leu Asn Asn Gly Gly Thr
65                  70                  75                  80

Glu Gln Val Tyr Leu Pro Glu Thr Thr Asp Phe Gln Asn Ala Ala Gly
            85                  90                  95

Gly Gln Val Leu Leu Asn Ala Gly Asp Asn Thr Ile Asp Ile Leu Thr
            100                 105                 110

His Trp Gly Cys Tyr Leu Arg Ser Ile Tyr Gly Lys Lys Ile Leu Ser
            115                 120                 125

Gly Gln Gln Glu Leu Glu Trp Ala Asp Trp Leu Gln Gln Gln Thr Gly
            130                 135                 140

Glu Thr Pro Ala Leu Leu Ala Val Asp Leu Met Asp Tyr Ser Pro Ser
145                 150                 155                 160

Arg Val Glu Arg Gln Gly Gln Val Ala Thr Val Glu Asp Ala Ile
            165                 170                 175

Glu Phe His Asn Arg Gly Gly Ile Val Ser Val Leu Trp His Trp Asn
            180                 185                 190

Ala Pro Val Gly Leu Tyr Asp Thr Pro Glu Gln Arg Trp Trp Ser Gly
            195                 200                 205

Phe Tyr Thr Ala Ala Thr Asp Phe Asn Val Ala Thr Ala Leu Ala Asp
            210                 215                 220

Thr Thr Asn Ala Asn Tyr Thr Leu Leu Ile Arg Asp Ile Asp Ala Ile
225                 230                 235                 240

Ala Val Gln Leu Lys Arg Val Glu Asp Ala Gly Val Pro Val Leu Trp
```

```
            245                 250                 255
Arg Pro Leu His Glu Ala Glu Gly Lys Trp Phe Trp Trp Gly Ala Gln
            260                 265                 270

Gly Pro Glu Pro Val Lys Lys Leu Trp Asn Ile Leu Tyr Glu Arg Leu
        275                 280                 285

Val Asn His His Gly Ile Asn Asn Leu Ile Trp Val Trp Asn Ser Val
    290                 295                 300

Glu Ala Asp Trp Tyr Pro Gly Asp Ala Thr Ile Asp Ile Leu Ser Ala
305                 310                 315                 320

Asp Val Tyr Ser Gln Gly Asn Gly Pro Met Ser Gly Leu Tyr Asn Gln
                325                 330                 335

Leu Val Glu Leu Gly Asn Asp Lys Lys Leu Ile Ala Ala Ser Glu Val
            340                 345                 350

Gly Ala Ala Pro Leu Pro Asp Leu Leu Gln Leu Tyr Glu Ala His Trp
        355                 360                 365

Leu Trp Phe Ala Val Trp Thr Ser Pro Phe Ile Asn Asp Pro Ala Trp
370                 375                 380

Asn Ser Leu Asp Val Leu Arg Glu Val Tyr Gly Ser Asp Tyr Val Leu
385                 390                 395                 400

Thr Leu Ser Glu Ile Gln Gly Trp Gln Ala Ala His Ser
                405                 410
```

<210> SEQ ID NO 29
<211> LENGTH: 438
<212> TYPE: PRT
<213> ORGANISM: Podospora anserina

<400> SEQUENCE: 29

```
Tyr Glu Ala Glu Asp Ala Ile Leu Thr Gly Thr Thr Val Asp Thr Ala
1               5                   10                  15

Gln Val Gly Tyr Thr Gly Arg Gly Tyr Val Thr Gly Phe Asp Glu Gly
            20                  25                  30

Ser Asp Lys Ile Thr Phe Gln Ile Ser Ser Ala Thr Thr Lys Leu Tyr
        35                  40                  45

Asp Leu Ser Ile Arg Tyr Ala Ala Ile Tyr Gly Asp Lys Arg Thr Asn
    50                  55                  60

Val Val Leu Asn Asn Gly Ala Val Ser Glu Val Phe Phe Pro Ala Gly
65                  70                  75                  80

Asp Ser Phe Thr Ser Val Ala Ala Gly Gln Val Leu Leu Asn Ala Gly
                85                  90                  95

Gln Asn Thr Ile Asp Ile Val Asn Asn Trp Gly Trp Tyr Leu Ile Asp
            100                 105                 110

Ser Ile Thr Leu Thr Pro Ser Ala Pro Arg Pro Pro His Asp Ile Asn
        115                 120                 125

Pro Asn Leu Asn Asn Pro Asn Ala Asp Thr Asn Ala Lys Lys Leu Tyr
    130                 135                 140

Ser Tyr Leu Arg Ser Val Tyr Gly Asn Lys Ile Ile Ser Gly Gln Gln
145                 150                 155                 160

Glu Leu His His Ala Glu Trp Ile Arg Gln Gln Thr Gly Lys Thr Pro
                165                 170                 175

Ala Leu Val Ala Val Asp Leu Met Asp Tyr Ser Pro Ser Arg Val Glu
            180                 185                 190

Arg Gly Thr Thr Ser His Ala Val Glu Asp Ala Ile Ala His His Asn
        195                 200                 205
```

```
Ala Gly Gly Ile Val Ser Val Leu Trp His Trp Asn Ala Pro Val Gly
    210                 215                 220

Leu Tyr Asp Thr Glu Glu Asn Lys Trp Trp Ser Gly Phe Tyr Thr Arg
225                 230                 235                 240

Ala Thr Asp Phe Asp Ile Ala Ala Thr Leu Ala Asn Pro Gln Gly Ala
                245                 250                 255

Asn Tyr Thr Leu Leu Ile Arg Asp Ile Asp Ala Ile Ala Val Gln Leu
                260                 265                 270

Lys Arg Leu Glu Ala Ala Gly Val Pro Val Leu Trp Arg Pro Leu His
            275                 280                 285

Glu Ala Glu Gly Gly Trp Phe Trp Trp Gly Ala Lys Gly Pro Glu Pro
290                 295                 300

Ala Lys Gln Leu Trp Asp Ile Leu Tyr Glu Arg Leu Thr Val His His
305                 310                 315                 320

Gly Leu Asp Asn Leu Ile Trp Val Trp Asn Ser Ile Leu Glu Asp Trp
                325                 330                 335

Tyr Pro Gly Asp Asp Thr Val Asp Ile Leu Ser Ala Asp Val Tyr Ala
                340                 345                 350

Gln Gly Asn Gly Pro Met Ser Thr Gln Tyr Asn Glu Leu Ile Ala Leu
            355                 360                 365

Gly Arg Asp Lys Lys Met Ile Ala Ala Ala Glu Val Gly Ala Ala Pro
370                 375                 380

Leu Pro Gly Leu Leu Gln Ala Tyr Gln Ala Asn Trp Leu Trp Phe Ala
385                 390                 395                 400

Val Trp Gly Asp Asp Phe Ile Asn Asn Pro Ser Trp Asn Thr Val Ala
                405                 410                 415

Val Leu Asn Glu Ile Tyr Asn Ser Asp Tyr Val Leu Thr Leu Asp Glu
                420                 425                 430

Ile Gln Gly Trp Arg Ser
            435

<210> SEQ ID NO 30
<211> LENGTH: 443
<212> TYPE: PRT
<213> ORGANISM: Chaetomium globosum

<400> SEQUENCE: 30

Ser Pro Arg Val Phe Glu Ala Glu Asp Ala Thr Leu Gly Gly Thr Thr
1               5                   10                  15

Val Asp Thr Ala Gln Ala Gly Phe Thr Gly Thr Gly Tyr Val Thr Gly
            20                  25                  30

Phe Glu Asp Ala Thr Asp Lys Val Thr Phe Thr Ile Asp Ser Glu Thr
            35                  40                  45

Thr Gln Leu Tyr Asp Leu Ser Ile Arg Ala Ala Ile Tyr Gly Glu
        50                  55                  60

Lys Arg Thr Thr Val Ile Leu Asn Gly Gly Ala Ser Ser Glu Val Leu
65                  70                  75                  80

Phe Pro Ala Ala Asp Thr Trp Ala Asp Ile Ala Gly Gly Gln Leu Leu
                85                  90                  95

Leu Asn Ala Gly Asp Asn Thr Val Glu Ile Val Ser Asn Trp Gly Trp
            100                 105                 110

Tyr Leu Ile Asp Ser Ile Thr Leu Thr Pro Ser Ala Pro Arg Pro Ala
        115                 120                 125

His Asp Ile Asn Pro Ser Pro Val Asn Pro Ser Ala Asn Ala Asp Ala
        130                 135                 140
```

Ile Ala Leu Tyr Ser Tyr Leu Arg Ser Ile Tyr Gly Lys Gln Ile Leu
145 150 155 160

Ser Gly Gln Gln Glu Leu Ser Tyr Ala Asp Trp Ile Ala Glu Gln Thr
165 170 175

Gly Lys Thr Pro Ala Leu Val Ser Val Asp Leu Met Asp Tyr Ser Pro
180 185 190

Ser Arg Val Glu Arg Gly Thr Val Gly Thr Ala Val Glu Glu Ala Ile
195 200 205

Thr His His Glu Arg Gly Gly Ile Val Ser Val Leu Trp His Trp Asn
210 215 220

Ala Pro Thr Gly Leu Tyr Asp Thr Glu Glu Gln Arg Trp Trp Ser Gly
225 230 235 240

Phe Tyr Thr Ala Ala Thr Asp Phe Asp Val Glu Ala Ala Leu Ala Ser
245 250 255

Thr Thr Asn Ala Asn Tyr Thr Leu Leu Ile Arg Asp Ile Asp Ala Ile
260 265 270

Ala Val Glu Leu Lys Arg Leu Gln Ala Ala Glu Val Pro Val Leu Phe
275 280 285

Arg Pro Leu His Glu Ala Glu Gly Gly Trp Phe Trp Trp Gly Ala Lys
290 295 300

Gly Pro Glu Pro Ala Lys Lys Leu Trp Gly Ile Leu Tyr Glu Arg Leu
305 310 315 320

Thr Val His His Glu Ile Asn Asn Leu Ile Trp Val Trp Asn Ser Leu
325 330 335

Ala Glu Ser Trp Tyr Pro Gly Asp Asp Thr Val Asp Ile Leu Ser Ala
340 345 350

Asp Val Tyr Ala Gln Gly Asn Gly Pro Met Ser Thr Gln Tyr Asn Gln
355 360 365

Leu Ile Glu Leu Gly Lys Asp Lys Lys Met Ile Ala Ala Ser Glu Val
370 375 380

Gly Ala Ala Pro Leu Pro Asp Gln Leu Gln Ala Tyr Glu Ala His Trp
385 390 395 400

Ser Trp Phe Ala Val Trp Gly Asp Thr Phe Ile Asn Asn Pro Asp Trp
405 410 415

Asn Ser Pro Glu Asn Leu Lys Thr Val Gly Tyr Leu Pro Ala Gln Ser
420 425 430

Ile Ile Arg Val Gly Ser Leu Asp Ala Asn Arg
435 440

<210> SEQ ID NO 31
<211> LENGTH: 465
<212> TYPE: PRT
<213> ORGANISM: Clostridium lentocellum

<400> SEQUENCE: 31

Tyr Glu Ala Glu Glu Ala Thr Leu His Asn Val Gly Leu Gly Asp Asn
1 5 10 15

Ser Tyr Lys Gly Tyr Ser Gly Asp Gly Tyr Val Ala Gly Met Asp Thr
20 25 30

Ser Asp Ala Tyr Ile Glu Phe Thr Val Thr Val Pro Lys Ser Gly Arg
35 40 45

Tyr Asn Leu Tyr Val Asn Tyr Cys Ala Pro Tyr Gly Glu Lys Gln Glu
50 55 60

Thr Ile Thr Val Asn Gly Gly Gln Ser Phe Ser Gly Leu Phe Thr Ser

```
            65                  70                  75                  80
        Asn Asn Ala Phe Glu Leu Met Asn Val Gly Ala Ile Lys Leu Asn Ala
                         85                  90                  95
        Gly Glu Asn Lys Ile Arg Ile Ser Arg Phe Trp Gly Trp Thr Leu Phe
                        100                 105                 110
        Asp Tyr Ile Glu Leu Glu Ala Gly Ala Ile Asn Ile Asn Thr Asp
                        115                 120                 125
        Val Ser Asp Glu Leu Ile Asn Pro Asn Ala Thr Glu Ala Thr Lys Arg
            130                 135                 140
        Leu Met Thr Tyr Leu Thr Ser Ile Tyr Gly Glu Asn Ile Leu Ser Gly
        145                 150                 155                 160
        Gln Phe Ala Tyr Thr Thr Lys Tyr Thr Glu Ile Asp Ala Ile Tyr Asn
                        165                 170                 175
        Gln Thr Lys Lys Tyr Pro Ala Ile Ile Gly Leu Asp Phe Ser Asp Tyr
                        180                 185                 190
        Ser Pro Ser Arg Val Ala Leu Gly Cys Asn Lys Gly Gln Asp Thr Glu
                        195                 200                 205
        Lys Ala Ile Glu Trp Trp Lys Gln Gly Gly Leu Val Thr Phe Cys Trp
            210                 215                 220
        His Trp Gln Ser Pro Ile Gly Ala Ser Thr Asp Glu Asp Lys Lys Trp
        225                 230                 235                 240
        Gly Gly Phe Tyr Thr Lys Asn Thr Thr Tyr Asp Leu Gly Lys Ala Met
                        245                 250                 255
        Ser Asn His Asn Ser Glu Glu Tyr Ile Thr Leu Ile Arg Asp Ile Asp
                        260                 265                 270
        Ala Ile Ala Val Glu Leu Lys Lys Leu Gln Glu Ala Asn Val Pro Ile
            275                 280                 285
        Leu Trp Arg Pro Leu His Glu Ala Ser Gly Gly Trp Phe Trp Trp Gly
            290                 295                 300
        Ala Ala Gly Ala Asp Asn Tyr Lys Glu Leu Trp Thr Leu Met Tyr Asp
        305                 310                 315                 320
        Arg Leu Thr Asn Tyr His Gly Ile Asn Asn Leu Ile Trp Val Trp Asn
                        325                 330                 335
        Ala Gln Asp Lys Asp Trp Tyr Pro Gly Asp Glu Tyr Val Asp Ile Ile
                        340                 345                 350
        Gly Glu Asp Ile Tyr Ala Asn Lys Lys Asp Tyr Asp Ser Gln Ser Asn
                        355                 360                 365
        Gly Phe Leu Lys Ala Tyr Asp Tyr Thr Gly Met Asn Lys Ile Ile Thr
                        370                 375                 380
        Met Ser Glu Asn Gly Val Leu Met Asp Pro Asp Thr Leu Val Ala Asp
        385                 390                 395                 400
        Gly Ile Pro Trp Leu Trp Asn Cys Thr Trp Gly Gly Glu Phe Val Val
                        405                 410                 415
        Pro Trp Val Gly Ser Tyr Asp Tyr Thr Glu Gln Tyr Thr Ser Leu Asp
                        420                 425                 430
        Met Leu Lys Lys Tyr Tyr Asp His Ser Tyr Val Leu Thr Arg Asp Glu
                        435                 440                 445
        Leu Pro Ala Ser Leu Phe Val Asn Ser Asp Val Lys Glu Met Lys Val
            450                 455                 460
        Ser
        465

<210> SEQ ID NO 32
```

```
<211> LENGTH: 440
<212> TYPE: PRT
<213> ORGANISM: Glomerella graminicola

<400> SEQUENCE: 32

Tyr Glu Ala Glu Asn Gly Ile Leu Ser Gly Thr Arg Ile Glu Lys Ala
1               5                   10                  15

Gln Ala Gly Phe Thr Gly Thr Gly Tyr Val Thr Gly Phe Glu Asp Ala
            20                  25                  30

Thr Asp Lys Val Thr Ile Asn Val Asp Cys Lys Gly Asp Gly Gln Lys
        35                  40                  45

Leu Leu Asp Leu Ser Ile Arg Tyr Ala Ala Ile Tyr Gly Glu Lys Arg
    50                  55                  60

Thr Asn Val Val Phe Asn Gly Ala Ala Ser Glu Val Leu Leu Thr
65                  70                  75                  80

Ala Gly Gln Thr Trp Ala Asp Val Asn Ala Gly Gln Val Leu Leu Asn
                85                  90                  95

Glu Gly Asn Asn Thr Ile Asp Ile Val Ser Asn Trp Gly Trp Tyr Leu
            100                 105                 110

Ile Asp Ser Ile Thr Leu Thr Pro Thr Lys Ala Arg Gly Pro His Asp
        115                 120                 125

Ile Asn Thr Ala Leu Val Asn Pro Lys Ala Asn Ala Asp Ala Asn Ala
    130                 135                 140

Leu Tyr Lys Tyr Leu Gly Ser Ile Tyr Gly Lys Asn Ile Leu Ser Gly
145                 150                 155                 160

Gln Gln Glu Leu Ser Tyr Ala Asn Trp Val Asn Glu Thr Ile Gly Lys
                165                 170                 175

Thr Pro Ala Leu Val Ser Val Asp Leu Met Asp Tyr Thr Pro Ser Arg
            180                 185                 190

Val Glu His Gly Thr Val Gly Thr Ala Val Glu Glu Ala Ile Ala His
        195                 200                 205

His Glu Arg Gly Gly Ile Val Ser Val Leu Trp His Trp Asn Ala Pro
    210                 215                 220

Ala Gly Leu Tyr Asp Thr Glu Glu Asn Pro Trp Trp Ser Gly Phe Tyr
225                 230                 235                 240

Thr Arg Ala Thr Asp Phe Asp Val Ala Thr Ala Leu Ala Asp Pro Gly
                245                 250                 255

Gly Ala Asn Tyr Thr Leu Ile Ile Arg Asp Met Asp Ala Ile Ala Val
            260                 265                 270

Gln Leu Ala Arg Leu Arg Asp Ala Gly Val Pro Val Ile Trp Arg Pro
        275                 280                 285

Leu His Glu Ala Glu Gly Glu Trp Phe Trp Trp Gly Ala Gln Gly Pro
    290                 295                 300

Glu Ala Cys Lys Lys Leu Tyr Ala Leu Leu Tyr Asp Arg Leu Thr Asn
305                 310                 315                 320

His His Gly Leu Asp Asn Leu Ile Trp Asn Trp Asn Ser Val Ser Ala
                325                 330                 335

Asp Trp Tyr Pro Gly Asp Asp Thr Val Asp Ile Val Ser Thr Asp Val
            340                 345                 350

Tyr Ala Gln Gly His Gly Pro Met Thr Ser Gln Tyr Asn Asp Leu Leu
        355                 360                 365

Ala Leu Val Lys Asp Lys Lys Leu Val Ala Ala Glu Val Gly Ser
    370                 375                 380

Ala Pro Phe Pro Asp Leu Leu Gln Ala Tyr Gly Ala Asp Trp Leu Tyr
```

```
                385                 390                 395                 400
Phe Cys Val Trp Ser Asp Thr Tyr Ile Asn Asn Pro Glu Trp Asn Ser
                    405                 410                 415

Val Glu Asp Leu Lys Lys Ile Tyr Asp Ser Glu Tyr Val Leu Thr Leu
                    420                 425                 430

Asp Glu Ile Gln Gly Trp Arg Gly
                    435                 440
```

<210> SEQ ID NO 33
<211> LENGTH: 355
<212> TYPE: PRT
<213> ORGANISM: Aspergillus nidulans

<400> SEQUENCE: 33

```
Met Lys Phe Ser Gln Leu Ile Leu Pro Phe Ala Ala Leu Ser Leu
1               5                   10                  15

Val Gly Ser Gly Val Ala Thr Pro Thr Thr Lys Pro Val Asn Pro Arg
                20                  25                  30

Ala Ser Arg Pro Ala Arg Asn Leu Leu Ala His Leu Val Arg Ser Ala
                35                  40                  45

Gly Asn Gly Thr Thr Leu Ser Gly Gln Gln Glu Leu Lys Asp Ala Asp
            50                  55                  60

Trp Val Thr Asp Asn Val Gly Phe Ser Pro Val Ile Leu Gly Val Asp
65                  70                  75                  80

Leu Met Asp Tyr Ser Pro Ser Arg Val Glu Phe Gly Ala Val Ser Thr
                85                  90                  95

Ser Ile Glu Asp Ala Ile Thr Tyr Ala Thr Gln Gly Gly Ile Ile Thr
                100                 105                 110

Ile Cys Trp His Trp Gly Glu Leu Ser His Asp Trp Met Thr Asp Glu
                115                 120                 125

Arg Leu Thr Thr Leu Leu Thr Leu Gly Ser Pro Ser Gly Thr Tyr Asn
                130                 135                 140

Thr Thr Glu Gln Pro Trp Trp Ser Asn Phe Tyr Thr Glu Ala Thr Ser
145                 150                 155                 160

Phe Asn Leu Ser Ala Ala Met Asn Pro Ala Ser Arg Asp Tyr Lys Leu
                165                 170                 175

Ile Leu Arg Asp Ile Asp Ala Ile Ala Glu Gln Leu Ala Arg Leu Lys
                180                 185                 190

Asp Ile Pro Val Leu Phe Arg Pro Leu His Glu Ala Glu Gly Gly Trp
                195                 200                 205

Phe Trp Trp Gly Ala Thr Gly Ala Glu Pro Cys Lys Ala Leu Tyr Arg
                210                 215                 220

Leu Leu Phe Asp Arg Leu Thr Lys Lys His Gly Leu Asn Asn Leu Leu
225                 230                 235                 240

Trp Val Trp Asn Ser Lys Asp Pro Leu Trp Tyr Pro Gly Asn Glu Tyr
                245                 250                 255

Val Asp Val Val Ser Val Asp Val Tyr Ala Asp Asn Gly Asp His Ser
                260                 265                 270

Ser Gln Leu Glu Ala Tyr Gln Ala Leu Gln Gly Leu Thr Gly Asn Phe
                275                 280                 285

Ser Lys Leu Ile Ala Leu Gly Glu Val Gly Asn Ile Pro Asp Pro Glu
                290                 295                 300

Leu Met Arg Glu Asp Gly Ala Gln Trp Ala Tyr Trp Val Thr Trp Asn
305                 310                 315                 320
```

```
Gly Asp Phe Ile Arg Gly Glu Thr Lys Asn Pro Met Glu Phe Lys Lys
                325                 330                 335

Ala Val Tyr Ala Ser Glu Leu Val Tyr Thr Leu Asp Glu Ile Gln Gly
            340                 345                 350

Trp Asn Leu
        355

<210> SEQ ID NO 34
<211> LENGTH: 453
<212> TYPE: PRT
<213> ORGANISM: Spirosoma linguale

<400> SEQUENCE: 34

Pro Ile Lys Val Glu Ala Glu Leu Gly Glu Leu Thr Gly Val Glu Val
1               5                   10                  15

Ala Ser Thr Asn Lys Gly Phe Ser Gly Thr Gly Tyr Val Thr Gly Leu
            20                  25                  30

Asp Asp Pro Thr Asp Lys Leu Val Leu Thr Val Asn Ala Pro Ala Gly
            35                  40                  45

Leu Tyr Glu Leu Ala Ile Gly Tyr Ala Ser Pro Phe Gly Asp Lys Gly
 50                  55                  60

Ile Asp Phe Gln Val Asn Glu Glu Arg Gly Ser Gly Met Leu Lys Gln
65                  70                  75                  80

Thr Ser Ala Gly Phe Thr Thr Ala Gly Leu Gly Lys Phe Leu Leu Thr
                85                  90                  95

Glu Gly Lys Asn Thr Ile Thr Ile Tyr Arg Gly Trp Gly Tyr Phe Asp
            100                 105                 110

Ile Asp Tyr Leu Leu Phe Thr Pro Ala Thr Val Val Leu Pro Thr Lys
        115                 120                 125

Pro Gln Lys Thr Leu Val Asp Ala Gln Ala Thr Leu Ser Thr Lys Gly
        130                 135                 140

Leu Phe Ser Tyr Leu Val Asp Gln Tyr Gly Ser Lys Val Ile Ser Gly
145                 150                 155                 160

Gln Gln Asp Asp Val Glu Tyr Ile Leu Glu Lys Thr Gly Lys Glu Pro
                165                 170                 175

Ala Ile Gly Ser Phe Asp Leu Ile Asp Tyr Ser Pro Ser Arg Val Gln
            180                 185                 190

Phe Gly Ala Thr Pro Gln Arg Ser Ser Glu Asp Ile Ile Lys Trp Ala
        195                 200                 205

Lys Lys Gly Asp Gly Arg Gly Ile Ile Ser Leu Met Trp His Trp Asn
    210                 215                 220

Ala Pro Thr Asp Leu Ile Asn Gln Ser Pro Asp Lys Leu Trp Trp Arg
225                 230                 235                 240

Gly Phe Tyr Thr Asp Ala Thr Thr Phe Asp Ile Ala Ala Val Leu Ala
                245                 250                 255

Asp Lys Gln Gly Glu Arg Tyr Gln Leu Ile Leu Arg Asp Ile Asp Ala
            260                 265                 270

Ile Ala Leu Gln Leu Lys Lys Phe Gln Ala Ala Asp Val Pro Val Leu
        275                 280                 285

Trp Arg Pro Leu His Glu Ala Ser Gly Gly Trp Phe Trp Trp Gly Ala
        290                 295                 300

Lys Gly Ala Gly Pro Leu Lys Glu Leu Trp Arg Val Leu Tyr Asp Arg
305                 310                 315                 320

Leu Ile Asn Tyr His Gln Leu His Asn Leu Ile Trp Val Tyr Thr Ala
                325                 330                 335
```

```
Thr Asp Thr Phe Lys Ser Asp Trp Tyr Pro Gly Asp Gln Tyr Val Asp
            340                 345                 350

Ile Val Gly Met Asp Ile Tyr Thr Asp Pro Thr Ala Asn Met Ser Gly
            355                 360                 365

Asn Trp Ser Ser Ala Gln Ser Gln Leu Asn Gly Lys Lys Leu Val Thr
370                 375                 380

Leu Ser Glu Thr Gly Asn Leu Pro Ser Pro Asp Lys Ile Arg Gly Phe
385                 390                 395                 400

Gly Thr Trp Trp Ser Trp Phe Ala Val Trp Thr Gly Thr Asp Tyr Ile
                405                 410                 415

Lys Lys Gln Pro Ile Asp Gln Leu Lys Ala Val Phe Thr Asp Arg Asp
            420                 425                 430

Val Ile Thr Arg Asp Glu Leu Pro Asp Trp Arg Pro Pro Leu Thr Leu
            435                 440                 445

Ala Val Glu Glu Pro
    450

<210> SEQ ID NO 35
<211> LENGTH: 436
<212> TYPE: PRT
<213> ORGANISM: Sordaria macrospora

<400> SEQUENCE: 35

Tyr Glu Ala Glu Asp Ala Val Leu Ser Gly Thr Gln Ile Leu Thr Ala
1               5                   10                  15

Gln Ser Gly Phe Ser Gly Ser Gly Tyr Val Gly Gly Phe Asp Thr Gly
            20                  25                  30

Thr Asp Lys Ile Thr Phe Thr Ile Pro Ser Ser Ser Ala Lys Leu Tyr
        35                  40                  45

Asp Leu Ser Ile Arg Tyr Ala Gly Ile Tyr Gly Asp Lys Arg Thr Asn
50                  55                  60

Val Val Leu Asn Gly Ala Ser Thr Glu Val Ser Leu Pro Ala Thr Asp
65                  70                  75                  80

Ser Phe Ala Thr Val Ser Gly Gly Gln Ile Leu Leu Asn Glu Gly Thr
                85                  90                  95

Asn Thr Leu Glu Ile Val Ser Asn Trp Gly Trp Tyr Leu Ile Asp Tyr
            100                 105                 110

Ile Leu Ile Thr Pro Ala Thr Lys Gly Gly Ala His Asn Ile Asn Thr
        115                 120                 125

Asn Leu Pro Ser Ser Cys Thr Leu Thr Ser Ala Pro Ile Tyr Gly Lys
    130                 135                 140

Lys Ile Leu Ser Gly Gln Gln Asp Leu Ser Tyr Ala Asn Tyr Val Ser
145                 150                 155                 160

Ser Thr Thr Gly Lys Thr Pro Ala Leu Val Ser Ser Asp Leu Met Asp
                165                 170                 175

Tyr Ser Pro Ser Arg Val Ala His Gln Gly Asp Val Ser His Ala Val
            180                 185                 190

Glu Glu Ala Ile Thr His His Gln Arg Gly Gly Ile Val Ser Ile Leu
        195                 200                 205

Trp His Trp Asn Ala Pro Thr Gly Leu Tyr Asp Thr Ser Glu Asn Pro
    210                 215                 220

Trp Trp Ser Gly Phe Tyr Thr Arg Ala Thr Asn Phe Asp Ile Ala Ala
225                 230                 235                 240

Thr Leu Ala Asn Pro Gln Gly Thr Asn Tyr Asn Leu Leu Ile Arg Asp
```

```
            245                 250                 255
Ile Asp Ala Ile Ala Tyr Gln Leu Lys Arg Leu Gln Ser Ala Gly Val
            260                 265                 270

Pro Val Leu Trp Arg Pro Leu His Glu Ala Glu Gly Gly Trp Phe Trp
            275                 280                 285

Trp Gly Ala Lys Gly Ser Ala Pro Ala Lys Gln Leu Tyr His Ile Met
290                 295                 300

Tyr Glu Arg Leu Thr Lys Val His Gly Leu Asn Asn Leu Ile Trp Val
305                 310                 315                 320

Trp Asn Ser Val Ala Gln Asp Trp Tyr Pro Gly Asp Glu Val Val Asp
                325                 330                 335

Ile Val Ser Thr Asp Val Tyr Ala Gln Gly Asn Gly Pro Met Ser Ala
                340                 345                 350

Gln Tyr Asn Glu Leu Val Ala Leu Gly Lys Asp Arg Lys Met Val Ala
                355                 360                 365

Ala Ala Glu Val Gly Ala Ala Pro Arg Pro Asp Leu Leu Val Ala Tyr
            370                 375                 380

Gly Ala His Trp Leu Trp Phe Cys Thr Trp Gly Asp Ser Phe Ile Asp
385                 390                 395                 400

Asn Ala Asp Trp Asn Ser Pro Ala Val Leu Asn Glu Ile Tyr His His
                405                 410                 415

Asp Tyr Val Leu Thr Leu Asp Glu Ile Gln Gly Trp Lys Asn Ile Gly
                420                 425                 430

Ala Ala Gln Leu
            435

<210> SEQ ID NO 36
<211> LENGTH: 445
<212> TYPE: PRT
<213> ORGANISM: Botryotinia fuckeliana

<400> SEQUENCE: 36

Val Glu Ala Glu Thr Gly Ile Leu Asn Gly Val Thr Ile Gly Asp Asn
1               5                   10                  15

Pro Gly Gly Phe Ser Gly Ser Gly Phe Val Gln Gly Phe Asp Ala Ala
            20                  25                  30

Thr Asp Ser Val Thr Ile Thr Phe Gln Ser Ala Lys Gln Ala Leu Tyr
        35                  40                  45

Asp Val Val Ile Gln Tyr Ala Ser Thr Ser Gly Glu Lys Gln Thr Thr
    50                  55                  60

Met Ser Leu Asn Asp Ser Gly Ser Gly Ile Val Leu Ala Ala Thr
65                  70                  75                  80

Ser Glu Glu Ser Pro Trp Ala Asn Ala Thr Ala Gly Gln Val Leu Leu
                85                  90                  95

Asn Ala Gly Thr Asn Thr Ile Thr Phe Thr Ser Asn Trp Gly Trp Tyr
            100                 105                 110

Phe Ile Asp Ala Val Tyr Ile Ser Pro Ser Ala Ala Pro Ala Lys His
        115                 120                 125

Gln Val Thr Ser Lys Leu Ser Thr Pro Asn Pro Leu Pro Ile Thr Gln
    130                 135                 140

Ala Leu Phe Asn Lys Leu Leu Ser Asn Tyr Gly Asn Gly Ser Ile Phe
145                 150                 155                 160

Ser Gly Gln Ser Glu Ala Ala Glu Ile Ala Trp Leu Glu Glu Asn Val
                165                 170                 175
```

-continued

```
Gly Lys Thr Pro Ala Ile Ile Gly Leu Asp Phe Met Asp Tyr Ser Pro
            180                 185                 190

Ser Arg Val Glu His Gly Thr Ser Ser His Glu Val Glu Asp Gly Ile
        195                 200                 205

Ala Phe Ser Asn Arg Asn Gly Ile Val Ala Phe Gln Trp His Trp Asn
    210                 215                 220

Ala Pro Ser His Leu Ile Asp Ser Ala Ala Glu Pro Trp Tyr Ser Gly
225                 230                 235                 240

Phe Tyr Thr Ala Ala Thr Thr Phe Asn Leu Thr Thr Val Leu Ala Asn
                245                 250                 255

Pro Ser Ser Glu Asp Tyr Ala Leu Leu Ile Arg Asp Leu Asp Thr Ile
            260                 265                 270

Ala Ala Leu Leu Leu Arg Leu Gln Ala Ala Asp Val Pro Val Leu Trp
        275                 280                 285

Arg Pro Leu His Glu Ala Glu Gly Gly Trp Phe Trp Trp Gly Ala Gln
    290                 295                 300

Gly Pro Glu Ala Cys Val Ala Leu Tyr Arg Leu Met Phe Asp Arg Phe
305                 310                 315                 320

Val Asn His His Gln Leu Arg Asn Leu Ile Trp Val Trp Asn Ser Val
                325                 330                 335

Ala Thr Ala Trp Tyr Pro Gly Asp Asp Ile Val Asp Ile Leu Gly Tyr
            340                 345                 350

Asp Ser Tyr Pro Pro Ala Gly Asp His Gly Ala Val Ser Val Gln Tyr
        355                 360                 365

Gln Ala Leu Ile Ala Leu Gly Lys Asp Lys Lys Met Val Thr Leu Pro
    370                 375                 380

Glu Val Gly Asn Ile Pro Asp Pro Asp Gln Leu Glu Leu Tyr His Ala
385                 390                 395                 400

Asp Trp Ser Tyr Phe Val Thr Trp Asn Gly Ala Tyr Ile Asn Thr Asp
                405                 410                 415

Glu Phe Asn Ser Leu Asp Phe Lys Lys Lys Val Phe Asn Asp Pro Ser
            420                 425                 430

Val Ile Asn Leu Ser Asp Leu Gly Asn Trp Lys Ser Asn
        435                 440                 445

<210> SEQ ID NO 37
<211> LENGTH: 440
<212> TYPE: PRT
<213> ORGANISM: Leptosphaeria maculans

<400> SEQUENCE: 37

Tyr Gln Ala Glu Asp Ala Thr Leu Ser Gly Thr Thr Val Gly Thr Ser
1               5                   10                  15

Val Ala Gly Phe Thr Gly Ser Gly Tyr Val Glu Asn Phe Ala Asp Ala
            20                  25                  30

Thr Asp Lys Ile Thr Phe Asn Ile Asn Ala Asp Asn Ser Gly Leu Tyr
        35                  40                  45

Asp Leu Ser Ile Ile Tyr Asn Gly Pro Tyr Gly Asp Lys Tyr Thr Ser
    50                  55                  60

Val Val Leu Asn Gly Gly Gly Ala Ser Gln Val Ser Leu Pro Ala Thr
65                  70                  75                  80

Thr Ser Trp Thr Thr Val Ser Ala Gly Gln Val Leu Leu Asn Thr Gly
                85                  90                  95

Ser Asn Thr Ile Glu Ile Gln Asn Asn Trp Gly Trp Tyr Leu Ile Asp
            100                 105                 110
```

```
Ala Ile Thr Ile Ala Pro Ser Ala Pro Arg Pro His Asn Ile Ser
            115                 120                 125
Thr Thr Pro Val Asn Pro Lys Ala Asn Ala Asp Ala Lys Ala Leu Leu
130                 135                 140
Ser Tyr Leu Gly Ser Ile Tyr Gly Lys Asn Ile Leu Ser Gly Gln Gln
145                 150                 155                 160
Asp Gln Ala Ser Phe Asp Trp Val Lys Gln Asn Ile Gly His Thr Pro
            165                 170                 175
Ala Ile Leu Gly Leu Asp Leu Met Asp Tyr Thr Asp Ser Arg Thr Ser
            180                 185                 190
Arg Gly Ala Ser Ser Arg Asp Val Glu His Ala Leu Thr Phe Ala Gln
            195                 200                 205
Gln Gly Gly Ile Val Thr Phe Val Trp His Trp Gly Ala Pro Val Gly
            210                 215                 220
Leu Tyr Asp Asn Ala Thr Gln Pro Trp Tyr Arg Gly Phe Tyr Thr Ala
225                 230                 235                 240
Ala Thr Asp Phe Ser Leu Arg Ala Ala Leu Ala Asp Thr Thr Asn Ala
            245                 250                 255
Asn Tyr Thr Leu Leu His Asp Ile Asp Thr Ile Ala Thr Gln Leu
            260                 265                 270
Leu Lys Leu Gln Asp Ala Gly Val Pro Val Leu Phe Arg Pro Leu His
            275                 280                 285
Glu Ala Glu Gly Ala Trp Phe Trp Trp Gly Ala Asp Gly Pro Glu Pro
290                 295                 300
Cys Lys Gln Leu Trp Arg Leu Leu Tyr Asp Arg Leu Thr Asn His His
305                 310                 315                 320
Asn Leu His Asn Leu Leu Trp Val Trp Asn Ser Val Ala Pro Ser Trp
            325                 330                 335
Tyr Pro Gly Asp Asp Val Val Asp Ile Val Ser Ala Asp Thr Tyr Thr
            340                 345                 350
Gln Gly Asp His Gly Pro Asn Ser Ala Thr Tyr Asn Ala Leu Leu Asp
            355                 360                 365
Leu Thr Asp Asp Thr Lys Ile Val Ala Ala Thr Glu Ile Gly Ser Leu
            370                 375                 380
Met Glu Val Glu Gly Leu Lys Ala Tyr Asp Ala His Trp Ala Trp Phe
385                 390                 395                 400
Val Val Trp Ser Gly Glu Tyr Val Ser Gly Gln Trp Asn Ser Val
            405                 410                 415
Asp Leu Leu Lys Arg Val Tyr Ala Asp Glu Tyr Val Leu Thr Leu Ala
            420                 425                 430
Glu Ile Gly Gly Trp Lys Gly Arg
            435                 440

<210> SEQ ID NO 38
<211> LENGTH: 476
<212> TYPE: PRT
<213> ORGANISM: Clostridium thermocellum

<400> SEQUENCE: 38

Ser Asp Gly Asp Lys Tyr Glu Phe Glu Asp Gly Ile His Lys Gly Ala
1               5                   10                  15
Gln Ile Tyr Thr Asp Tyr Val Gly Gln Asn Glu Tyr Gly Glu Val Phe
            20                  25                  30
Asp Leu Thr Gly Ser Thr Cys Ser Phe Ile Ala Gln Lys Gly Thr Ser
```

```
            35                  40                  45
Thr Ser Val Asn Val Glu Val Asp Lys Glu Gly Leu Tyr Glu Ile Phe
 50                  55                  60

Ile Cys Tyr Val Gln Pro Tyr Asp Lys Asn Lys Val Gln Tyr Leu
65                   70                  75                  80

Asn Val Asn Gly Val Asn Gln Gly Glu Ile Ser Phe Pro Phe Thr Leu
                     85                  90                  95

Lys Trp Arg Glu Ile Ser Ala Gly Ile Val Lys Leu Asn Ala Gly Ile
                100                 105                 110

Asn Asn Ile Glu Leu Glu Ser Tyr Trp Gly Tyr Thr Tyr Phe Asp Tyr
                115                 120                 125

Leu Ile Val Lys Pro Ala Asp Glu Ser Ile Val Glu Leu Lys Val Pro
                130                 135                 140

Lys Lys Leu Val Asn Pro Asn Ala Thr Lys Glu Ala Lys Ala Leu Met
145                 150                 155                 160

Ser Tyr Leu Val Asp Ile Tyr Gly Lys His Ile Leu Ser Gly Gln Gln
                    165                 170                 175

Glu Ile Cys Gly Ser His Asn Tyr Pro Gly Ser Glu Ala Glu Phe Thr
                180                 185                 190

Tyr Ile Gln Glu Lys Thr Gly Lys Leu Pro Ala Val Arg Gly Phe Asp
                195                 200                 205

Phe Met Asn Tyr Arg Gly Asn Gly Leu Met Trp Asp Asp Gln Cys Ala
210                 215                 220

Glu Arg Val Ile Glu Trp Tyr Lys Glu Lys Gly Gly Ile Pro Thr Val
225                 230                 235                 240

Cys Trp His Trp Phe Ser Pro Gly Asp Ile Gly Lys Lys Ala Asp Asn
                    245                 250                 255

Ser Phe Tyr Thr Glu Ser Thr Thr Phe Ser Ile Ser Arg Ala Leu Thr
                260                 265                 270

Pro Gly Thr Glu Glu Asn Ile Ala Leu Leu Asn Asp Ile Asp Thr Ile
                275                 280                 285

Ala Arg Lys Leu Lys Gln Val Gln Asp Ala Gly Val Pro Val Leu Phe
290                 295                 300

Arg Pro Leu His Glu Ala Glu Gly Gly Trp Phe Trp Trp Gly Ala Glu
305                 310                 315                 320

Gly Pro Glu Pro Cys Val Arg Leu Tyr Arg Leu Leu Tyr Asp Lys Phe
                325                 330                 335

Thr Asn Glu Tyr Gly Leu Asn Asn Leu Ile Trp Val Trp Thr Ser Tyr
                340                 345                 350

Asp Tyr Glu Thr Ser Ala Ala Trp Tyr Pro Gly Asp Asp Val Val Asp
                355                 360                 365

Ile Ile Gly Tyr Asp Lys Tyr Asn Ala Lys Asp Gly Lys Pro Asn Gly
                370                 375                 380

Ser Ala Ile Ser Ser Thr Phe Tyr Asn Leu Val Lys Leu Thr Asn Gly
385                 390                 395                 400

Lys Lys Leu Val Ala Met Thr Glu Asn Asp Thr Ile Pro Arg Val Ser
                    405                 410                 415

Asn Leu Val Asn Glu Lys Ala Gly Trp Leu Tyr Phe Cys Pro Trp Tyr
                420                 425                 430

Gly Trp Trp Leu Thr Ser Glu Gln Asn Asn Pro Val Asp Trp Leu Val
                435                 440                 445

Glu Met Tyr Gln Ser Asp Tyr Cys Ile Thr Leu Asp Glu Leu Pro Asp
                450                 455                 460
```

Leu Lys Asn Tyr Pro Ile Ser Asp Tyr Glu Asp Ser
465                 470                 475

<210> SEQ ID NO 39
<211> LENGTH: 454
<212> TYPE: PRT
<213> ORGANISM: Ruminococcus albus

<400> SEQUENCE: 39

Arg Tyr Glu Ala Glu Lys Ala Val Leu Asp Lys Val Asp Val Gln Gly
1               5                   10                  15

Asp Tyr Val Ser Leu Lys Ser Glu Gly Ser Val Thr Phe Lys Val Glu
            20                  25                  30

Ile Ser Glu Thr Gly Trp Tyr Asp Leu Asp Phe Ile Ser Ser Gly Ile
        35                  40                  45

Gly Gly Ser Lys Glu Asn Asn Ala Ser Val Asp Gly Glu Phe Thr Gly
    50                  55                  60

Arg Phe Lys Ser Glu Ser Gly Ala Met Asn Asp Ser Ile Lys Asn
65                  70                  75                  80

Val Phe Met Glu Lys Gly Ser His Asp Ile Thr Val Thr Pro Ser Trp
                85                  90                  95

Gly Trp Ile Asn Ile Asp Ala Leu Val Ile Asn Ala Ala Gln Leu Lys
            100                 105                 110

Asn Ser Tyr Asp Val Lys Gly Glu Leu Ser Asn Lys Asn Ala Thr Asp
        115                 120                 125

Ser Thr Lys Arg Leu Met Ala Phe Leu Lys Asp Asn Tyr Gly Met Lys
130                 135                 140

Thr Ile Ser Gly Gln Gln Cys Asp Gly Gly Leu Asn Gly Thr Glu Phe
145                 150                 155                 160

Lys Val Ile Lys Glu Ala Thr Gly Lys Thr Pro Ala Leu Val Gly Leu
                165                 170                 175

Asp Leu Met Asp Tyr Thr Pro Ser Arg Val Ser Leu Gly Ala Lys Gly
            180                 185                 190

Asn Ser Val Glu Lys Ala Ile Glu Phe Ser Lys Ala Gly Gly Ile Val
        195                 200                 205

Glu Met Cys Trp His Trp Ser Ala Pro Arg Lys Tyr Ile Lys Glu Gly
210                 215                 220

Lys Asp Ser Asn Gly Asn Pro Met Trp Trp Gly Ser Phe Tyr Thr Ala
225                 230                 235                 240

Asn Val Thr Ile Asp Phe Asp Ala Val Met Asn Gly Lys Asp Pro Glu
                245                 250                 255

Gly Tyr Lys Leu Leu Met Ser Asp Ile Asp Thr Ile Ala Ala Glu Leu
            260                 265                 270

Lys Lys Leu Gln Asp Ala Asp Val Pro Ile Leu Phe Arg Pro Leu His
        275                 280                 285

Glu Gly Ser Gly Gly Trp Phe Trp Trp Gly Ser Gly Ser Ala Asn Ser
290                 295                 300

Tyr Lys Lys Leu Trp Val Thr Met Tyr Asp Lys Leu Thr Asn Glu His
305                 310                 315                 320

Gly Leu Asn Asn Leu Ile Trp Val Tyr Asn Gly Gln Ser Lys Asp Trp
                325                 330                 335

Tyr Pro Gly Asp Glu Tyr Val Asp Ile Ile Gly Glu Asp Ile Tyr Pro
            340                 345                 350

-continued

```
Gly Lys Gln Val Thr Ser Pro Gln Ser Ser Lys Phe Leu Glu Ala Ala
        355                 360                 365

Asp Tyr Thr Asp Asp Thr Lys Ile Val Thr Leu Ser Glu Asn Gly Cys
    370                 375                 380

Leu Phe Asp Pro Asp Val Ala His Asp Arg Asn Thr Leu Trp Ser Trp
385                 390                 395                 400

Phe Cys Ile Trp Gly Gly Glu Phe Val Arg Ser Gly Ser Lys Leu Ser
                405                 410                 415

Glu Glu Tyr Ser Thr Ala Glu Met Trp Lys Lys Val Tyr Asn Ser Glu
            420                 425                 430

Tyr Val Leu Thr Leu Asp Glu Leu Pro Asp Leu Arg Ser Tyr Pro Val
        435                 440                 445

Glu Gly Asp Val Pro Pro
    450
```